US007728176B2

(12) United States Patent
Masaoka et al.

(10) Patent No.: US 7,728,176 B2
(45) Date of Patent: Jun. 1, 2010

(54) PROCESS FOR PRODUCING PHOSPHONIUM BORATE COMPOUND, NOVEL PHOSPHONIUM BORATE COMPOUND, AND METHOD OF USING THE SAME

(75) Inventors: Shin Masaoka, Atsugi (JP); Hideyuki Iwazaki, Atsugi (JP)

(73) Assignee: Hokko Chemical Industry Co., Ltd., Tokyo (JP)

( * ) Notice: Subject to any disclaimer, the term of this patent is extended or adjusted under 35 U.S.C. 154(b) by 239 days.

(21) Appl. No.: 10/580,699

(22) PCT Filed: Nov. 26, 2004

(86) PCT No.: PCT/JP2004/017628

§ 371 (c)(1),
(2), (4) Date: May 25, 2006

(87) PCT Pub. No.: WO2005/051963

PCT Pub. Date: Jun. 9, 2005

(65) Prior Publication Data

US 2007/0098616 A1      May 3, 2007

(30) Foreign Application Priority Data

Nov. 28, 2003   (JP)   ............................. 2003-399650
Nov. 28, 2003   (JP)   ............................. 2003-399651

(51) Int. Cl.
*C07F 9/02*         (2006.01)
(52) U.S. Cl. ............................. 568/8; 423/299; 423/276
(58) Field of Classification Search ................. 423/276, 423/299; 568/8
See application file for complete search history.

(56) References Cited

U.S. PATENT DOCUMENTS 7,294,600 B2 * 11/2007 Lee et al. ..................... 502/113

FOREIGN PATENT DOCUMENTS

| JP | 62-149721 | | 7/1987 |
| JP | 62149721 | * | 7/1987 |
| WO | 2006004376 A1 | | 1/2006 |
| WO | 2006031067 A1 | | 3/2006 |

OTHER PUBLICATIONS

Gusev et al., Synthesis, Structural Diversity, Dynamics, and Acidity of the M(II) and M(IV) Complexes [MH3(PR3)4]+ (M = Fe, Ru, Os; R = Me, Et, Journal of the American Chemical Society (1997), 119(16), 3716-3731 (Abstract).*
Gill et al., {Transition metal-carbon bonds. XXXIII. Internal metalations of secondary and tertiary carbon atoms by platinum(II) and palladium(II) Inorganic Chemistry (1972-1999) (1973), (3), 270-278}.*
Smith et al., {Phosphorus mustards. 1-3 III. Bis(2-chloroethyl)methylphosphine oxide and bis(2-benzoxyethyl)methylphosphine, Journal of Medicinal Chemistry, 11(5), 1060-3}.*
Ayllon et al., {Proton Transfer I-3 in Aminocyclopentadienyl Ruthenium Hydride Complexes, Organometallics , 18(20), 3981-3990}.*
Littke, Adam F.; Dai, Chaoyang; and Fu, Gregory C., "Versatile Catalysts for the Suzuki Cross-Coupling of Arylboronic Acids with Aryl and Vinyl Halides and Triflates under Mild Conditions", *Journal of American Chemical Society*, 2000, 122, pp. 4020-4028.
Kirchhoff, Jan H.; Netherton, Matthew R.; Hills, Ivory D.; and Fu, Gregory C., "Boronic Acids: New Coupling Partners in Room-Temperature Suzuki Reactions of Alkyl Bromides. Crystallographic Characterization of an Oxidative-Addition Adduct Generated under Remarkably Mild Conditions", *Journal of American Chemical Society*, 2002, pp. 13662-13663, vol. 124, No. 46.
Jia, Guochen; and Morris, Robert H., "Wide Range of $PK_a$ Values of Coordinated Dihydrogen. Synthesis and Properties of Some $\eta^2$-Dihydrogen and Dihydride Complexes of Ruthenium", *Journal of American Chemical Soceity*, 1991, pp. 875-883, vol. 113, No. 3.
Netherton, Matthew R.; and Fu, Gregory C., "Air-Stable Trialkylphosphonium Salts: Simple, Practical, and Versatile Replacements for Air-Sensitive Trialkylphosphines. Applications in Stoichiometric and Catalytic Processes", *Organic Letters*, 2001. pp. 4295-4298, vol. 3, No. 26.
Ayllon, José A.; Sayers, Stephen F.; Sabo-Etienne, Sylviane; Donnadieu, Bruno; and Chaudret, Bruno, "Proton Transfer in Aminocyclopentadienyl Ruthenium Hydride Complexes", *Organometallics*, 1999, pp. 3981-3990, vol. 18, No. 20.

(Continued)

*Primary Examiner*—Sikarl A Witherspoon
*Assistant Examiner*—Chukwuma O Nwaonicha
(74) *Attorney, Agent, or Firm*—The Webb Law Firm, P.C.

(57) ABSTRACT

The invention relates to a phosphonium borate compound represented by Formula (I) (hereinafter, the compound (I)). The invention has objects of providing (A) a novel process whereby the compound is produced safely on an industrial scale, by simple reaction operations and in a high yield; (B) a novel compound that is easily handled; and (C) novel use as catalyst.

Formula (I): $(R^1)(R^2)(R^3)PH.BAr_4$      (I)

wherein $R^1$, $R^2$, $R^3$ and Ar are as defined in the specification. The process (A) includes reacting a phosphine with a) HCl or b) $H_2SO_4$ to produce a) a hydrochloride or b) a sulfate; and reacting the salt with a tetraarylborate compound. The compound (B) has for example a secondary or tertiary alkyl group as $R^1$ and is easily handled in air without special attention. The use (C) is characterized in that the compound (I) is used instead of an unstable phosphine compound of a transition metal complex catalyst for catalyzing C—C bond, C—N bond and C—O bond forming reactions and the compound produces an effect that is equal to that achieved by the transition metal complex catalyst.

6 Claims, No Drawings

OTHER PUBLICATIONS

Gusev, Dmitry G.; Hübener, Rainer; Burger, Peter; Orama, Olli; and Berke, Heinz; Synthesis, Structural Diversity, Dynamics, and Acidity of the M(II) and M(IV) Complexes.$[MH_3(PR_3)_4]+$(M = Fe, Ru, Os; R =Me, Et), *Journal of American Chemical Society*, 1997, vol. 119, No. 16, pp. 3716-3731.

Gill, D.F.; Mann, B.E.; and Shaw, B.L., "Transition Metal—Carbon Bonds. Part XXXIII. Internal Metallations of Secondary and Tertiary Carbon Atoms by Platinum(II) and Palladium(II)", *Journal of the Chemical Society*, Dalton Transactions: Inorganic Chemistry, 1973, No. 3, pp. 270-278.

Cappellani, E. Paul; Drouin, Samantha D.; Jia, Guochen; Maltby, Patricia A.; Morris, Robert H.; and Schweitzer, Caroline T., "Effect of the Ligand and Metal on the $pK_a$ Values of the Dihydrogen Ligand in the Series of Complexes $[M(H_2)H(L)_2]^+$, M = Fe, Ru, Os, Containing Isosteric Ditertiaryphospine Ligands, L", *Journal American Chemical Society*, 1994, 116, pp. 3375-3388.

Patent Abstracts of Japan, Publication No. JP 62-149721, dated Mar. 7, 1987, "Epoxy Resin Composition for Sealing Semiconductor", applicant: Hitachi Chem. Co., Ltd.; Inventors: Keiichi Kinashi et al.

Netherton, Matthew R.; and Fu, Gregory C., "Air-Stable Trialkylphosphonium Salts: Simple, Practical, and Versatile Replacements for Air-Sensitive Trialkylphosphines. Applications in Stoichiometric and Catalytic Processes", Organic Letters, 2001, pp. 4295-4298, vol. 3, No. 26, Nov. 2003.

Smith et al. "Phosphorus Mustards. III. Bis(2-chloroethyl)methylphosphine Oxide and Bis(2-benzoxyethyl) methylphosphine", Journal of Medicine Chemistry, vol. 11 No. 5, pp. 1060-1063, Sep. 1968.

Tan et al. " Intermolecular Coupling of Alkenes to Heterocycles via C-H Bond Activation", Journal of Organic Chemistry, vol. 69 No. 21, pp. 7329-7335, 2004.

Tan et al. "Microwave-Assisted C-H Bond Activation: A Rapid Entry Into Functionalized Heterocycles", Organic Letters, vol. 5 No. 12, pp. 2131-2134, 2003.

* cited by examiner

PROCESS FOR PRODUCING PHOSPHONIUM BORATE COMPOUND, NOVEL PHOSPHONIUM BORATE COMPOUND, AND METHOD OF USING THE SAME

FIELD OF THE INVENTION

The present invention relates to a process for producing a phosphonium borate compound, a novel phosphonium borate compound, and use of the compound.

BACKGROUND OF THE INVENTION

Transition metal complexes having alkylphosphine compounds as ligands are very important catalysts in carbon-carbon bond forming reactions such as Suzuki-Miyaura reaction, carbon-nitrogen bond forming reactions such as Buchwald-Hartwig amination, and carbon-oxygen bond forming reactions such as ether synthesis (see Nonpatent Document 1). As an example, bis(tri-tert-butylphosphine) palladium (0) is used.

Many of the transition metal complexes having alkylphosphine ligands are very expensive, and the industrial availability thereof is low. Further, synthesis of the transition metal complexes having alkylphosphine ligands is difficult because the raw-material alkylphosphine compounds are generally extremely susceptible to air oxidation and possess combustibility.

For such reasons, the alkylphosphine compounds are used together with transition metals, salts thereof, oxides thereof or complexes thereof in the reaction system, in place of the isolated transition metal complexes having alkylphosphine ligands (see Nonpatent Documents 1 and 3). For example, di-tert-butylmethylphosphine, tri-tert-butylphosphine or tricyclohexylphosphine is used together with palladium (II) acetate or tris(dibenzylideneacetone)dipalladium (0) in the reaction system.

However, many of the alkylphosphine compounds are extremely susceptible to air oxidation and possess combustibility, and therefore are difficult to handle.

To improve the susceptibility to air oxidation, alkylphosphonium tetrafluoroborates, quaternary salts of alkylphosphines and boron compounds, have been studied. Examples of the alkylphosphonium tetrafluoroborates include:

(1) triethylphosphonium tetrafluoroborate (see Nonpatent Document 2);

(2) tricyclohexylphosphonium tetrafluoroborate (see Nonpatent Document 4);

(3) di-tert-butylmethylphosphonium tetrafluoroborate (see Nonpatent Document 3);

(4) tri-n-butylphosphonium tetrafluoroborate (see Nonpatent Document 5); and (5) tri-tert-butylphosphonium tetrafluoroborate (see Nonpatent Document 4).

These compounds are produced from alkylphosphine compounds and fluoroboric acid (see Nonpatent Document 5).

As known in the art, the above compounds are used together with transition metals, salts thereof, oxides thereof or complexes thereof in the carbon-carbon bond forming reactions such as Suzuki-Miyaura reaction (see Nonpatent Documents 3 and 5). For example, di-tert-butylmethylphosphonium tetrafluoroborate or tri-tert-butylphosphonium tetrafluoroborate is used together with palladium (II) acetate, tris (dibenzylideneacetone)dipalladium (0) or bis(benzonitrile)dichloropalladium (II) in the reaction system.

Fluoroboric acid used as raw material in the production of the compounds (1) to (5) are corrosive and penetrate into the skin upon contact, and must be handled carefully. Furthermore, fluoroboric acid has acidity to corrode production utility made of stainless steel, and when hydrofluoric acid is liberated, it will corrode production utility made of glass. Therefore, the actual use of the above compounds in the production causes problems.

Alkylphosphonium tetraarylborate compounds are also developed, and the following compounds are known:

(6) triethylphosphonium tetraphenylborate (see Patent Document 1);

(7) tri-n-butylphosphonium tetraphenylborate (see Patent Document 1 and Nonpatent Document 6);

(8) tricyclohexylphosphonium tetraphenylborate (see Nonpatent Documents 4 and 7); and (9) tri-tert-butylphosphonium tetraphenylborate (see Nonpatent Documents 4 and 7).

Nonpatent Documents 4, 6 and 7 describe the production of the alkylphosphonium tetraarylborate compounds. Specifically, the documents describe the following production processes (10) to (12).

(10) Tricyclohexylphosphine is reacted with fluoroboric acid to synthesize tricyclohexylphosphonium tetrafluoroborate, which is reacted with sodium tetraphenylborate to produce tricyclohexylphosphonium tetraphenylborate (75% yield). A similar process is described in which tri-tert-butylphosphine is used as starting material to produce tri-tert-butylphosphonium tetraphenylborate (71% yield) (see Nonpatent Document 4).

(11) Tri-tert-butylphosphine is reacted with 1,1,1,3,3,3-hexafluoro-2-propanol and with sodium tetraphenylborate to produce tri-tert-butylphosphonium tetraphenylborate (77% yield). A similar process is described in which tricyclohexylphosphine is used as starting material to produce tricyclohexylphosphonium tetraphenylborate (77% yield) (see Nonpatent Document 7).

(12) Tri-n-butylphosphine is reacted with hydrochloric acid in the presence of sodium tetraphenylborate to produce tri-n-butylphosphonium tetraphenylborate (53% yield) (see Nonpatent Document 6).

The four compounds (6) to (9) are the only compounds known as the alkylphosphonium tetraarylborate compounds, and the three processes (10) to (12) are the only known processes for producing them.

The processes (10) (Nonpatent Document 4) use fluoroboric acid and consequently have handling problems and problems of corrosion of production facility, and are not suited for industrial production.

The processes (11) (Nonpatent Document 7) use 1,1,1,3,3,3-hexafluoro-2-propanol which is expensive, and are not suited for industrial production. More inexpensive processes are desirable.

In the process (12) (Nonpatent Document 6) in which tri-n-butylphosphine is reacted with hydrochloric acid in the presence of sodium tetraphenylborate, the yield of tri-n-butylphosphonium tetraphenylborate is low (53% in terms of tri-n-butylphosphine). The reason for the low yield is not clear but is probably that a side reaction takes place between the reaction product of sodium tetraphenylborate with hydrochloric acid, and tri-n-butylphosphine.

The documents recited above do not describe that the carbon-carbon bond forming reactions, carbon-nitrogen bond forming reactions and carbon-oxygen bond forming reactions wherein the transition metal complexes having phosphine ligands produce catalytic effects, may be catalyzed by phosphonium tetraarylborate compounds together with transition metals, salts thereof, oxides thereof or complexes thereof in place of the transition metal complexes having phosphine ligands.

Thus, there is a need for the development of alkylphosphine derivatives that are producible without special reaction equipment and by simple operations, and have good handling properties.

Patent Document 1: JP-A-S62-149721 (pp. 2 and 3) Nonpatent Document 1: Journal of American Chemical Society (U.S.A.) (2000, vol. 122, No. 17, pp. 4020-4028)

Nonpatent Document 2: Catalog of Strem Chemicals, Inc.

Nonpatent Document 3: Journal of American Chemical Society (U.S.A.) (2002, vol. 124, No. 46, pp. 13662-13663)

Nonpatent Document 4: Journal of American Chemical Society (U.S.A.) (1991, vol. 113, No. 3, pp. 875-883)

Nonpatent Document 5: Organic Letters (U.S.A.) (2001, vol. 3, No. 26, pp. 4295-4298)

Nonpatent Document 6: Organometallics (U.S.A.) (1999, vol. 18, No. 20, pp. 3981-3990)

Nonpatent Document 7: Journal of American Chemical Society (U.S.A.) (1997, vol. 119, No. 16, pp. 3716-3731)

PROBLEMS TO BE SOLVED BY THE INVENTION

It is an object of the present invention to provide a novel process whereby a phosphonium borate compound is produced safely on an industrial scale, by simple reaction operations and in a high yield. It is another object of the invention to provide a novel phosphonium borate compound that is easily handled. It is a further object of the invention to provide a novel use of the phosphonium borate compound in combination with a transition metal, salt thereof, oxide thereof or complex thereof in the carbon-carbon bond forming reactions, carbon-nitrogen bond forming reactions and carbon-oxygen bond forming reactions wherein a transition metal complex having a phosphine ligand produces catalytic effects, wherein the phosphonium borate compound in combination with the transition metal, salt thereof, oxide thereof or complex thereof is used in place of the transition metal complex having a phosphine ligand.

SUMMARY OF THE INVENTION

The present inventors studied diligently to achieve the above objects, and they have found that a phosphonium borate compound can be produced safely, by simple reaction operations, and in a high yield by reacting a phosphine (II) with hydrochloric or sulfuric acid, and reacting the reaction product with a tetraarylborate compound (IV).

The inventors have also found a novel phosphonium borate compound which is highly resistance to oxidation as compared to alkylphosphine compounds. It has been also found that the phosphonium borate compound in combination with a transition metal, salt thereof, oxide thereof or complex thereof can be used in the carbon-carbon bond forming reactions, carbon-nitrogen bond forming reactions and carbon-oxygen bond forming reactions wherein a transition metal complex having a phosphine ligand produces catalytic effects, wherein the phosphonium borate compound in combination with the transition metal, salt thereof, oxide thereof or complex thereof is used in place of the transition metal complex having a phosphine ligand.

In a first aspect of the present invention, there is provided a process for producing a phosphonium borate compound, which comprises:

reacting a phosphine with HCl to produce a phosphine hydrochloride, the phosphine being represented by Formula (II):

$(R^1)(R^2)(R^3)P$ (II)

wherein $R^1$ is a primary alkyl group of 1 to 20 carbon atoms, a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine hydrochloride being represented by Formula (III):

$(R^1)(R^2)(R^3)PH.Cl$ (III)

wherein $R^1$, $R^2$ and $R^3$ are as defined in Formula (II);

and reacting the phosphine hydrochloride with a tetraarylborate compound represented by Formula (IV):

$M.BAr_4$ (IV)

wherein M is lithium, sodium, potassium, magnesium halide or calcium halide, and Ar is an aryl group of 6 to 20 carbon atoms;

the phosphonium borate compound being represented by Formula (I):

$(R^1)(R^2)(R^3)PH.BAr_4$ (I)

wherein $R^1$, $R^2$ and $R^3$ are as defined in Formula (II), and Ar is as defined in Formula (IV).

In a second aspect of the present invention, there is provided a process for producing a phosphonium borate compound, which comprises:

reacting a phosphine with $H_2SO_4$ to produce a phosphine sulfate, the phosphine being represented by Formula (II):

$(R^1)(R^2)(R^3)P$ (II)

wherein $R^1$ is a primary alkyl group of 1 to 20 carbon atoms, a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine sulfate being represented by Formula (V):

$$[(R^1)(R^2)(R^3)PH]_{(2-n)} \cdot H_n SO_4 \quad (V)$$

wherein $R^1$, $R^2$ and $R^3$ are as defined in Formula (II), and n is an integer of 0 or 1;

and reacting the phosphine sulfate with a tetraarylborate compound represented by Formula (IV):

$$M \cdot BAr_4 \quad (IV)$$

wherein M is lithium, sodium, potassium, magnesium halide or calcium halide, and Ar is an aryl group of 6 to 20 carbon atoms;

the phosphonium borate compound being represented by Formula (I) described above.

In a third aspect of the present invention, there is provided a novel phosphonium borate compound represented by Formula (I):

$$(R^1)(R^2)(R^3)PH \cdot BAr_4 \quad (I)$$

wherein $R^1$ is a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms;

$R^1$, $R^2$ and $R^3$ may be the same or different from one another;

Ar is an aryl group of 6 to 20 carbon atoms;

$R^1$, $R^2$ and $R^3$ cannot be tert-butyl groups simultaneously and Ar cannot be phenyl group at the same time; and $R^1$, $R^2$ and $R^3$ cannot be cyclohexyl groups simultaneously and Ar cannot be phenyl group at the same time.

In a fourth aspect of the present invention, there is provided use of a phosphonium borate compound in combination with a transition metal, transition metal salt, transition metal oxide or transition metal complex in carbon-carbon bond forming reactions, carbon-nitrogen bond forming reactions and carbon-oxygen bond forming reactions wherein a transition metal complex having a phosphine ligand produces catalytic effects, wherein the phosphonium borate compound in combination with the transition metal, transition metal salt, transition metal oxide or transition metal complex is used in place of the transition metal complex having a phosphine ligand, the phosphonium borate compound being represented by Formula (I):

$$(R^1)(R^2)(R^3)PH \cdot BAr_4 \quad (I)$$

wherein $R^1$ is a primary alkyl group of 1 to 20 carbon atoms, a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms;

$R^1$, $R^2$ and $R^3$ may be the same or different from one another;

and

Ar is an aryl group of 6 to 20 carbon atoms.

The process according to the present invention can produce a phosphonium borate compound safely, by simple reaction operations and in a high yield. In the production process, the specific phosphine hydrochloride or phosphine sulfate is reacted with the specific tetraarylborate compound, and consequently the novel phosphonium borate compound is produced safely, by simple reaction operations and in a high yield. The phosphonium borate compound provided in the invention is novel. The phosphonium borate compound in combination with a transition metal, salt thereof, oxide thereof or complex thereof can be used in the carbon-carbon bond forming reactions, carbon-nitrogen bond forming reactions and carbon-oxygen bond forming reactions wherein a transition metal complex having a phosphine ligand produces catalytic effects, wherein the phosphonium borate compound in combination with the transition metal, salt thereof, oxide thereof or complex thereof is used in place of the transition metal complex having a phosphine ligand.

DETAILED DESCRIPTION OF THE INVENTION

The process for producing a phosphonium borate compound, novel phosphonium borate compound, and use of the compound will be described in detail hereinbelow.

Process for Producing Phosphonium Borate Compound

The process for producing a phosphonium borate compound will be described with reference to first and second production processes.

<First Production Process>

The first process for producing a phosphonium borate compound includes:

reacting a phosphine with HCl to produce a phosphine hydrochloride, the phosphine being represented by Formula (II):

$$(R^1)(R^2)(R^3)P \quad (II)$$

wherein $R^1$ is a primary alkyl group of 1 to 20 carbon atoms, a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine hydrochloride being represented by Formula (III):

$$(R^1)(R^2)(R^3)PH \cdot Cl \qquad (III)$$

wherein $R^1$, $R^2$ and $R^3$ are as defined in Formula (II);

and reacting the phosphine hydrochloride with a tetraarylborate compound represented by Formula (IV):

$$M \cdot BAr_4 \qquad (IV)$$

wherein M is lithium, sodium, potassium, magnesium halide or calcium halide, and Ar is an aryl group of 6 to 20 carbon atoms;

the phosphonium borate compound being represented by Formula (I):

$$(R^1)(R^2)(R^3)PH \cdot BAr_4 \qquad (I)$$

wherein $R^1$, $R^2$ and $R^3$ are as defined in Formula (II), and Ar is as defined in Formula (IV).

Specifically, the first process for producing a phosphonium borate compound (I) includes:

a 1st step in which the phosphine (II) is reacted with HCl to give the phosphine hydrochloride (III); and a 2nd step in which the compound (III) is reacted with the tetraarylborate compound (IV) to produce the phosphonium borate compound (I), as illustrated in the reaction formula below:

[Chem. 1]

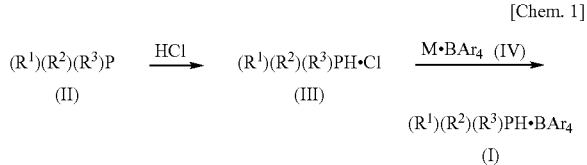

The first production process can produce the phosphonium borate compound (I) in a high yield. The reason for this effect is not clear, but is probably that a side reaction that takes place when the compound (II), HCl and the compound (IV) are added at the same time can be substantially avoided.

The first process for producing a phosphonium borate compound (I) will be described below with reference to an embodiment 1 for producing the trialkylphosphonium tetraphenylborate and an embodiment 2 for producing the novel phosphonium borate compound.

Embodiment 1

[1st Step]

In the 1st step, a trialkylphosphine (II) and HCl are reacted under predetermined conditions. These components will be described below.

The trialkylphosphine (II) used as a raw material in the production process is represented by Formula (II):

$$(R^1)(R^2)(R^3)P \qquad (II)$$

wherein $R^1$, $R^2$ and $R^3$ are ethyl, n-butyl, tert-butyl or cyclohexyl groups, and are the same. Examples of the trialkylphosphines (II) include triethylphosphine, tri-n-butylphosphine, tri-tert-butylphosphine and tricyclohexylphosphine.

The trialkylphosphines (II) of Formula (II) may be produced by or according to known methods.

Examples of such methods include, but are not limited to, reaction of phosphinas halides and organo Grignard reagents, reaction of phosphinas halides and organolithium reagents, and reaction of phosphines and olefins. The trialkylphosphines (II) synthesized by the above reactions may be purified prior to use, or may be used without purification.

The trialkylphosphines (II) may be used in an undiluted form, or may be diluted with a solvent. Herein, the diluting solvents include solvents contained in the unpurified trialkylphosphines (II). The unpurified trialkylphosphines (II) may be further diluted with a solvent.

The solvents are not particularly limited as long as they can dissolve reaction substrates and are inert to the reaction substrates. Examples thereof include water; alcohol solvents such as methanol, ethanol and octanol; aliphatic hydrocarbon solvents such as hexane, heptane and isooctane; aromatic hydrocarbon solvents such as benzene, toluene and xylene; ether solvents such as tetrahydrofuran and dibutyl ether; halogenated hydrocarbon solvents such as chloroform and tetrachloromethane; dimethylsulfoxide and dimethylformamide. The solvents may be used singly or in combination of two or more kinds.

HCl used in the production process may be hydrochloric acid or hydrogen chloride gas. The HCl concentration in hydrochloric acid is not particularly limited, and is desirably in the range of 0.1 to 37% by weight, preferably 10 to 37% by weight.

The 1st step involving the above raw materials is performed in a reactor purged with an inert gas such as nitrogen or argon. The addition sequence of the raw materials is not particularly limited. For example, HCl may be added to the trialkylphosphine (II), or the trialkylphosphine (II) may be added to HCl. When HCl is hydrochloric acid, the addition method is not particularly limited, and it may be added all at once or may be added dropwise intermittently or continuously. The hydrogen chloride gas may be easily added by being blown into the trialkylphosphine (II).

In the 1st step, the desirable HCl requirement, desirable temperature for smooth reaction, and desirable time to complete the reaction vary depending on the type of the trialkylphosphine (II) used, and are selected appropriately.

The HCl amount varies depending on the type of the trialkylphosphine (II), and is desirably in the range of 0.5 to 5 mol, preferably 0.8 to 1.6 mol per mol of phosphine. The HCl amount in this range enables the production of the trialkylphosphonium tetraphenylborate (I) in a high yield.

The reaction of HCl is desirably carried out while the solution is at −20 to 150° C., preferably 0 to 80° C. and is continuously stirred for up to 24 hours, preferably 30 minutes to 5 hours at the temperature. The reaction under these conditions enables the production of the trialkylphosphonium tetraphenylborate (I) in a high yield.

The completion of the reaction in the 1st step may be determined by confirming the absence of unreacted trialkylphosphine (II). Specifically, the organic phase is analyzed by gas chromatography or the like to determine the trialkylphosphine (II) in the organic phase. When the analysis confirms substantial absence of the remaining trialkylphosphine (II), the reaction is terminated. When the trialkylphosphine (II) is still present in the organic phase, the reaction is preferably continued.

The reaction solution takes various forms depending on the solvent used. For example, the solution may contain crystals of trialkylphosphine hydrochloride (III) (described later), may be a uniform solution or a suspension, or may be a two-phase system consisting of an aqueous phase and an organic phase. In the case of the two-phase system consisting of an aqueous phase and an organic phase, the system is subjected to separation. In the case of other solution forms, separation may be performed as required by adding water, toluene, n-hexane, n-heptane or the like. The aqueous phase resulting from the separation may be washed with toluene, n-hexane, n-heptane or the like as required.

The aqueous phase obtained by the reaction of the 1st step contains a reaction intermediate dissolved therein that is assumed to be a trialkylphosphine hydrochloride represented by Formula (III):

$$(R^1)(R^2)(R^3)PH.Cl \quad (III)$$

wherein $R^1$, $R^2$ and $R^3$ are as defined in Formula (II).

The formation of the trialkylphosphine hydrochloride (III) may be confirmed by, for example, a nuclear magnetic resonance spectrum ($^1$H-NMR).

[2nd Step]

The reaction intermediate trialkylphosphine hydrochloride (III) obtained in the 1st step is reacted with a tetraphenylborate compound (IV) under predetermined conditions to produce a trialkylphosphonium tetraphenylborate represented by Formula (I):

$$(R^1)(R^2)(R^3)PH.BAr_4 \quad (I)$$

wherein $R^1$, $R^2$ and $R^3$ are ethyl, n-butyl, tert-butyl or cyclohexyl groups, and are the same; and Ar is phenyl group.

The tetraphenylborate compound (IV) used in the 2nd step is represented by Formula (IV):

$$M.BAr_4 \quad (IV)$$

wherein M is lithium, sodium, potassium, magnesium halide or calcium halide, and Ar is phenyl group.

In Formula (IV), M may be a magnesium halide or a calcium halide, with examples including magnesium fluoride, magnesium chloride, magnesium bromide, magnesium iodide, calcium fluoride, calcium chloride, calcium bromide and calcium iodide.

Specific examples of the tetraphenylborate compounds of Formula (IV) include lithium tetraphenylborate, sodium tetraphenylborate, potassium tetraphenylborate, tetraphenylborate magnesium fluoride, tetraphenylborate magnesium chloride, tetraphenylborate magnesium bromide, tetraphenylborate magnesium iodide, tetraphenylborate calcium fluoride, tetraphenylborate calcium chloride, tetraphenylborate calcium bromide and tetraphenylborate calcium iodide. The tetraphenylborate compounds (IV) may be used singly or in combination of two or more kinds.

Of the tetraphenylborate compounds (IV), sodium tetraphenylborate is particularly preferred. Sodium tetraphenylborate is preferable because of easy synthesis by known methods.

The tetraphenylborate compounds (IV) may be used in an undiluted form, or may be diluted with a solvent.

The solvent may be appropriately selected from the solvents used for dissolving the trialkylphosphines (II). The solvents may be used singly or in combination of two or more kinds.

Specifically, the 2nd step involving the above raw materials is performed by mixing the aqueous solution of the reaction intermediate assumed to be the trialkylphosphine hydrochloride (III), with the tetraphenylborate compound (IV) thereby to react the compound (III) with the compound (IV) under predetermined conditions.

The addition sequence of the aqueous solution obtained in the 1st step and the tetraphenylborate compound (IV) is not particularly limited. The addition method is not particularly limited, and the material may be added all at once or may be added dropwise intermittently or continuously.

In the 2nd step, the desirable requirement of the tetraphenylborate compound (IV), desirable temperature for smooth reaction, and desirable time to complete the reaction vary depending on the type of the raw material compound trialkylphosphine (II) used, amount of hydrogen chloride gas or hydrochloric acid, and type of the tetraphenylborate compound (IV), and are selected appropriately.

The amount of the tetraphenylborate compound (IV) varies depending on the type of the trialkylphosphine (II) used in the 1st step, and is desirably in the range of 0.55 to 5.5 mol, preferably 0.85 to 1.65mol per mol of phosphine. Particularly preferably, the compound is used in an amount of at least 1 mol per mol of HCl used. The amount of the tetraphenylborate compound (IV) in this range enables the production of the trialkylphosphonium tetraphenylborate (I) in a high yield.

The reaction of the tetraphenylborate compound (IV) is desirably carried out while the reaction solution is at −20 to 150° C., preferably 0 to 80° C. and is continuously stirred for up to 24 hours, preferably 1 to 5 hours at the temperature. The reaction under these conditions enables the production of the trialkylphosphonium tetraphenylborate (I) in a high yield.

After the completion of the reaction, purification such as recrystallization or column chromatography is performed, and consequently the objective trialkylphosphonium tetraphenylborate (I) of Formula (I) can be obtained with high purity:

$$(R^1)(R^2)(R^3)PH.BAr_4 \quad (I)$$

wherein $R^1$, $R^2$ and $R^3$ are ethyl, n-butyl, tert-butyl or cyclohexyl groups, and are the same; and Ar is phenyl group.

According to the embodiment 1, the trialkylphosphonium tetraphenylborate (I) can be obtained in a high yield, specifically in a yield of about 87 to 93 mol % in terms of trialkylphosphine (II).

Examples of the trialkylphosphonium tetraphenylborates (I) of Formula (I) produced according to the embodiment 1 of the first production process include triethylphosphonium tetraphenylborate, tri-n-butylphosphonium tetraphenylborate, tri-tert-butylphosphonium tetraphenylborate and tricyclohexylphosphonium tetraphenylborate.

Next, the embodiment 2 for producing the novel phosphonium borate compound will be described.

Embodiment 2

[1st Step]

In the 1st step, a phosphine (II) and HCl are reacted under predetermined conditions. These components will be described below.

The phosphine (II) used as a raw material in the production process is represented by Formula (II):

$$(R^1)(R^2)(R^3)P \quad (II)$$

In Formula (II), $R^1$ is as described below.

$R^1$ may be a secondary alkyl group, desirably a secondary alkyl group having 3 to 20, preferably 3 to 11 carbon atoms.

The secondary alkyl groups include isopropyl, sec-butyl, 2-pentyl, 3-pentyl, 2-hexyl and 3-hexyl.

$R^1$ may be a tertiary alkyl group, desirably a tertiary alkyl group having 4 to 20, preferably 4 to 11 carbon atoms. The tertiary alkyl groups include tert-butyl, tert-amyl, 1,1-dimethylbutyl, 3-methyl-3-pentyl and 1,1,2-trimethylpropyl.

$R^1$ may be a cycloalkyl group, desirably a cycloalkyl group having 3 to 20, preferably 3 to 11 carbon atoms. The cycloalkyl groups include cyclopropyl, cyclopentyl, cyclohexyl, 1-methylcyclohexyl, 2-methylcyclohexyl, 1-adamantyl, 2-methyl-1-adamantyl, 2-adamantyl, 1-methyl-2-adamantyl and 2-methyl-2-adamantyl. $R^1$ is not limited to the groups described above.

In Formula (II), $R^2$ is as described below.

$R^2$ may be a primary alkyl group, desirably a primary alkyl group having 1 to 20, preferably 1 to 8 carbon atoms. The primary alkyl groups include methyl, ethyl, n-propyl, n-butyl, isobutyl, n-pentyl, isopentyl, n-hexyl, 2-methyl-1-pentyl, 2,2-diethyl-1-ethyl, n-heptyl and n-octyl.

$R^2$ may be a secondary alkyl group, desirably a secondary alkyl group having 3 to 20, preferably 3 to 11 carbon atoms. The secondary alkyl groups include isopropyl, sec-butyl, 2-pentyl, 3-pentyl, 2-hexyl and 3-hexyl.

$R^2$ may be a tertiary alkyl group, desirably a tertiary alkyl group having 4 to 20, preferably 4 to 11 carbon atoms. The tertiary alkyl groups include tert-butyl, tert-amyl, 1,1-dimethylbutyl, 3-methyl-3-pentyl and 1,1,2-trimethylpropyl.

$R^2$ may be a cycloalkyl group, desirably a cycloalkyl group having 3 to 20, preferably 3 to 11 carbon atoms. The cycloalkyl groups include cyclopropyl, cyclopentyl, cyclohexyl, 1-methylcyclohexyl, 2-methylcyclohexyl, 1-adamantyl, 2-methyl-1-adamantyl, 2-adamantyl, 1-methyl-2-adamantyl and 2-methyl-2-adamantyl.

$R^2$ may be an aralkyl group, desirably an aralkyl group having 7 to 20, preferably 7 to 12 carbon atoms. The aralkyl groups include benzyl, 1-phenylethyl, 2-phenylethyl, 2-ethenylbenzyl, 3-ethenylbenzyl, 4-ethenylbenzyl, 4-(2-ethenylphenyl)butyl, 4-(3-ethenylphenyl)butyl and 4-(4-ethenylphenyl)butyl.

$R^2$ may desirably be an allyl group having 3 to 20, preferably 3 to 8 carbon atoms. The allyl groups include allyl and 2-octenyl. $R^2$ is not limited to the groups described above.

In Formula (II), $R^3$ is as described below.

$R^3$ may be a primary alkyl group, desirably a primary alkyl group having 1 to 20, preferably 1 to 8 carbon atoms. The primary alkyl groups include methyl, ethyl, n-propyl, n-butyl, isobutyl, n-pentyl, isopentyl, n-hexyl, 2-methyl-1-pentyl, 2,2-diethyl-1-ethyl, n-heptyl and n-octyl.

$R^3$ may be a secondary alkyl group, desirably a secondary alkyl group having 3 to 20, preferably 3 to 11 carbon atoms. The secondary alkyl groups include isopropyl, sec-butyl, 2-pentyl, 3-pentyl, 2-hexyl and 3-hexyl.

$R^3$ may be a tertiary alkyl group, desirably a tertiary alkyl group having 4 to 20, preferably 4 to 11 carbon atoms. The tertiary alkyl groups include tert-butyl, tert-amyl, 1,1-dimethylbutyl, 3-methyl-3-pentyl and 1,1,2-trimethylpropyl.

$R^3$ may be a cycloalkyl group, desirably a cycloalkyl group having 3 to 20, preferably 3 to 11 carbon atoms. The cycloalkyl groups include cyclopropyl, cyclopentyl, cyclohexyl, 1-methylcyclohexyl, 2-methylcyclohexyl, 1-adamantyl, 2-methyl-1-adamantyl, 2-adamantyl, 1-methyl-2-adamantyl and 2-methyl-2-adamantyl.

$R^3$ may be an aryl group, desirably an aryl group having 6 to 30, preferably 6 to 22 carbon atoms. The aryl groups include phenyl, ortho-tolyl, meta-tolyl, para-tolyl, 2,3-xylyl, 2,4-xylyl, 2,5-xylyl, 2,6-xylyl, 3,4-xylyl, 3,5-xylyl, mesityl, 2-tert-butylphenyl, 3-tert-butylphenyl, 4-tert-butylphenyl, 2-ethenylphenyl, 3-ethenylphenyl, 4-ethenylphenyl, 2-biphenylyl, 3-biphenylyl, 4-biphenylyl, 1-naphthyl, 2-naphthyl, 1,1'-binaphthalene-2-yl, 2-methoxyphenyl, 3-methoxyphenyl, 4-methoxyphenyl, 2-tert-butoxyphenyl, 3-tert-butoxyphenyl, 4-tert-butoxyphenyl, 2-dimethylaminophenyl, 3-dimethylaminophenyl, 4-dimethylaminophenyl, 2'-dimethylamino-2-biphenylyl, 8-dimethylamino-1-naphthyl and 2'-dimethylamino-1,1'-binaphthalene-2-yl.

$R^3$ may be an aralkyl group, desirably an aralkyl group having 7 to 20, preferably 7 to 12-carbon atoms. The aralkyl groups include benzyl, 1-phenylethyl, 2-phenylethyl, 2-ethenylbenzyl, 3-ethenylbenzyl, 4-ethenylbenzyl, 4-(2-ethenylphenyl)butyl, 4-(3-ethenylphenyl)butyl and 4-(4-ethenylphenyl)butyl.

$R^3$ may be an alkenyl group, desirably an alkenyl group having 2 to 20, preferably 2 to 8 carbon atoms. The alkenyl groups include vinyl, methallyl and 1-octenyl.

$R^3$ may be an alkynyl group, desirably an alkynyl group having 2 to 20, preferably 2 to 8 carbon atoms. The alkynyl groups include ethynyl, 1-propynyl and 1-octynyl.

$R^3$ may desirably be an allyl group having 3 to 20, preferably 3 to 8 carbon atoms. The allyl groups include allyl and 2-octenyl. $R^3$ is not limited to the groups described above.

As long as $R^1$, $R^2$ and $R^3$ are selected from the above groups, they may have an arbitrary combination in terms of carbon atom numbers.

Specific examples of the phosphines (II) represented by Formula (II) are shown in Tables 1-1 to 4-2 which will be presented later.

Specifically, preferred phosphines (II) include di-tert-butylmethylphosphine, tri-tert-butylphosphine, di-tert-butylethylphosphine, n-butyl-di-tert-butylphosphine, n-butyl-dicyclohexylphosphine, sec-butyl-di-tert-butylphosphine, cyclohexyl-di-tert-butylphosphine, di-tert-butyl-n-octylphosphine, di-tert-butylphenylphosphine, 2-biphenylyl-di-tert-butylphosphine, di-tert-butyl-1-naphthylphosphine, benzyl-di-tert-butylphosphine, di-tert-butyl(4-ethenylbenzyl)phosphine, di-tert-butylvinylphosphine, allyl-di-tert-butylphosphine, tricyclopentylphosphine, tricyclohexylphosphine and triisopropylphosphine. Di-tert-butylmethylphosphine, tri-tert-butylphosphine, tricyclohexylphosphine and triisopropylphosphine are more preferable. These phosphines (II) are preferable because of easy availability of raw materials.

The phosphine compounds of Formula (II) may be produced by or according to known methods.

Examples of such methods include, but are not limited to, reaction of phosphinas halides and organo Grignard reagents, reaction of phosphinas halides and organolithium reagents, and reaction of phosphines and olefins. The phosphines (II) synthesized by the above reactions may be purified prior to use, or may be used without purification.

The phosphines (II) may be used in an undiluted form, or may be diluted with a solvent. Herein, the diluting solvents include solvents contained in the unpurified phosphines (II). The unpurified phosphines (II) may be further diluted with a solvent.

The solvents are not particularly limited as long as they can dissolve reaction substrates and are inert to the reaction substrates. Examples thereof include water; alcohol solvents such as methanol, ethanol and octanol; aliphatic hydrocarbon solvents such as hexane, heptane and isooctane; aromatic hydrocarbon solvents such as benzene, toluene and xylene; ether solvents such as tetrahydrofuran and dibutyl ether; halogenated hydrocarbon solvents such as chloroform and tetrachloromethane; dimethylsulfoxide and dimethylformamide. The solvents may be used singly or in combination of two or more kinds.

HCl used in the production process may be hydrochloric acid or hydrogen chloride gas. The HCl concentration in hydrochloric acid is not particularly limited, and is desirably in the range of 0.1 to 37% by weight, preferably 10 to 37% by weight.

The 1st step involving the above raw materials is performed in a reactor purged with an inert gas such as nitrogen or argon. The addition sequence of the raw materials is not particularly limited. For example, HCl may be added to the phosphine (II), or the phosphine (II) may be added to HCl. When HCl is hydrochloric acid, the addition method is not particularly limited, and it may be added all at once or may be added dropwise intermittently or continuously. The hydrogen chloride gas may be easily added by being blown into the phosphine (II).

In the 1st step, the desirable HCl requirement, desirable temperature for smooth reaction, and desirable time to complete the reaction vary depending on the type of the phosphine (II) used, and are selected appropriately.

The HCl amount varies depending on the type of the phosphine (II), and is desirably in the range of 0.5 to 5 mol, preferably 0.8 to 1.6 mol per mol of phosphine. The HCl amount in this range enables the production of the phosphonium borate compound (I) in a high yield.

The reaction of HCl is desirably carried out while the solution is at −20 to 150° C., preferably 0 to 80° C. and is continuously stirred for up to 24 hours, preferably 30 minutes to 5 hours at the temperature. The reaction under these conditions enables the production of the phosphonium borate compound (I) in a high yield.

The completion of the reaction in the 1st step may be determined by confirming the absence of unreacted phosphine (II). Specifically, the organic phase is analyzed by gas chromatography or the like to determine the phosphine (II) in the organic phase. When the analysis confirms substantial absence of the remaining phosphine (II), the reaction is terminated. When the phosphine is still present in the organic phase, the reaction is preferably continued.

The reaction solution takes various forms depending on the solvent used. For example, the solution may contain crystals of phosphine hydrochloride (III) (described later), may be a uniform solution or a suspension, or may be a two-phase system consisting of an aqueous phase and an organic phase. In the case of the two-phase system consisting of an aqueous phase and an organic phase, the phosphine hydrochloride (III) passes into the aqueous phase and therefore the aqueous phase is subjected to separation. In the case of other solution forms, separation may be performed as required by adding water, toluene, n-hexane, n-heptane or the like. The aqueous phase resulting from the separation may be washed with toluene, n-hexane, n-heptane or the like as required.

The aqueous phase obtained by the reaction of the 1st step contains a reaction intermediate dissolved therein that is assumed to be a phosphine hydrochloride (III) represented by Formula (III):

$$(R^1)(R^2)(R^3)PH.Cl \qquad (III)$$

wherein $R^1$, $R^2$ and $R^3$ are as defined in Formula (II).

The formation of the phosphine hydrochloride (III) may be confirmed by, for example, a nuclear magnetic resonance spectrum ($^1$H-NMR)

[2nd Step]

The reaction intermediate that is assumed to be the phosphine hydrochloride (III) obtained in the 1st step is reacted with a tetraarylborate compound (IV) under predetermined conditions to produce a novel phosphonium borate compound (I) of the present invention.

The tetraarylborate compound (IV) used in the 2nd step is represented by Formula (IV):

In Formula (IV), M may be a magnesium halide or a calcium halide, with examples including magnesium fluoride, magnesium chloride, magnesium bromide, magnesium iodide, calcium fluoride, calcium chloride, calcium bromide and calcium iodide.

Ar is desirably an aryl group having 6 to 20, preferably 6 to 10 carbon atoms. Specific examples include phenyl, ortho-tolyl, meta-tolyl, para-tolyl, 2,3-xylyl, 2,4-xylyl, 2,5-xylyl, 2,6-xylyl, 3,4-xylyl, 3,5-xylyl, mesityl, 2-tert-butylphenyl, 3-tert-butylphenyl, 4-tert-butylphenyl, 2-methoxyphenyl, 3-methoxyphenyl, 4-methoxyphenyl, 2-tert-butoxyphenyl, 3-tert-butoxyphenyl and 4-tert-butoxyphenyl.

The tetraarylborate compound (IV) is selected appropriately such that in the phosphonium borate compound (I) of Formula (I), $R^1$, $R^2$ and $R^3$ are not tert-butyl groups simultaneously and Ar is not phenyl group at the same time, and $R^1$, $R^2$ and $R^3$ are not cyclohexyl groups simultaneously and Ar is not phenyl group at the same time.

Specific examples of the tetraarylborate compounds represented by Formula (IV) are shown in Tables 5 to 10 which will be presented later. These tetraarylborate compounds may be used singly or in combination of two or more kinds.

Of the tetraarylborate compounds (IV), sodium tetraphenylborate and sodium tetra-para-tolylborate are particularly preferable. The tetraarylborate compounds (IV) are preferable because of easy synthesis by known methods.

The tetraarylborate compounds (IV) may be used in an undiluted form, or may be diluted with a solvent.

The solvent may be appropriately selected from the solvents used for dissolving the phosphines (II). The solvents may be used singly or in combination of two or more kinds.

Specifically, the 2nd step involving the above raw materials is performed by mixing the aqueous solution of the reaction intermediate assumed to be the phosphine hydrochloride (III), with the tetraarylborate compound (IV) thereby to react the compound (III) with the compound (IV) under predetermined conditions.

The addition sequence of the aqueous solution obtained in the 1st step and the tetraarylborate compound (IV) is not particularly limited. The addition method is not particularly limited, and the material may be added all at once or may be added dropwise intermittently or continuously.

In the 2nd step, the desirable requirement of the tetraarylborate compound (IV), desirable temperature for smooth reaction, and desirable time to complete the reaction vary depending on the type of the raw material compound phosphine (II) used, amount of hydrogen chloride gas or hydrochloric acid, and type of the tetraarylborate compound (IV), and are selected appropriately.

The amount of the tetraarylborate compound (IV) varies depending on the type of the phosphine (II) used in the 1st step, and is desirably in the range of 0.55 to 5.5 mol, preferably 0.85 to 1.65 mol per mol of phosphine. Particularly preferably, the compound is used in an amount of at least 1 mol per mol of HCl used. The amount of the tetraarylborate compound (IV) in this range enables the production of the phosphonium borate compound (I) in a high yield.

The reaction of the tetraarylborate compound (IV) is desirably carried out while the reaction solution is at −20 to 150° C., preferably 0 to 80° C. and is continuously stirred for up to 24 hours, preferably 1 to 5 hours at the temperature. The reaction under these conditions enables the production of the phosphonium borate compound (I) in a high yield.

After the completion of the reaction, purification such as recrystallization or column chromatography is performed, and consequently the objective novel phosphonium borate compound (I) of Formula (I) can be obtained with high purity:

$(R^1)(R^2)(R^3)PH \cdot BAr_4$             (I)

wherein $R^1$, $R^2$ and $R^3$ are as defined in Formula (II); Ar is as defined in Formula (IV); $R^1$, $R^2$ and $R^3$ cannot be tert-butyl groups simultaneously and Ar cannot be phenyl group at the same time; and $R^1$, $R^2$ and $R^3$ cannot be cyclohexyl groups simultaneously and Ar cannot be phenyl group at the same time.

According to the embodiment 2, the novel phosphonium borate compound (I) can be obtained in a high yield, specifically in a yield of about 76 to 89 mol % in terms of phosphine (II).

The novel phosphonium borate compound produced according to the embodiment 2 of the first production process will be described later.

<Second Production Process>

The second process for producing a phosphonium borate compound includes:

reacting a phosphine with $H_2SO_4$ to produce a phosphine sulfate, the phosphine being represented by Formula (II):

$(R^1)(R^2)(R^3)P$             (II)

wherein $R^1$ is a primary alkyl group of 1 to 20 carbon atoms, a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine sulfate being represented by Formula (V):

$[(R^1)(R^2)(R^3)PH]_{(2-n)} \cdot H_nSO_4$             (V)

wherein $R^1$, $R^2$ and $R^3$ are as defined in Formula (II), and n is an integer of 0 or 1;

and reacting the phosphine sulfate with a tetraarylborate compound represented by Formula (IV):

$M \cdot BAr_4$             (IV)

wherein M is lithium, sodium, potassium, magnesium halide or calcium halide, and Ar is an aryl group of 6 to 20 carbon atoms;

the phosphonium borate compound being represented by Formula (I):

$(R^1)(R^2)(R^3)PH \cdot BAr_4$             (I)

wherein $R^1$, $R^2$ and $R^3$ are as defined in Formula (II), and Ar is as defined in Formula (IV).

Specifically, the second process for producing a phosphonium borate compound (I) includes:

a 1'st step in which the phosphine (II) is reacted with $H_2SO_4$ to give the phosphine sulfate (V); and a 2'nd step in which the compound (V) is reacted with the tetraarylborate compound (IV) to produce the phosphonium borate compound (I), as illustrated in the reaction formula below:

[Chem. 2]

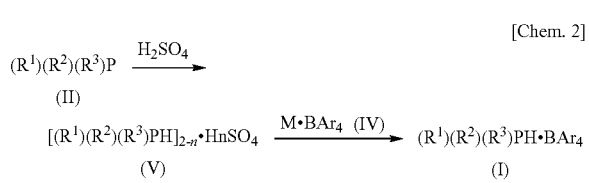

The second production process can produce the phosphonium borate compound (I) in a high yield. The reason for this effect is not clear, but is probably that a side reaction that takes place when the compound (II), $H_2SO_4$ and the compound (IV) are added at the same time can be substantially avoided.

The second process for producing a phosphonium borate compound (I) will be described below with reference to an embodiment 1 for producing the trialkylphosphonium tetraphenylborate and an embodiment 2 for producing the novel phosphonium borate compound.

Embodiment 1

[1'st Step]

In the 1'st step, a trialkylphosphine (II) and $H_2SO_4$ are reacted under predetermined conditions.

These components will be described below.

The trialkylphosphine (II) used as a raw material in the production process is represented by Formula (II):

$(R^1)(R^2)(R^3)P$             (II)

wherein $R^1$, $R^2$ and $R^3$ are ethyl, n-butyl, tert-butyl or cyclohexyl groups, and are the same. Examples of the trialkylphosphines (II) include those described in the embodiment 1 of the first production process.

$H_2SO_4$ used in the production process may be sulfuric acid. The concentration thereof is not particularly limited, and is desirably in the range of 0.1 to 95% by weight, preferably 10 to 40% by weight.

The 1'st step involving the above raw materials is performed in a reactor purged with an inert gas such as nitrogen or argon. The addition sequence of the raw materials is not particularly limited. For example, sulfuric acid may be added to the trialkylphosphine (II), or the trialkylphosphine (II) may be added to sulfuric acid. The addition method is not particularly limited, and the material may be added all at once or may be added dropwise intermittently or continuously.

In the 1'st step, the desirable $H_2SO_4$ requirement, desirable temperature for smooth reaction, and desirable time to complete the reaction vary depending on the type of the trialkylphosphine (II) used, and are selected appropriately.

The $H_2SO_4$ amount varies depending on the type of the trialkylphosphine (II), and is desirably in the range of 0.25 to 2.5 mol, preferably 0.4 to 0.8 mol per mol of phosphine. The $H_2SO_4$ amount in this range enables the production of the trialkylphosphonium tetraphenylborate (I) in a high yield.

The reaction of sulfuric acid is desirably carried out while the solution is at −20 to 150° C., preferably 0 to 80° C. and is continuously stirred for up to 24 hours, preferably 30 minutes to 5 hours at the temperature. The reaction under these conditions enables the production of the trialkylphosphonium tetraphenylborate (I) in a high yield.

The completion of the reaction in the 1'st step may be determined by confirming the absence of unreacted trialkylphosphine (II). Specifically, the organic phase is analyzed by gas chromatography or the like to determine the trialkylphosphine (II) in the organic phase. When the analysis confirms substantial absence of the remaining trialkylphosphine (II), the reaction is terminated. When the trialkylphosphine (II) is still present in the organic phase, the reaction is preferably continued.

The reaction solution takes various forms depending on the solvent used. For example, the solution may contain crystals of trialkylphosphine sulfate (V) (described later), may be a uniform solution or a suspension, or may be a two-phase system consisting of an aqueous phase and an organic phase. In the case of the two-phase system consisting of an aqueous phase and an organic phase, the system is subjected to separation. In the case of other solution forms, separation may be performed as required by adding water, toluene, n-hexane, n-heptane or the like. The aqueous phase resulting from the separation may be washed with toluene, n-hexane, n-heptane or the like as required.

The aqueous phase obtained by the reaction of the 1'st step contains a reaction intermediate dissolved therein that is assumed to be a trialkylphosphine sulfate (V) represented by Formula (V):

wherein $R^1$, $R^2$ and $R^3$ are as defined in Formula (II), and n is an integer of 0 or 1.

The formation of the trialkylphosphine sulfate (V) may be confirmed by, for example, a nuclear magnetic resonance spectrum ($^1$H-NMR).

[2'nd Step]

The reaction intermediate trialkylphosphine sulfate (V) obtained in the 1'st step is reacted with a tetraphenylborate compound (IV) under predetermined conditions to produce a trialkylphosphonium tetraphenylborate represented by Formula (I):

wherein $R^1$, $R^2$ and $R^3$ are ethyl, n-butyl, tert-butyl or cyclohexyl groups, and are the same; and Ar is phenyl group.

The tetraphenylborate compound (IV) used in the 2'nd step is represented by Formula (IV):

wherein M is lithium, sodium, potassium, magnesium halide or calcium halide, and Ar is phenyl group. Examples thereof include those described in the embodiment 1 of the first production process.

Specifically, the 2'nd step involving the above raw materials is performed by mixing the aqueous solution of the reaction intermediate assumed to be the trialkylphosphine sulfate (V), with the tetraphenylborate compound (IV) thereby to react the compound (V) with the compound (IV) under predetermined conditions.

The addition sequence of the aqueous solution obtained in the 1'st step and the tetraphenylborate compound (IV) is not particularly limited. The addition method is not particularly limited, and the material may be added all at once or may be added dropwise intermittently or continuously.

In the 2'nd step, the desirable requirement of the tetraphenylborate compound (IV), desirable temperature for smooth reaction, and desirable time to complete the reaction vary depending on the type of the raw material compound trialkylphosphine (II) used, amount of sulfuric acid, and type of the tetraphenylborate compound (IV), and are selected appropriately.

The amount of the tetraphenylborate compound (IV) varies depending on the type of the trialkylphosphine (II) used in the 1'st step, and is desirably in the range of 0.55 to 5.5 mol, preferably 0.85 to 1.65 mol per mol of phosphine. Particularly preferably, the compound is used in an amount of at least 2 mol per mol of $H_2SO_4$ used. The amount of the tetraphenylborate compound (IV) in this range enables the production of the trialkylphosphonium tetraphenylborate (I) in a high yield.

The reaction of the tetraphenylborate compound (IV) is desirably carried out while the reaction solution is at −20 to 150° C., preferably 0 to 80° C. and is continuously stirred for up to 24 hours, preferably 1 to 5 hours at the temperature. The reaction under these conditions enables the production of the trialkylphosphonium tetraphenylborate (I) in a high yield.

After the completion of the reaction, purification such as recrystallization or column chromatography is performed, and consequently the objective trialkylphosphonium tetraphenylborate (I) of Formula (I) can be obtained with high purity:

wherein $R^1$, $R^2$ and $R^3$ are ethyl, n-butyl, tert-butyl or cyclohexyl groups, and are the same; and Ar is phenyl group.

According to the embodiment 1, the trialkylphosphonium tetraphenylborate (I) can be obtained in a high yield, specifically in a yield of about 87 to 93 mol % in terms of trialkylphosphine (II).

Examples of the trialkylphosphonium tetraphenylborates (I) of Formula (I) produced according to the embodiment 1 of the second production process include triethylphosphonium tetraphenylborate, tri-n-butylphosphonium tetraphenylborate, tri-tert-butylphosphonium tetraphenylborate and tricyclohexylphosphonium tetraphenylborate.

Next, the embodiment 2 for producing the novel phosphonium borate compound will be described.

Embodiment 2

[1'st Step]

In the 1'st step, a phosphine (II) and $H_2SO_4$ are reacted under predetermined conditions. These components will be described below.

The phosphine (II) used as a raw material in the production process is represented by Formula (II):

wherein $R^1$ is a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another. Examples of the phosphines (II) include those described in the embodiment 2 of the first production process.

$H_2SO_4$ may be sulfuric acid. The concentration thereof is not particularly limited, and is desirably in the range of 0.1 to 95% by weight, preferably 10 to 40% by weight.

The 1'st step involving the above raw materials is performed in a reactor purged with an inert gas such as nitrogen or argon. The addition sequence of the raw materials is not particularly limited. For example, sulfuric acid may be added to the phosphine (II), or the phosphine (II) may be added to sulfuric acid. The addition method is not particularly limited, and the material may be added all at once or may be added dropwise intermittently or continuously.

In the 1'st step, the desirable $H_2SO_4$ requirement, desirable temperature for smooth reaction, and desirable time to complete the reaction vary depending on the type of the phosphine (II) used, and are selected appropriately.

The amount of sulfuric acid varies depending on the type of the phosphine (II), and is desirably in the range of 0.25 to 2.5 mol, preferably 0.4 to 0.8 mol per mol of phosphine. The $H_2SO_4$ amount in this range enables the production of the phosphonium borate compound (I) in a high yield.

The reaction of $H_2SO_4$ is desirably carried out while the solution is at −20 to 150° C., preferably 0 to 80° C. and is continuously stirred for up to 24 hours, preferably 30 minutes to 5 hours at the temperature. The reaction under these conditions enables the production of the phosphonium borate compound (I) in a high yield.

The completion of the reaction in the 1'st step may be determined by confirming the absence of unreacted phosphine (II). Specifically, the organic phase is analyzed by gas chromatography or the like to determine the phosphine (II) in the organic phase. When the analysis confirms substantial absence of the remaining phosphine (II), the reaction is terminated. When the phosphine is still present in the organic phase, the reaction is preferably continued.

The reaction solution takes various forms depending on the solvent used. For example, the solution may contain crystals of phosphine sulfate (V) (described later), may be a uniform solution or a suspension, or may be a two-phase system consisting of an aqueous phase and an organic phase. In the case of the two-phase system consisting of an aqueous phase and an organic phase, the phosphine sulfate (V) passes into the aqueous phase and therefore the aqueous phase is subjected to separation. In the case of other solution forms, separation may be performed as required by adding water, toluene, n-hexane, n-heptane or the like. The aqueous phase resulting from the separation may be washed with toluene, n-hexane, n-heptane or the like as required.

The aqueous phase obtained by the reaction of the 1'st step contains a reaction intermediate dissolved therein that is assumed to be a phosphine sulfate (V) represented by Formula (V):

$$[(R^1)(R^2)(R^3)PH]_{(2-n)} \cdot H_nSO_4 \quad (V)$$

wherein $R^1$, $R^2$ and $R^3$ are as defined in Formula (II), and n is an integer of 0 or 1.

The formation of the phosphine sulfate (V) may be confirmed by, for example, a nuclear magnetic resonance spectrum ($^1$H-NMR).

[2'nd Step]

The reaction intermediate that is assumed to be the phosphine sulfate (V) obtained in the 1'st step is reacted with a tetraarylborate compound (IV) under predetermined conditions to produce a phosphonium borate compound (I) of the present invention.

The tetraarylborate compound (IV) used in the 2'nd step is represented by Formula (IV):

$$M \cdot BAr_4 \quad (IV)$$

wherein M is lithium, sodium, potassium, magnesium halide or calcium halide, and Ar is an aryl group of 6 to 20 carbon atoms. Examples of the tetraarylborate compounds include those described in the embodiment 2 of the first production process.

Specifically, the 2'nd step involving the above raw materials is performed by mixing the aqueous solution of the reaction intermediate assumed to be the phosphine sulfate (V), with the tetraarylborate compound (IV) thereby to react the compound (V) with the compound (IV) under predetermined conditions.

The addition sequence of the aqueous solution obtained in the 1'st step and the tetraarylborate compound (IV) is not particularly limited. The addition method is not particularly limited, and the material may be added all at once or may be added dropwise intermittently or continuously.

In the 2'nd step, the desirable requirement of the tetraarylborate compound (IV), desirable temperature for smooth reaction, and desirable time to complete the reaction vary depending on the type of the raw material compound phosphine (II) used, amount of sulfuric acid, and type of the tetraarylborate compound (IV), and are selected appropriately.

The amount of the tetraarylborate compound (IV) varies depending on the type of the phosphine (II) used in the 1'st step, and is desirably in the range of 0.55 to 5.5 mol, preferably 0.85 to 1.65 mol per mol of phosphine. Particularly preferably, the compound is used in an amount of at least 2 mol per mol of $H_2SO_4$ used. The amount of the tetraarylborate compound (IV) in this range enables the production of the phosphonium borate compound (I) in a high yield.

The reaction of the tetraarylborate compound (IV) is desirably carried out while the reaction solution is at −20 to 150° C., preferably 0 to 80° C. and is continuously stirred for up to 24 hours, preferably 1 to 5 hours at the temperature. The reaction under these conditions enables the production of the phosphonium borate compound (I) in a high yield.

After the completion of the reaction, purification such as recrystallization or column chromatography is performed, and consequently the objective novel phosphonium borate compound (I) of Formula (I) can be obtained with high purity.

The second production process can produce the novel phosphonium borate compound (I) in a high yield, specifically in a yield of about 80 to 85 mol % in terms of phosphine (II).

Novel Phosphonium Borate Compound

The novel phosphonium borate compound (I) of the present invention may be produced according to the embodiment 2 of the first production process and according to the embodiment 2 of the second production process. The phosphonium borate compound is represented by Formula (I):

$$(R^1)(R^2)(R^3)PH \cdot BAr_4 \quad (I)$$

wherein $R^1$ is a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms;

$R^1$, $R^2$ and $R^3$ may be the same or different from one another;

Ar is an aryl group of 6 to 20 carbon atoms;

$R^1$, $R^2$ and $R^3$ are not tert-butyl groups simultaneously and Ar is not phenyl group at the same time; and $R^1$, $R^2$ and $R^3$ are not cyclohexyl groups simultaneously and Ar is not phenyl group at the same time.

$R^1$

In Formula (I), $R^1$ is as described below.

$R^1$ may be a secondary alkyl group, desirably a secondary alkyl group having 3 to 20, preferably 3 to 11 carbon atoms. The secondary alkyl groups include isopropyl, sec-butyl, 2-pentyl, 3-pentyl, 2-hexyl and 3-hexyl.

$R^1$ may be a tertiary alkyl group, desirably a tertiary alkyl group having 4 to 20, preferably 4 to 11 carbon atoms. The tertiary alkyl groups include tert-butyl, tert-amyl, 1,1-dimethylbutyl, 3-methyl-3-pentyl and 1,1,2-trimethylpropyl.

$R^1$ may be a cycloalkyl group, desirably a cycloalkyl group having 3 to 20, preferably 3 to 11 carbon atoms. The cycloalkyl groups include cyclopropyl, cyclopentyl, cyclohexyl, 1-methylcyclohexyl, 2-methylcyclohexyl, 1-adamantyl, 2-methyl-1-adamantyl, 2-adamantyl, 1-methyl-2-adamantyl and 2-methyl-2-adamantyl. $R^1$ is not limited to the groups described above.

$R^2$

In Formula (I), $R^2$ is as described below.

$R^2$ may be a primary alkyl group, desirably a primary alkyl group having 1 to 20, preferably 1 to 8 carbon atoms. The primary alkyl groups include methyl, ethyl, n-propyl, n-butyl, isobutyl, n-pentyl, isopentyl, n-hexyl, 2-methyl-1-pentyl, 2,2-diethyl-1-ethyl, n-heptyl and n-octyl.

$R^2$ may be a secondary alkyl group, desirably a secondary alkyl group having 3 to 20, preferably 3 to 11 carbon atoms. The secondary alkyl groups include isopropyl, sec-butyl, 2-pentyl, 3-pentyl, 2-hexyl and 3-hexyl.

$R^2$ may be a tertiary alkyl group, desirably a tertiary alkyl group having 4 to 20, preferably 4 to 11 carbon atoms. The tertiary alkyl groups include tert-butyl, tert-amyl, 1,1-dimethylbutyl, 3-methyl-3-pentyl and 1,1,2-trimethylpropyl.

$R^2$ may be a cycloalkyl group, desirably a cycloalkyl group having 3 to 20, preferably 3 to 11 carbon atoms. The cycloalkyl groups include cyclopropyl, cyclopentyl, cyclohexyl, 1-methylcyclohexyl, 2-methylcyclohexyl, 1-adamantyl, 2-methyl-1-adamantyl, 2-adamantyl, 1-methyl-2-adamantyl and 2-methyl-2-adamantyl.

$R^2$ may be an aralkyl group, desirably an aralkyl group having 7 to 20, preferably 7 to 12 carbon atoms. The aralkyl groups include benzyl, 1-phenylethyl, 2-phenylethyl, 2-ethenylbenzyl, 3-ethenylbenzyl, 4-ethenylbenzyl, 4-(2-ethenylphenyl)butyl, 4-(3-ethenylphenyl)butyl and 4-(4-ethenylphenyl) butyl.

$R^2$ may desirably be an allyl group having 3 to 20, preferably 3 to 8 carbon atoms. The allyl groups include allyl and 2-octenyl. $R^2$ is not limited to the groups described above.

$R^3$

In Formula (I), $R^3$ is as described below.

$R^3$ may be a primary alkyl group, desirably a primary alkyl group having 1 to 20, preferably 1 to 8 carbon atoms. The primary alkyl groups include methyl, ethyl, n-propyl, n-butyl, isobutyl, n-pentyl, isopentyl, n-hexyl, 2-methyl-1-pentyl, 2,2-diethyl-1-ethyl, n-heptyl and n-octyl.

$R^3$ may be a secondary alkyl group, desirably a secondary alkyl group having 3 to 20, preferably 3 to 11 carbon atoms. The secondary alkyl groups include isopropyl, sec-butyl, 2-pentyl, 3-pentyl, 2-hexyl and 3-hexyl.

$R^3$ may be a tertiary alkyl group, desirably a tertiary alkyl group having 4 to 20, preferably 4 to 11 carbon atoms. The tertiary alkyl groups include tert-butyl, tert-amyl, 1,1-dimethylbutyl, 3-methyl-3-pentyl and 1,1,2-trimethylpropyl.

$R^3$ may be a cycloalkyl group, desirably a cycloalkyl group having 3 to 20, preferably 3 to 11 carbon atoms. The cycloalkyl groups include cyclopropyl, cyclopentyl, cyclohexyl, 1-methylcyclohexyl, 2-methylcyclohexyl, 1-adamantyl, 2-methyl-1-adamantyl, 2-adamantyl, 1-methyl-2-adamantyl and 2-methyl-2-adamantyl.

$R^3$ may be an aryl group, desirably an aryl group having 6 to 30, preferably 6 to 22 carbon atoms. The aryl groups include phenyl, ortho-tolyl, meta-tolyl, para-tolyl, 2,3-xylyl, 2,4-xylyl, 2,5-xylyl, 2,6-xylyl, 3,4-xylyl, 3,5-xylyl, mesityl, 2-tert-butylphenyl, 3-tert-butylphenyl, 4-tert-butylphenyl, 2-ethenylphenyl, 3-ethenylphenyl, 4-ethenylphenyl, 2-biphenylyl, 3-biphenylyl, 4-biphenylyl, 1-naphthyl, 2-naphthyl, 1,1'-binaphthalene-2-yl, 2-methoxyphenyl, 3-methoxyphenyl, 4-methoxyphenyl, 2-tert-butoxyphenyl, 3-tert-butoxyphenyl, 4-tert-butoxyphenyl, 2-dimethylaminophenyl, 3-dimethylaminophenyl, 4-dimethylaminophenyl, 2'-dimethylamino-2-biphenylyl, 8-dimethylamino-1-naphthyl and 2'-dimethylamino-1,1'-binaphthalene-2-yl.

$R^3$ may be an aralkyl group, desirably an aralkyl group having 7 to 20, preferably 7 to 12 carbon atoms. The aralkyl groups include benzyl, 1-phenylethyl, 2-phenylethyl, 2-ethenylbenzyl, 3-ethenylbenzyl, 4-ethenylbenzyl, 4-(2-ethenylphenyl)butyl, 4-(3-ethenylphenyl)butyl and 4-(4-ethenylphenyl)butyl.

$R^3$ may be an alkenyl group, desirably an alkenyl group having 2 to 20, preferably 2 to 8 carbon atoms. The alkenyl groups include vinyl, methallyl and 1-octenyl.

$R^3$ may be an alkynyl group, desirably an alkynyl group having 2 to 20, preferably 2 to 8 carbon atoms. The alkynyl groups include ethynyl, 1-propynyl and 1-octynyl.

$R^3$ may desirably be an allyl group having 3 to 20, preferably 3 to 8 carbon atoms. The allyl groups include allyl and 2-octenyl. $R^3$ is not limited to the groups described above.

As long as $R^1$, $R^2$ and $R^3$ are selected from the above groups, they may have an arbitrary combination in terms of carbon atom numbers.

Ar

In Formula (I), Ar is desirably an aryl group of 6 to 20, preferably 6 to 10 carbon atoms.

The aryl groups include phenyl, ortho-tolyl, meta-tolyl, para-tolyl, 2,3-xylyl, 2,4-xylyl, 2,5-xylyl, 2,6-xylyl, 3,4-xylyl, 3,5-xylyl, mesityl, 2-tert-butylphenyl, 3-tert-butylphenyl, 4-tert-butylphenyl, 2-methoxyphenyl, 3-methoxyphenyl, 4-methoxyphenyl, 2-tert-butoxyphenyl, 3-tert-butoxyphenyl and 4-tert-butoxyphenyl. Ar is not limited to the groups described above.

In Formula (I), $R^1$, $R^2$ and $R^3$ cannot be tert-butyl groups simultaneously and Ar cannot be phenyl group at the same time, and $R^1$, $R^2$ and $R^3$ cannot be cyclohexyl groups simultaneously and Ar cannot be phenyl group at the same time.

The novel phosphonium borate compound preferably has Formula (I) given below for the reason that the raw material phosphine (II) and tetraarylborate compound (IV) can be synthesized easily by known methods:

$$(R^1)(R^2)(R^3)PH.BAr_4 \quad (I)$$

wherein $R^1$ is a secondary alkyl group of 3 to 6 carbon atoms, a tertiary alkyl group of 4 to 8 carbon atoms, or a cycloalkyl group of 3 to 8 carbon atoms;

$R^2$ is a hydrogen atom, a primary alkyl group of 1 to 8 carbon atoms, a secondary alkyl group of 3 to 6 carbon atoms, a tertiary alkyl group of 4 to 8 carbon atoms, a cycloalkyl group of 3 to 8 carbon atoms, an aralkyl group of 7 to 9 carbon atoms, or an allyl group of 3 to 4 carbon atoms;

$R^3$ is a hydrogen atom, a primary alkyl group of 1 to 8 carbon atoms, a secondary alkyl group of 3 to 6 carbon atoms, a tertiary alkyl group of 4 to 8 carbon atoms, a cycloalkyl group of 3 to 8 carbon atoms, an aryl group of 6 to 15 carbon atoms, an aralkyl group of 7 to 9 carbon atoms, an alkenyl group of 2 to 4 carbon atoms, an alkynyl group of 2 to 4 carbon atoms, or an allyl group of 3 to 4 carbon atoms;

$R^1$, $R^2$ and $R^3$ may be the same or different from one another;

Ar is an aryl group of 6 to 10 carbon atoms;

$R^1$, $R^2$ and $R^3$ cannot be tert-butyl groups simultaneously and Ar cannot be phenyl group at the same time; and $R^1$, $R^2$ and $R^3$ cannot be cyclohexyl groups simultaneously and Ar cannot be phenyl group at the same time.

Specific examples of the novel phosphonium borate compounds (I) represented by Formula (I) are shown in Tables 11-1 to 18-3 which will be presented later.

Of the phosphonium borate compounds (I), preferred are:
(1) di-tert-butylmethylphosphonium tetraphenylborate,
(2) di-tert-butylmethylphosphonium tetra-para-tolylborate,
(3) tri-tert-butylphosphonium tetra-para-tolylborate,
(4) di-tert-butylethylphosphonium tetraphenylborate,
(5) n-butyl-di-tert-butylphosphonium tetraphenylborate,
(6) sec-butyl-di-tert-butylphosphonium tetraphenylborate,
(7) cyclohexyl-di-tert-butylphosphonium tetraphenylborate,
(8) di-tert-butyl-n-octylphosphonium tetraphenylborate,
(9) di-tert-butylphenylphosphonium tetraphenylborate,
(10) 2-biphenylyl-di-tert-butylphosphonium tetraphenylborate,
(11) di-tert-butyl-1-naphthylphosphonium tetraphenylborate,
(12) benzyl-di-tert-butylphosphonium tetraphenylborate,
(13) di-tert-butyl(4-ethenylbenzyl)phosphonium tetraphenylborate,
(14) di-tert-butylvinylphosphonium tetraphenylborate,
(15) allyl-di-tert-butylphosphonium tetraphenylborate,
(16) tricyclohexylphosphonium tetra-para-tolylborate,
(17) triisopropylphosphonium tetraphenylborate,
(18) tricyclopentylphosphonium tetraphenylborate and
(19) n-butyldicyclohexylphosphonium tetraphenylborate.

Of these, the compounds (1), (3), (16) and (17) are more preferable.

The phosphonium borate compounds (I) are particularly useful in combination with a transition metal, salt thereof, oxide thereof or complex thereof in the carbon-carbon bond forming reactions, carbon-nitrogen bond forming reactions and carbon-oxygen bond forming reactions wherein a transition metal complex having a phosphine ligand produces catalytic effects, wherein the phosphonium borate compounds in combination with the transition metal, salt thereof, oxide thereof or complex thereof are used in place of the transition metal complex having a phosphine ligand.

<Use>

The phosphonium borate compounds (I) can be used in combination with a transition metal, transition metal salt, transition metal oxide or transition metal complex in the carbon-carbon bond forming reactions such as Suzuki-Miyaura reaction, Kumada reaction, Negishi reaction, Hiyama reaction, Kosugi-Stille reaction, Heck reaction, Endo reaction and α-allylation of carbonyl compounds; carbon-nitrogen bond forming reactions such as Buchwald-Hartwig amination; and carbon-oxygen bond forming reactions such as ether synthesis wherein a transition metal complex having a phosphine ligand produces catalytic effects, wherein the phosphonium borate compounds in combination with the transition metal, transition metal salt, transition metal oxide or transition metal complex are used in place of the transition metal complex having a phosphine ligand.

The transition metals include, but are not limited to, manganese, iron, cobalt, nickel, ruthenium, rhodium, palladium and platinum.

The transition metal salts include fluorides, chlorides, bromides, iodides, sulfates, nitrates, nitrites, carbonates, borates, ammonium salts, sodium salts, potassium salts, acetates, trifluoroacetates, acetylacetone salts, hydride salts, sulfides and cyanides of manganese, iron, cobalt, nickel, ruthenium, rhodium, palladium and platinum. Hydrates of these transition metal salts are also employable. Specific examples include, but are not limited to, manganese (II) chloride, iron (II) chloride, iron (III) chloride, cobalt (II) chloride, nickel (II) chloride, ruthenium (III) chloride, rhodium (III) chloride, palladium (II) chloride, palladium (II) bromide, manganese (II) acetate, manganese (III) acetate, iron (II) acetate, cobalt (II) acetate, nickel (II) acetate, rhodium (II) acetate dimer, palladium (II) acetate, manganese (II) acetylacetonate, manganese (III) acetylacetonate, iron (II) acetylacetonate, iron (III) acetylacetonate, cobalt (II) acetylacetonate, cobalt (III) acetylacetonate, nickel (II) acetylacetonate, ruthenium (III) acetylacetonate, rhodium (III) acetylacetonate, palladium (II) acetylacetonate, platinum (II) acetylacetonate and sodium (IV) chloroplatinate hexahydrate.

The transition metal oxides include oxides of manganese, iron, cobalt, nickel, ruthenium, rhodium, palladium and platinum. Hydrates of these transition metal oxides are also employable. Specific examples include, but are not limited to, manganese (II) oxide, iron (III) oxide, cobalt (II) oxide, nickel (II) oxide, ruthenium (IV) oxide, rhodium (III) oxide, palladium (II) oxide and platinum (IV) oxide.

The transition metal complexes include benzonitrile complexes, acetonitrile complexes, triphenylphosphine complexes, ethylene complexes, allyl complexes, butadiene complexes, cyclopentadiene complexes, cyclooctadiene complexes, cyclooctatetraene complexes, carbonyl complexes, dibenzylideneacetone complexes, amine complexes, ethylenediamine complexes, pyridine complexes and disiloxane complexes of manganese, iron, cobalt, nickel, ruthenium, rhodium, palladium and platinum. Hydrates of these transition metal complexes are also employable. Specific examples include, but are not limited to, decacarbonylmanganese (0), bis(cyclooctatetraene)iron (0), bis (cyclopentadienyl)cobalt (0), bis(cyclooctadiene)nickel (0), bis (cyclopentadienyl)ruthenium (0), tetrarhodiumdodecacarbonyl (0), tris(dibenzylideneacetone)dipalladium (0), bis(benzonitrile)dichloropalladium (II), allylpalladium chloride dimer and divinyltetramethyldisiloxane platinum (0).

Tables 1-1 to 4-2 below show specific examples of the phosphines of Formula (II) that are used as starting compounds in the embodiment 2 of the first production process and the embodiment 2 of the second production process for producing a phosphonium borate compound according to the present invention. Tables 5 to 10 below show specific examples of the tetraarylborate compounds of Formula (IV). Tables 11-1 to 18-3 below show specific examples of the novel phosphonium borate compounds (I) according to the present invention.

Specific examples of the phosphines (II) represented by Formula (II):

$$(R^1)(R^2)(R^3)P \quad \quad (II)$$

include, but are not limited to, the following compounds.

TABLE 1

Table 1-1

| $R^1$ | $R^2$ | $R^3$ |
|---|---|---|
| tert-butyl | tert-butyl | hydrogen |
| tert-butyl | tert-butyl | methyl |
| tert-butyl | tert-butyl | ethyl |
| tert-butyl | tert-butyl | n-propyl |
| tert-butyl | tert-butyl | n-butyl |
| tert-butyl | tert-butyl | isobutyl |
| tert-butyl | tert-butyl | n-pentyl |
| tert-butyl | tert-butyl | isopentyl |
| tert-butyl | tert-butyl | n-hexyl |
| tert-butyl | tert-butyl | 2-methyl-1-pentyl |
| tert-butyl | tert-butyl | 2,2-diethyl-1-ethyl |
| tert-butyl | tert-butyl | n-heptyl |
| tert-butyl | tert-butyl | n-octyl |
| tert-butyl | tert-butyl | isopropyl |
| tert-butyl | tert-butyl | sec-butyl |
| tert-butyl | tert-butyl | 2-pentyl |
| tert-butyl | tert-butyl | 3-pentyl |
| tert-butyl | tert-butyl | 2-hexyl |
| tert-butyl | tert-butyl | 3-hexyl |
| tert-butyl | tert-butyl | tert-butyl |
| tert-butyl | tert-butyl | tert-amyl |
| tert-butyl | tert-butyl | 1,1-dimethylbutyl |
| tert-butyl | tert-butyl | 3-methyl-3-pentyl |
| tert-butyl | tert-butyl | 1,1,2-trimethylpropyl |
| tert-butyl | tert-butyl | 1-adamantyl |
| tert-butyl | tert-butyl | 2-methyl-1-adamantyl |
| tert-butyl | tert-butyl | cyclopropyl |
| tert-butyl | tert-butyl | cyclopentyl |
| tert-butyl | tert-butyl | cyclohexyl |
| tert-butyl | tert-butyl | 1-methylcyclohexyl |
| tert-butyl | tert-butyl | 2-methylcyclohexyl |
| tert-butyl | tert-butyl | 2-adamantyl |
| tert-butyl | tert-butyl | 1-methyl-2-adamantyl |
| tert-butyl | tert-butyl | 2-methyl-2-adamantyl |
| tert-butyl | tert-butyl | phenyl |
| tert-butyl | tert-butyl | ortho-tolyl |
| tert-butyl | tert-butyl | meta-tolyl |
| tert-butyl | tert-butyl | para-tolyl |
| tert-butyl | tert-butyl | 2,3-xylyl |
| tert-butyl | tert-butyl | 2,4-xylyl |
| tert-butyl | tert-butyl | 2,5-xylyl |
| tert-butyl | tert-butyl | 2,6-xylyl |
| tert-butyl | tert-butyl | 3,4-xylyl |
| tert-butyl | tert-butyl | 3,5-xylyl |
| tert-butyl | tert-butyl | mesityl |

TABLE 2

Table 1-2

| $R^1$ | $R^2$ | $R^3$ |
|---|---|---|
| tert-butyl | tert-butyl | 2-tert-butylphenyl |
| tert-butyl | tert-butyl | 3-tert-butylphenyl |
| tert-butyl | tert-butyl | 4-tert-butylphenyl |
| tert-butyl | tert-butyl | 2-ethenylphenyl |
| tert-butyl | tert-butyl | 3-ethenylphenyl |
| tert-butyl | tert-butyl | 4-ethenylphenyl |

TABLE 2-continued

Table 1-2

| $R^1$ | $R^2$ | $R^3$ |
|---|---|---|
| tert-butyl | tert-butyl | 2-biphenylyl |
| tert-butyl | tert-butyl | 3-biphenylyl |
| tert-butyl | tert-butyl | 4-biphenylyl |
| tert-butyl | tert-butyl | 1-naphthyl |
| tert-butyl | tert-butyl | 2-naphthyl |
| tert-butyl | tert-butyl | 1,1'-binaphthalene-2-yl |
| tert-butyl | tert-butyl | 2-methoxyphenyl |
| tert-butyl | tert-butyl | 3-methoxyphenyl |
| tert-butyl | tert-butyl | 4-methoxyphenyl |
| tert-butyl | tert-butyl | 2-tert-butoxyphenyl |
| tert-butyl | tert-butyl | 3-tert-butoxyphenyl |
| tert-butyl | tert-butyl | 4-tert-butoxyphenyl |
| tert-butyl | tert-butyl | 2-dimethylaminophenyl |
| tert-butyl | tert-butyl | 3-dimethylaminophenyl |
| tert-butyl | tert-butyl | 4-dimethylaminophenyl |
| tert-butyl | tert-butyl | 2'-dimethylamino-2-biphenylyl |
| tert-butyl | tert-butyl | 8-dimethylamino-1-naphthyl |
| tert-butyl | tert-butyl | 2'-dimethylamino-1,1'-binaphthalene-2-yl |
| tert-butyl | tert-butyl | benzyl |
| tert-butyl | tert-butyl | 1-phenylethyl |
| tert-butyl | tert-butyl | 2-phenylethyl |
| tert-butyl | tert-butyl | 2-ethenylbenzyl |
| tert-butyl | tert-butyl | 3-ethenylbenzyl |
| tert-butyl | tert-butyl | 4-ethenylbenzyl |
| tert-butyl | tert-butyl | 4-(2-ethenylphenyl)butyl |
| tert-butyl | tert-butyl | 4-(3-ethenylphenyl)butyl |
| tert-butyl | tert-butyl | 4-(4-ethenylphenyl)butyl |
| tert-butyl | tert-butyl | vinyl |
| tert-butyl | tert-butyl | methallyl |
| tert-butyl | tert-butyl | 1-octenyl |
| tert-butyl | tert-butyl | ethynyl |
| tert-butyl | tert-butyl | 1-propynyl |
| tert-butyl | tert-butyl | 1-octynyl |
| tert-butyl | tert-butyl | allyl |
| tert-butyl | tert-butyl | 2-octenyl |
| isopropyl | isopropyl | isopropyl |
| n-butyl | cyclohexyl | cyclohexyl |
| cyclopentyl | cyclopentyl | cyclopentyl |
| cyclohexyl | cyclohexyl | cyclohexyl |

TABLE 3

Table 2-1

| $R^1$ | $R^2$ | $R^3$ |
|---|---|---|
| tert-amyl | tert-amyl | hydrogen |
| tert-amyl | tert-amyl | methyl |
| tert-amyl | tert-amyl | ethyl |
| tert-amyl | tert-amyl | n-propyl |
| tert-amyl | tert-amyl | n-butyl |
| tert-amyl | tert-amyl | isobutyl |
| tert-amyl | tert-amyl | n-pentyl |
| tert-amyl | tert-amyl | isopentyl |
| tert-amyl | tert-amyl | n-hexyl |
| tert-amyl | tert-amyl | 2-methyl-1-pentyl |
| tert-amyl | tert-amyl | 2,2-diethyl-1-ethyl |
| tert-amyl | tert-amyl | n-heptyl |
| tert-amyl | tert-amyl | n-octyl |
| tert-amyl | tert-amyl | isopropyl |
| tert-amyl | tert-amyl | sec-butyl |
| tert-amyl | tert-amyl | 2-pentyl |
| tert-amyl | tert-amyl | 3-pentyl |
| tert-amyl | tert-amyl | 2-hexyl |
| tert-amyl | tert-amyl | 3-hexyl |
| tert-amyl | tert-amyl | tert-butyl |
| tert-amyl | tert-amyl | tert-amyl |
| tert-amyl | tert-amyl | 1,1-dimethylbutyl |
| tert-amyl | tert-amyl | 3-methyl-3-pentyl |
| tert-amyl | tert-amyl | 1,1,2-trimethylpropyl |
| tert-amyl | tert-amyl | 1-adamantyl |
| tert-amyl | tert-amyl | 2-methyl-1-adamantyl |

TABLE 3-continued

Table 2-1

| R¹ | R² | R³ |
|---|---|---|
| tert-amyl | tert-amyl | cyclopropyl |
| tert-amyl | tert-amyl | cyclopentyl |
| tert-amyl | tert-amyl | cyclohexyl |
| tert-amyl | tert-amyl | 1-methylcyclohexyl |
| tert-amyl | tert-amyl | 2-methylcyclohexyl |
| tert-amyl | tert-amyl | 2-adamantyl |
| tert-amyl | tert-amyl | 1-methyl-2-adamantyl |
| tert-amyl | tert-amyl | 2-methyl-2-adamantyl |
| tert-amyl | tert-amyl | phenyl |
| tert-amyl | tert-amyl | ortho-tolyl |
| tert-amyl | tert-amyl | meta-tolyl |
| tert-amyl | tert-amyl | para-tolyl |
| tert-amyl | tert-amyl | 2,3-xylyl |
| tert-amyl | tert-amyl | 2,4-xylyl |
| tert-amyl | tert-amyl | 2,5-xylyl |
| tert-amyl | tert-amyl | 2,6-xylyl |
| tert-amyl | tert-amyl | 3,4-xylyl |

TABLE 4

Table 2-2

| R¹ | R² | R³ |
|---|---|---|
| tert-amyl | tert-amyl | 3,5-xylyl |
| tert-amyl | tert-amyl | mesityl |
| tert-amyl | tert-amyl | 2-tert-butylphenyl |
| tert-amyl | tert-amyl | 3-tert-butylphenyl |
| tert-amyl | tert-amyl | 4-tert-butylphenyl |
| tert-amyl | tert-amyl | 2-ethenylphenyl |
| tert-amyl | tert-amyl | 3-ethenylphenyl |
| tert-amyl | tert-amyl | 4-ethenylphenyl |
| tert-amyl | tert-amyl | 2-biphenylyl |
| tert-amyl | tert-amyl | 3-biphenylyl |
| tert-amyl | tert-amyl | 4-biphenylyl |
| tert-amyl | tert-amyl | 1-naphthyl |
| tert-amyl | tert-amyl | 2-naphthyl |
| tert-amyl | tert-amyl | 1,1'-binaphthalene-2-yl |
| tert-amyl | tert-amyl | 2-methoxyphenyl |
| tert-amyl | tert-amyl | 3-methoxyphenyl |
| tert-amyl | tert-amyl | 4-methoxyphenyl |
| tert-amyl | tert-amyl | 2-tert-butoxyphenyl |
| tert-amyl | tert-amyl | 3-tert-butoxyphenyl |
| tert-amyl | tert-amyl | 4-tert-butoxyphenyl |
| tert-amyl | tert-amyl | 2-dimethylaminophenyl |
| tert-amyl | tert-amyl | 3-dimethylaminophenyl |
| tert-amyl | tert-amyl | 4-dimethylaminophenyl |
| tert-amyl | tert-amyl | 2'-dimethylamino-2-biphenylyl |
| tert-amyl | tert-amyl | 8-dimethylamino-1-naphthyl |
| tert-amyl | tert-amyl | 2'-dimethylamino-1,1'-binaphthalene-2-yl |
| tert-amyl | tert-amyl | benzyl |
| tert-amyl | tert-amyl | 1-phenylethyl |
| tert-amyl | tert-amyl | 2-phenylethyl |
| tert-amyl | tert-amyl | 2-ethenylbenzyl |
| tert-amyl | tert-amyl | 3-ethenylbenzyl |
| tert-amyl | tert-amyl | 4-ethenylbenzyl |
| tert-amyl | tert-amyl | 4-(2-ethenylphenyl)butyl |
| tert-amyl | tert-amyl | 4-(3-ethenylphenyl)butyl |
| tert-amyl | tert-amyl | 4-(4-ethenylphenyl)butyl |
| tert-amyl | tert-amyl | vinyl |
| tert-amyl | tert-amyl | methallyl |
| tert-amyl | tert-amyl | 1-octenyl |
| tert-amyl | tert-amyl | ethynyl |
| tert-amyl | tert-amyl | 1-propynyl |
| tert-amyl | tert-amyl | 1-octynyl |
| tert-amyl | tert-amyl | allyl |
| tert-amyl | tert-amyl | 2-octenyl |

TABLE 5

Table 3-1

| R¹ | R² | R³ |
|---|---|---|
| 1-adamantyl | 1-adamantyl | hydrogen |
| 1-adamantyl | 1-adamantyl | methyl |
| 1-adamantyl | 1-adamantyl | ethyl |
| 1-adamantyl | 1-adamantyl | n-propyl |
| 1-adamantyl | 1-adamantyl | n-butyl |
| 1-adamantyl | 1-adamantyl | isobutyl |
| 1-adamantyl | 1-adamantyl | n-pentyl |
| 1-adamantyl | 1-adamantyl | isopentyl |
| 1-adamantyl | 1-adamantyl | n-hexyl |
| 1-adamantyl | 1-adamantyl | 2-methyl-1-pentyl |
| 1-adamantyl | 1-adamantyl | 2,2-diethyl-1-ethyl |
| 1-adamantyl | 1-adamantyl | n-heptyl |
| 1-adamantyl | 1-adamantyl | n-octyl |
| 1-adamantyl | 1-adamantyl | isopropyl |
| 1-adamantyl | 1-adamantyl | sec-butyl |
| 1-adamantyl | 1-adamantyl | 2-pentyl |
| 1-adamantyl | 1-adamantyl | 3-pentyl |
| 1-adamantyl | 1-adamantyl | 2-hexyl |
| 1-adamantyl | 1-adamantyl | 3-hexyl |
| 1-adamantyl | 1-adamantyl | tert-butyl |
| 1-adamantyl | 1-adamantyl | tert-amyl |
| 1-adamantyl | 1-adamantyl | 1,1-dimethylbutyl |
| 1-adamantyl | 1-adamantyl | 3-methyl-3-pentyl |
| 1-adamantyl | 1-adamantyl | 1,1,2-trimethylpropyl |
| 1-adamantyl | 1-adamantyl | 1-adamantyl |
| 1-adamantyl | 1-adamantyl | 2-methyl-1-adamantyl |
| 1-adamantyl | 1-adamantyl | cyclopropyl |
| 1-adamantyl | 1-adamantyl | cyclopentyl |
| 1-adamantyl | 1-adamantyl | cyclohexyl |
| 1-adamantyl | 1-adamantyl | 1-methylcyclohexyl |
| 1-adamantyl | 1-adamantyl | 2-methylcyclohexyl |
| 1-adamantyl | 1-adamantyl | 2-adamantyl |
| 1-adamantyl | 1-adamantyl | 1-methyl-2-adamantyl |
| 1-adamantyl | 1-adamantyl | 2-methyl-2-adamantyl |
| 1-adamantyl | 1-adamantyl | phenyl |
| 1-adamantyl | 1-adamantyl | ortho-tolyl |
| 1-adamantyl | 1-adamantyl | meta-tolyl |
| 1-adamantyl | 1-adamantyl | para-tolyl |
| 1-adamantyl | 1-adamantyl | 2,3-xylyl |
| 1-adamantyl | 1-adamantyl | 2,4-xylyl |
| 1-adamantyl | 1-adamantyl | 2,5-xylyl |
| 1-adamantyl | 1-adamantyl | 2,6-xylyl |
| 1-adamantyl | 1-adamantyl | 3,4-xylyl |
| 1-adamantyl | 1-adamantyl | 3,5-xylyl |
| 1-adamantyl | 1-adamantyl | mesityl |

TABLE 6

Table 3-2

| R¹ | R² | R³ |
|---|---|---|
| 1-adamantyl | 1-adamantyl | 2-tert-butylphenyl |
| 1-adamantyl | 1-adamantyl | 3-tert-butylphenyl |
| 1-adamantyl | 1-adamantyl | 4-tert-butylphenyl |
| 1-adamantyl | 1-adamantyl | 2-ethenylphenyl |
| 1-adamantyl | 1-adamantyl | 3-ethenylphenyl |
| 1-adamantyl | 1-adamantyl | 4-ethenylphenyl |
| 1-adamantyl | 1-adamantyl | 2-biphenylyl |
| 1-adamantyl | 1-adamantyl | 3-biphenylyl |
| 1-adamantyl | 1-adamantyl | 4-biphenylyl |
| 1-adamantyl | 1-adamantyl | 1-naphthyl |
| 1-adamantyl | 1-adamantyl | 2-naphthyl |
| 1-adamantyl | 1-adamantyl | 1,1'-binaphthalene-2-yl |
| 1-adamantyl | 1-adamantyl | 2-methoxyphenyl |
| 1-adamantyl | 1-adamantyl | 3-methoxyphenyl |
| 1-adamantyl | 1-adamantyl | 4-methoxyphenyl |
| 1-adamantyl | 1-adamantyl | 2-tert-butoxyphenyl |
| 1-adamantyl | 1-adamantyl | 3-tert-butoxyphenyl |
| 1-adamantyl | 1-adamantyl | 4-tert-butoxyphenyl |
| 1-adamantyl | 1-adamantyl | 2-dimethylaimnophenyl |
| 1-adamantyl | 1-adamantyl | 3-dimethylaminophenyl |

TABLE 6-continued

Table 3-2

| R¹ | R² | R³ |
|---|---|---|
| 1-adamantyl | 1-adamantyl | 4-dimethylaminophenyl |
| 1-adamantyl | 1-adamantyl | 2'-dimethylamino-2-biphenylyl |
| 1-adamantyl | 1-adamantyl | 8-dimethylamino-1-naphthyl |
| 1-adamantyl | 1-adamantyl | 2'-dimethylamino-1,1'-binaphthalene-2-yl |
| 1-adamantyl | 1-adamantyl | benzyl |
| 1-adamantyl | 1-adamantyl | 1-phenylethyl |
| 1-adamantyl | 1-adamantyl | 2-phenylethyl |
| 1-adamantyl | 1-adamantyl | 2-ethenylbenzyl |
| 1-adamantyl | 1-adamantyl | 3-ethenylbenzyl |
| 1-adamantyl | 1-adamantyl | 4-ethenylbenzyl |
| 1-adamantyl | 1-adamantyl | 4-(2-ethenylphenyl)butyl |
| 1-adamantyl | 1-adamantyl | 4-(3-ethenylphenyl)butyl |
| 1-adamantyl | 1-adamantyl | 4-(4-ethenylphenyl)butyl |
| 1-adamantyl | 1-adamantyl | vinyl |
| 1-adamantyl | 1-adamantyl | methallyl |
| 1-adamantyl | 1-adamantyl | 1-octenyl |
| 1-adamantyl | 1-adamantyl | ethynyl |
| 1-adamantyl | 1-adamantyl | 1-propynyl |
| 1-adamantyl | 1-adamantyl | 1-octynyl |
| 1-adamantyl | 1-adamantyl | allyl |
| 1-adamantyl | 1-adamantyl | 2-octenyl |

TABLE 7

Table 4-1

| R¹ | R² | R³ |
|---|---|---|
| 2-adamantyl | 2-adamantyl | hydrogen |
| 2-adamantyl | 2-adamantyl | methyl |
| 2-adamantyl | 2-adamantyl | ethyl |
| 2-adamantyl | 2-adamantyl | n-propyl |
| 2-adamantyl | 2-adamantyl | n-butyl |
| 2-adamantyl | 2-adamantyl | isobutyl |
| 2-adamantyl | 2-adamantyl | n-pentyl |
| 2-adamantyl | 2-adamantyl | isopentyl |
| 2-adamantyl | 2-adamantyl | n-hexyl |
| 2-adamantyl | 2-adamantyl | 2-methyl-1-pentyl |
| 2-adamantyl | 2-adamantyl | 2,2-diethyl-1-ethyl |
| 2-adamantyl | 2-adamantyl | n-heptyl |
| 2-adamantyl | 2-adamantyl | n-octyl |
| 2-adamantyl | 2-adamantyl | isopropyl |
| 2-adamantyl | 2-adamantyl | sec-butyl |
| 2-adamantyl | 2-adamantyl | 2-pentyl |
| 2-adamantyl | 2-adamantyl | 3-pentyl |
| 2-adamantyl | 2-adamantyl | 2-hexyl |
| 2-adamantyl | 2-adamantyl | 3-hexyl |
| 2-adamantyl | 2-adamantyl | tert-butyl |
| 2-adamantyl | 2-adamantyl | tert-amyl |
| 2-adamantyl | 2-adamantyl | 1,1-dimethylbutyl |
| 2-adamantyl | 2-adamantyl | 3-methyl-3-pentyl |
| 2-adamantyl | 2-adamantyl | 1,1,2-trimethylpropyl |
| 2-adamantyl | 2-adamantyl | 1-adamantyl |
| 2-adamantyl | 2-adamantyl | 2-methyl-1-adamantyl |
| 2-adamantyl | 2-adamantyl | cyclopropyl |
| 2-adamantyl | 2-adamantyl | cyclopentyl |
| 2-adamantyl | 2-adamantyl | cyclohexyl |
| 2-adamantyl | 2-adamantyl | 1-methylcyclohexyl |
| 2-adamantyl | 2-adamantyl | 2-methylcyclohexyl |
| 2-adamantyl | 2-adamantyl | 2-adamantyl |
| 2-adamantyl | 2-adamantyl | 1-methyl-2-adamantyl |
| 2-adamantyl | 2-adamantyl | 2-methyl-2-adamantyl |
| 2-adamantyl | 2-adamantyl | phenyl |
| 2-adamantyl | 2-adamantyl | ortho-tolyl |
| 2-adamantyl | 2-adamantyl | meta-tolyl |
| 2-adamantyl | 2-adamantyl | para-tolyl |
| 2-adamantyl | 2-adamantyl | 2,3-xylyl |
| 2-adamantyl | 2-adamantyl | 2,4-xylyl |
| 2-adamantyl | 2-adamantyl | 2,5-xylyl |
| 2-adamantyl | 2-adamantyl | 2,6-xylyl |
| 2-adamantyl | 2-adamantyl | 3,4-xylyl |
| 2-adamantyl | 2-adamantyl | 3,5-xylyl |
| 2-adamantyl | 2-adamantyl | mesityl |

TABLE 8

Table 4-2

| R¹ | R² | R³ |
|---|---|---|
| 2-adamantyl | 2-adamantyl | 2-tert-butylphenyl |
| 2-adamantyl | 2-adamantyl | 3-tert-butylphenyl |
| 2-adamantyl | 2-adamantyl | 4-tert-butylphenyl |
| 2-adamantyl | 2-adamantyl | 2-ethenylphenyl |
| 2-adamantyl | 2-adamantyl | 3-ethenylphenyl |
| 2-adamantyl | 2-adamantyl | 4-ethenylphenyl |
| 2-adamantyl | 2-adamantyl | 2-biphenylyl |
| 2-adamantyl | 2-adamantyl | 3-biphenylyl |
| 2-adamantyl | 2-adamantyl | 4-biphenylyl |
| 2-adamantyl | 2-adamantyl | 1-naphthyl |
| 2-adamantyl | 2-adamantyl | 2-naphthyl |
| 2-adamantyl | 2-adamantyl | 1,1'-binaphthalene-2-yl |
| 2-adamantyl | 2-adamantyl | 2-methoxyphenyl |
| 2-adamantyl | 2-adamantyl | 3-methoxyphenyl |
| 2-adamantyl | 2-adamantyl | 4-methoxyphenyl |
| 2-adamantyl | 2-adamantyl | 2-tert-butoxyphenyl |
| 2-adamantyl | 2-adamantyl | 3-tert-butoxyphenyl |
| 2-adamantyl | 2-adamantyl | 4-tert-butoxyphenyl |
| 2-adamantyl | 2-adamantyl | 2-dimethylaminophenyl |
| 2-adamantyl | 2-adamantyl | 3-dimethylaminophenyl |
| 2-adamantyl | 2-adamantyl | 4-dimethylaminophenyl |
| 2-adamantyl | 2-adamantyl | 2'-dimethylamino-2-biphenylyl |
| 2-adamantyl | 2-adamantyl | 8-dimethylamino-1-naphthyl |
| 2-adamantyl | 2-adamantyl | 2'-dimethylamino-1,1'-binaphthalene-2-yl |
| 2-adamantyl | 2-adamantyl | benzyl |
| 2-adamantyl | 2-adamantyl | 1-phenylethyl |
| 2-adamantyl | 2-adamantyl | 2-phenylethyl |
| 2-adamantyl | 2-adamantyl | 2-ethenylbenzyl |
| 2-adamantyl | 2-adamantyl | 3-ethenylbenzyl |
| 2-adamantyl | 2-adamantyl | 4-ethenylbenzyl |
| 2-adamantyl | 2-adamantyl | 4-(2-ethenylphenyl)butyl |
| 2-adamantyl | 2-adamantyl | 4-(3-ethenylphenyl)butyl |
| 2-adamantyl | 2-adamantyl | 4-(4-ethenylphenyl)butyl |
| 2-adamantyl | 2-adamantyl | vinyl |
| 2-adamantyl | 2-adamantyl | methallyl |
| 2-adamantyl | 2-adamantyl | 1-octenyl |
| 2-adamantyl | 2-adamantyl | ethynyl |
| 2-adamantyl | 2-adamantyl | 1-propynyl |
| 2-adamantyl | 2-adamantyl | 1-octynyl |
| 2-adamantyl | 2-adamantyl | allyl |
| 2-adamantyl | 2-adamantyl | 2-octenyl |

Tables 5 to 10 below show specific examples of the tetraarylborate compounds of Formula (IV):

$$M \cdot BAr_4 \qquad (IV)$$

that are used as starting compounds in the embodiment 2 of the first production process and the embodiment 2 of the second production process according to the present invention. The compounds are not limited thereto.

TABLE 9

Table 5

| Ar | M |
|---|---|
| phenyl | lithium |
| ortho-tolyl | lithium |
| meta-tolyl | lithium |
| para-tolyl | lithium |
| 2,3-xylyl | lithium |
| 2,4-xylyl | lithium |
| 2,5-xylyl | lithium |
| 2,6-xylyl | lithium |
| 3,4-xylyl | lithium |
| 3,5-xylyl | lithium |
| mesityl | lithium |
| 2-tert-butylphenyl | lithium |
| 3-tert-butylphenyl | lithium |
| 4-tert-butylphenyl | lithium |

TABLE 9-continued

Table 5

| Ar | M |
|---|---|
| 2-methoxyphenyl | lithium |
| 3-methoxyphenyl | lithium |
| 4-methoxyphenyl | lithium |
| 2-tert-butoxyphenyl | lithium |
| 3-tert-butoxyphenyl | lithium |
| 4-tert-butoxyphenyl | lithium |

TABLE 10

Table 6

| Ar | M |
|---|---|
| phenyl | sodium |
| ortho-tolyl | sodium |
| meta-tolyl | sodium |
| para-tolyl | sodium |
| 2,3-xylyl | sodium |
| 2,4-xylyl | sodium |
| 2,5-xylyl | sodium |
| 2,6-xylyl | sodium |
| 3,4-xylyl | sodium |
| 3,5-xylyl | sodium |
| mesityl | sodium |
| 2-tert-butylphenyl | sodium |
| 3-tert-butylphenyl | sodium |
| 4-tert-butylphenyl | sodium |
| 2-methoxyphenyl | sodium |
| 3-methoxyphenyl | sodium |
| 4-methoxyphenyl | sodium |
| 2-tert-butoxyphenyl | sodium |
| 3-tert-butoxyphenyl | sodium |
| 4-tert-butoxyphenyl | sodium |

TABLE 11

Table 7

| Ar | M |
|---|---|
| phenyl | potassium |
| ortho-tolyl | potassium |
| meta-tolyl | potassium |
| para-tolyl | potassium |
| 2,3-xylyl | potassium |
| 2,4-xylyl | potassium |
| 2,5-xylyl | potassium |
| 2,6-xylyl | potassium |
| 3,4-xylyl | potassium |
| 3,5-xylyl | potassium |
| mesityl | potassium |
| 2-tert-butylphenyl | potassium |
| 3-tert-butylphenyl | potassium |
| 4-tert-butylphenyl | potassium |
| 2-methoxyphenyl | potassium |
| 3-methoxyphenyl | potassium |
| 4-methoxyphenyl | potassium |
| 2-tert-butoxyphenyl | potassium |
| 3-tert-butoxyphenyl | potassium |
| 4-tert-butoxyphenyl | potassium |

TABLE 12

Table 8

| Ar | M |
|---|---|
| phenyl | magnesium chloride |
| ortho-tolyl | magnesium chloride |
| meta-tolyl | magnesium chloride |
| para-tolyl | magnesium chloride |

TABLE 12-continued

Table 8

| Ar | M |
|---|---|
| 2,3-xylyl | magnesium chloride |
| 2,4-xylyl | magnesium chloride |
| 2,5-xylyl | magnesium chloride |
| 2,6-xylyl | magnesium chloride |
| 3,4-xylyl | magnesium chloride |
| 3,5-xylyl | magnesium chloride |
| mesityl | magnesium chloride |
| 2-tert-butylphenyl | magnesium chloride |
| 3-tert-butylphenyl | magnesium chloride |
| 4-tert-butylphenyl | magnesium chloride |
| 2-methoxyphenyl | magnesium chloride |
| 3-methoxyphenyl | magnesium chloride |
| 4-methoxyphenyl | magnesium chloride |
| 2-tert-butoxyphenyl | magnesium chloride |
| 3-tert-butoxyphenyl | magnesium chloride |
| 4-tert-butoxyphenyl | magnesium chloride |

TABLE 13

Table 9

| Ar | M |
|---|---|
| phenyl | magnesium bromide |
| ortho-tolyl | magnesium bromide |
| meta-tolyl | magnesium bromide |
| para-tolyl | magnesium bromide |
| 2,3-xylyl | magnesium bromide |
| 2,4-xylyl | magnesium bromide |
| 2,5-xylyl | magnesium bromide |
| 2,6-xylyl | magnesium bromide |
| 3,4-xylyl | magnesium bromide |
| 3,5-xylyl | magnesium bromide |
| mesityl | magnesium bromide |
| 2-tert-butylphenyl | magnesium bromide |
| 3-tert-butylphenyl | magnesium bromide |
| 4-tert-butylphenyl | magnesium bromide |
| 2-methoxyphenyl | magnesium bromide |
| 3-methoxyphenyl | magnesium bromide |
| 4-methoxyphenyl | magnesium bromide |
| 2-tert-butoxyphenyl | magnesium bromide |
| 3-tert-butoxyphenyl | magnesium bromide |
| 4-tert-butoxyphenyl | magnesium bromide |

TABLE 14

Table 10

| Ar | M |
|---|---|
| phenyl | calcium chloride |
| ortho-tolyl | calcium chloride |
| meta-tolyl | calcium chloride |
| para-tolyl | calcium chloride |
| 2,3-xylyl | calcium chloride |
| 2,4-xylyl | calcium chloride |
| 2,5-xylyl | calcium chloride |
| 2,6-xylyl | calcium chloride |
| 3,4-xylyl | calcium chloride |
| 3,5-xylyl | calcium chloride |
| mesityl | calcium chloride |
| 2-tert-butylphenyl | calcium chloride |
| 3-tert-butylphenyl | calcium chloride |
| 4-tert-butylphenyl | calcium chloride |
| 2-methoxyphenyl | calcium chloride |
| 3-methoxyphenyl | calcium chloride |
| 4-methoxyphenyl | calcium chloride |
| 2-tert-butoxyphenyl | calcium chloride |
| 3-tert-butoxyphenyl | calcium chloride |
| 4-tert-butoxyphenyl | calcium chloride |

Tables 11-1 to 18-3 below show specific examples of the 5 novel phosphonium borate compounds represented by Formula (I):

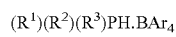 (I)

that are produced according to the present invention. The compounds are not limited thereto.

TABLE 15

Table 11-1

| R¹ | R² | R³ | Ar | Melting point (° C.) (Decomp. temp.) |
|---|---|---|---|---|
| tert-butyl | tert-butyl | hydrogen | phenyl | |
| tert-butyl | tert-butyl | methyl | phenyl | 192-196 |
| tert-butyl | tert-butyl | ethyl | phenyl | 174-188 |
| tert-butyl | tert-butyl | n-propyl | phenyl | |
| tert-butyl | tert-butyl | n-butyl | phenyl | 156-162 |
| tert-butyl | tert-butyl | isobutyl | phenyl | |
| tert-butyl | tert-butyl | n-pentyl | phenyl | |
| tert-butyl | tert-butyl | isopentyl | phenyl | |
| tert-butyl | tert-butyl | n-hexyl | phenyl | |
| tert-butyl | tert-butyl | 2-methyl-1-pentyl | phenyl | |
| tert-butyl | tert-butyl | 2,2-diethyl-1-ethyl | phenyl | |
| tert-butyl | tert-butyl | n-heptyl | phenyl | |
| tert-butyl | tert-butyl | n-octyl | phenyl | 108-113 |
| tert-butyl | tert-butyl | isopropyl | phenyl | |
| tert-butyl | tert-butyl | sec-butyl | phenyl | 184-187 |
| tert-butyl | tert-butyl | 2-pentyl | phenyl | |
| tert-butyl | tert-butyl | 3-pentyl | phenyl | |
| tert-butyl | tert-butyl | 2-hexyl | phenyl | |
| tert-butyl | tert-butyl | 3-hexyl | phenyl | |
| tert-butyl | tert-butyl | tert-amyl | phenyl | |
| tert-butyl | tert-butyl | 1,1-dimethylbutyl | phenyl | |
| tert-butyl | tert-butyl | 3-methyl-3-pentyl | phenyl | |
| tert-butyl | tert-butyl | 1,1,2-trimethylpropyl | phenyl | |
| tert-butyl | tert-butyl | 1-adamantyl | phenyl | |
| tert-butyl | tert-butyl | 2-methyl-1-adamantyl | phenyl | |
| tert-butyl | tert-butyl | cyclopropyl | phenyl | |
| tert-butyl | tert-butyl | cyclopentyl | phenyl | |
| tert-butyl | tert-butyl | cyclohexyl | phenyl | 171-178 |
| tert-butyl | tert-butyl | 1-methylcyclohexyl | phenyl | |
| tert-butyl | tert-butyl | 2-methylcyclohexyl | phenyl | |
| tert-butyl | tert-butyl | 2-adamantyl | phenyl | |
| tert-butyl | tert-butyl | 1-methyl-2-adamantyl | phenyl | |

TABLE 16

Table 11-2

| R¹ | R² | R³ | Ar | Melting point (° C.) (Decomp. temp.) |
|---|---|---|---|---|
| tert-butyl | tert-butyl | 2-methyl-2-adamantyl | phenyl | |
| tert-butyl | tert-butyl | phenyl | phenyl | 135-140 |
| tert-butyl | tert-butyl | ortho-tolyl | phenyl | |
| tert-butyl | tert-butyl | meta-tolyl | phenyl | |
| tert-butyl | tert-butyl | para-tolyl | phenyl | |
| tert-butyl | tert-butyl | 2,3-xylyl | phenyl | |
| tert-butyl | tert-butyl | 2,4-xylyl | phenyl | |
| tert-butyl | tert-butyl | 2,5-xylyl | phenyl | |
| tert-butyl | tert-butyl | 2,6-xylyl | phenyl | |
| tert-butyl | tert-butyl | 3,4-xylyl | phenyl | |
| tert-butyl | tert-butyl | 3,5-xylyl | phenyl | |
| tert-butyl | tert-butyl | mesityl | phenyl | |
| tert-butyl | tert-butyl | 2-tert-butylphenyl | phenyl | |
| tert-butyl | tert-butyl | 3-tert-butylphenyl | phenyl | |
| tert-butyl | tert-butyl | 4-tert-butylphenyl | phenyl | |
| tert-butyl | tert-butyl | 2-ethenylphenyl | phenyl | |
| tert-butyl | tert-butyl | 3-ethenylphenyl | phenyl | |
| tert-butyl | tert-butyl | 4-ethenylphenyl | phenyl | |

TABLE 16-continued

Table 11-2

| R¹ | R² | R³ | Ar | Melting point (° C.) (Decomp. temp.) |
|---|---|---|---|---|
| tert-butyl | tert-butyl | 2-biphenylyl | phenyl | 163-174 |
| tert-butyl | tert-butyl | 3-biphenylyl | phenyl | |
| tert-butyl | tert-butyl | 4-biphenylyl | phenyl | |
| tert-butyl | tert-butyl | 1-naphthyl | phenyl | 165-174 |
| tert-butyl | tert-butyl | 2-naphthyl | phenyl | |
| tert-butyl | tert-butyl | 1,1'-binaphthalene-2-yl | phenyl | |
| tert-butyl | tert-butyl | 2-methoxyphenyl | phenyl | |
| tert-butyl | tert-butyl | 3-methoxyphenyl | phenyl | |
| tert-butyl | tert-butyl | 4-methoxyphenyl | phenyl | |
| tert-butyl | tert-butyl | 2-tert-butoxyphenyl | phenyl | |
| tert-butyl | tert-butyl | 3-tert-butoxyphenyl | phenyl | |
| tert-butyl | tert-butyl | 4-tert-butoxyphenyl | phenyl | |

TABLE 17

Table 11-3

| R¹ | R² | R³ | Ar | Melting point (° C.) (Decomp. temp.) |
|---|---|---|---|---|
| tert-butyl | tert-butyl | 2-dimethyl-aminophenyl | phenyl | |
| tert-butyl | tert-butyl | 3-dimethyl-aminophenyl | phenyl | |
| tert-butyl | tert-butyl | 4-dimethyl-aminophenyl | phenyl | |
| tert-butyl | tert-butyl | 2'-dimethylamino-2-biphenylyl | phenyl | |
| tert-butyl | tert-butyl | 8-dimethylamino-1-naphthyl | phenyl | |
| tert-butyl | tert-butyl | 2'-dimethylamino-1,1'-binaphthalene-2-yl | phenyl | |
| tert-butyl | tert-butyl | benzyl | phenyl | 149-158 |
| tert-butyl | tert-butyl | 1-phenylethyl | phenyl | |
| tert-butyl | tert-butyl | 2-phenylethyl | phenyl | |
| tert-butyl | tert-butyl | 2-ethenylbenzyl | phenyl | |
| tert-butyl | tert-butyl | 3-ethenylbenzyl | phenyl | |
| tert-butyl | tert-butyl | 4-ethenylbenzyl | phenyl | 122-132 |
| tert-butyl | tert-butyl | 4-(2-ethenylphenyl)butyl | phenyl | |
| tert-butyl | tert-butyl | 4-(3-ethenylphenyl)butyl | phenyl | |
| tert-butyl | tert-butyl | 4-(4-ethenylphenyl)butyl | phenyl | |
| tert-butyl | tert-butyl | vinyl | phenyl | 253-261 |
| tert-butyl | tert-butyl | methallyl | phenyl | |
| tert-butyl | tert-butyl | 1-octenyl | phenyl | |
| tert-butyl | tert-butyl | ethynyl | phenyl | |
| tert-butyl | tert-butyl | 1-propynyl | phenyl | |
| tert-butyl | tert-butyl | 1-octynyl | phenyl | |
| tert-butyl | tert-butyl | allyl | phenyl | 148-160 |
| tert-butyl | tert-butyl | 2-octenyl | phenyl | |
| isopropyl | isopropyl | isopropyl | phenyl | 194-214 |
| n-butyl | cyclohexyl | cyclohexyl | phenyl | 175-180 |
| cyclopentyl | cyclopentyl | cyclopentyl | phenyl | 178-187 |

TABLE 18

Table 12-1

| R¹ | R² | R³ | Ar | Melting point (° C.) (Decomp. temp.) |
|---|---|---|---|---|
| tert-amyl | tert-amyl | hydrogen | phenyl | |
| tert-amyl | tert-amyl | methyl | phenyl | |
| tert-amyl | tert-amyl | ethyl | phenyl | |
| tert-amyl | tert-amyl | n-propyl | phenyl | |
| tert-amyl | tert-amyl | n-butyl | phenyl | |
| tert-amyl | tert-amyl | isobutyl | phenyl | |
| tert-amyl | tert-amyl | n-pentyl | phenyl | |
| tert-amyl | tert-amyl | isopentyl | phenyl | |
| tert-amyl | tert-amyl | n-hexyl | phenyl | |
| tert-amyl | tert-amyl | 2-methyl-1-pentyl | phenyl | |
| tert-amyl | tert-amyl | 2,2-diethyl-1-ethyl | phenyl | |
| tert-amyl | tert-amyl | n-heptyl | phenyl | |
| tert-amyl | tert-amyl | n-octyl | phenyl | |
| tert-amyl | tert-amyl | isopropyl | phenyl | |
| tert-amyl | tert-amyl | sec-butyl | phenyl | |
| tert-amyl | tert-amyl | 2-pentyl | phenyl | |
| tert-amyl | tert-amyl | 3-pentyl | phenyl | |
| tert-amyl | tert-amyl | 2-hexyl | phenyl | |
| tert-amyl | tert-amyl | 3-hexyl | phenyl | |
| tert-amyl | tert-amyl | tert-butyl | phenyl | |
| tert-amyl | tert-amyl | tert-amyl | phenyl | |
| tert-amyl | tert-amyl | 1,1-dimethylbutyl | phenyl | |
| tert-amyl | tert-amyl | 3-methyl-3-pentyl | phenyl | |
| tert-amyl | tert-amyl | 1,1,2-trimethylpropyl | phenyl | |
| tert-amyl | tert-amyl | 1-adamantyl | phenyl | |
| tert-amyl | tert-amyl | 2-methyl-1-adamantyl | phenyl | |
| tert-amyl | tert-amyl | cyclopropyl | phenyl | |
| tert-amyl | tert-amyl | cyclopentyl | phenyl | |
| tert-amyl | tert-amyl | cyclohexyl | phenyl | |
| tert-amyl | tert-amyl | 1-methylcyclohexyl | phenyl | |
| tert-amyl | tert-amyl | 2-methylcyclohexyl | phenyl | |
| tert-amyl | tert-amyl | 2-adamantyl | phenyl | |
| tert-amyl | tert-amyl | 1-methyl-2-adamantyl | phenyl | |
| tert-amyl | tert-amyl | 2-methyl-2-adamantyl | phenyl | |

TABLE 19

Table 12-2

| R¹ | R² | R³ | Ar | Melting point (° C.) (Decomp. temp.) |
|---|---|---|---|---|
| tert-amyl | tert-amyl | phenyl | phenyl | |
| tert-amyl | tert-amyl | ortho-tolyl | phenyl | |
| tert-amyl | tert-amyl | meta-tolyl | phenyl | |
| tert-amyl | tert-amyl | para-tolyl | phenyl | |
| tert-amyl | tert-amyl | 2,3-xylyl | phenyl | |
| tert-amyl | tert-amyl | 2,4-xylyl | phenyl | |
| tert-amyl | tert-amyl | 2,5-xylyl | phenyl | |
| tert-amyl | tert-amyl | 2,6-xylyl | phenyl | |
| tert-amyl | tert-amyl | 3,4-xylyl | phenyl | |
| tert-amyl | tert-amyl | 3,5-xylyl | phenyl | |
| tert-amyl | tert-amyl | mesityl | phenyl | |
| tert-amyl | tert-amyl | 2-tert-butylphenyl | phenyl | |
| tert-amyl | tert-amyl | 3-tert-butylphenyl | phenyl | |
| tert-amyl | tert-amyl | 4-tert-butylphenyl | phenyl | |
| tert-amyl | tert-amyl | 2-ethenylphenyl | phenyl | |
| tert-amyl | tert-amyl | 3-ethenylphenyl | phenyl | |
| tert-amyl | tert-amyl | 4-ethenylphenyl | phenyl | |
| tert-amyl | tert-amyl | 2-biphenylyl | phenyl | |
| tert-amyl | tert-amyl | 3-biphenylyl | phenyl | |
| tert-amyl | tert-amyl | 4-biphenylyl | phenyl | |
| tert-amyl | tert-amyl | 1-naphthyl | phenyl | |
| tert-amyl | tert-amyl | 2-naphthyl | phenyl | |
| tert-amyl | tert-amyl | 1,1'-binaphthalene-2-yl | phenyl | |
| tert-amyl | tert-amyl | 2-methoxyphenyl | phenyl | |
| tert-amyl | tert-amyl | 3-methoxyphenyl | phenyl | |

TABLE 19-continued

Table 12-2

| R¹ | R² | R³ | Ar | Melting point (° C.) (Decomp. temp.) |
|---|---|---|---|---|
| tert-amyl | tert-amyl | 4-methoxyphenyl | phenyl | |
| tert-amyl | tert-amyl | 2-tert-butoxyphenyl | phenyl | |
| tert-amyl | tert-amyl | 3-tert-butoxyphenyl | phenyl | |
| tert-amyl | tert-amyl | 4-tert-butoxyphenyl | phenyl | |
| tert-amyl | tert-amyl | 2-dimethylaminophenyl | phenyl | |

TABLE 20

Table 12-3

| R¹ | R² | R³ | Ar | Melting point (° C.) (Decomp. temp.) |
|---|---|---|---|---|
| tert-amyl | tert-amyl | 3-dimethylaminophenyl | phenyl | |
| tert-amyl | tert-amyl | 4-dimethylaminophenyl | phenyl | |
| tert-amyl | tert-amyl | 2'-dimethylamino-2-biphenylyl | phenyl | |
| tert-amyl | tert-amyl | 8-dimethylamino-1-naphthyl | phenyl | |
| tert-amyl | tert-amyl | 2'-dimethylamino-1,1'-binaphthalene-2-yl | phenyl | |
| tert-amyl | tert-amyl | benzyl | phenyl | |
| tert-amyl | tert-amyl | 1-phenylethyl | phenyl | |
| tert-amyl | tert-amyl | 2-phenylethyl | phenyl | |
| tert-amyl | tert-amyl | 2-ethenylbenzyl | phenyl | |
| tert-amyl | tert-amyl | 3-ethenylbenzyl | phenyl | |
| tert-amyl | tert-amyl | 4-ethenylbenzyl | phenyl | |
| tert-amyl | tert-amyl | 4-(2-ethenylphenyl)butyl | phenyl | |
| tert-amyl | tert-amyl | 4-(3-ethenylphenyl)butyl | phenyl | |
| tert-amyl | tert-amyl | 4-(4-ethenylphenyl)butyl | phenyl | |
| tert-amyl | tert-amyl | vinyl | phenyl | |
| tert-amyl | tert-amyl | methallyl | phenyl | |
| tert-amyl | tert-amyl | 1-octenyl | phenyl | |
| tert-amyl | tert-amyl | ethynyl | phenyl | |
| tert-amyl | tert-amyl | 1-propynyl | phenyl | |
| tert-amyl | tert-amyl | 1-octynyl | phenyl | |
| tert-amyl | tert-amyl | allyl | phenyl | |
| tert-amyl | tert-amyl | 2-octenyl | phenyl | |

TABLE 21

Table 13-1

| R¹ | R² | R³ | Ar | Melting point (° C.) (Decomp. temp.) |
|---|---|---|---|---|
| 1-adamantyl | 1-adamantyl | hydrogen | phenyl | |
| 1-adamantyl | 1-adamantyl | methyl | phenyl | |
| 1-adamantyl | 1-adamantyl | ethyl | phenyl | |
| 1-adamantyl | 1-adamantyl | n-propyl | phenyl | |
| 1-adamantyl | 1-adamantyl | n-butyl | phenyl | |
| 1-adamantyl | 1-adamantyl | isobutyl | phenyl | |
| 1-adamantyl | 1-adamantyl | n-pentyl | phenyl | |
| 1-adamantyl | 1-adamantyl | isopentyl | phenyl | |
| 1-adamantyl | 1-adamantyl | n-hexyl | phenyl | |
| 1-adamantyl | 1-adamantyl | 2-methyl-1-pentyl | phenyl | |
| 1-adamantyl | 1-adamantyl | 2,2-diethyl-1-ethyl | phenyl | |
| 1-adamantyl | 1-adamantyl | n-heptyl | phenyl | |
| 1-adamantyl | 1-adamantyl | n-octyl | phenyl | |
| 1-adamantyl | 1-adamantyl | isopropyl | phenyl | |

TABLE 21-continued

Table 13-1

| R¹ | R² | R³ | Ar | Melting point (° C.) (Decomp. temp.) |
|---|---|---|---|---|
| 1-adamantyl | 1-adamantyl | sec-butyl | phenyl | |
| 1-adamantyl | 1-adamantyl | 2-pentyl | phenyl | |
| 1-adamantyl | 1-adamantyl | 3-pentyl | phenyl | |
| 1-adamantyl | 1-adamantyl | 2-hexyl | phenyl | |
| 1-adamantyl | 1-adamantyl | 3-hexyl | phenyl | |
| 1-adamantyl | 1-adamantyl | tert-butyl | phenyl | |
| 1-adamantyl | 1-adamantyl | tert-amyl | phenyl | |
| 1-adamantyl | 1-adamantyl | 1,1-dimethylbutyl | phenyl | |
| 1-adamantyl | 1-adamantyl | 3-methyl-3-pentyl | phenyl | |
| 1-adamantyl | 1-adamantyl | 1,1,2-trimethylpropyl | phenyl | |
| 1-adamantyl | 1-adamantyl | 1-adamantyl | phenyl | |
| 1-adamantyl | 1-adamantyl | 2-methyl-1-adamantyl | phenyl | |
| 1-adamantyl | 1-adamantyl | cyclopropyl | phenyl | |
| 1-adamantyl | 1-adamantyl | cyclopentyl | phenyl | |
| 1-adamantyl | 1-adamantyl | cyclohexyl | phenyl | |
| 1-adamantyl | 1-adamantyl | 1-methylcyclohexyl | phenyl | |
| 1-adamantyl | 1-adamantyl | 2-methylcyclohexyl | phenyl | |
| 1-adamantyl | 1-adamantyl | 2-adamantyl | phenyl | |
| 1-adamantyl | 1-adamantyl | 1-methyl-2-adamantyl | phenyl | |

TABLE 22

Table 13-2

| R¹ | R² | R³ | Ar | Melting point (° C.) (Decomp. temp.) |
|---|---|---|---|---|
| 1-adamantyl | 1-adamantyl | 2-methyl-2-adamantyl | phenyl | |
| 1-adamantyl | 1-adamantyl | phenyl | phenyl | |
| 1-adamantyl | 1-adamantyl | ortho-tolyl | phenyl | |
| 1-adamantyl | 1-adamantyl | meta-tolyl | phenyl | |
| 1-adamantyl | 1-adamantyl | para-tolyl | phenyl | |
| 1-adamantyl | 1-adamantyl | 2,3-xylyl | phenyl | |
| 1-adamantyl | 1-adamantyl | 2,4-xylyl | phenyl | |
| 1-adamantyl | 1-adamantyl | 2,5-xylyl | phenyl | |
| 1-adamantyl | 1-adamantyl | 2,6-xylyl | phenyl | |
| 1-adamantyl | 1-adamantyl | 3,4-xylyl | phenyl | |
| 1-adamantyl | 1-adamantyl | 3,5-xylyl | phenyl | |
| 1-adamantyl | 1-adamantyl | mesityl | phenyl | |
| 1-adamantyl | 1-adamantyl | 2-tert-butylphenyl | phenyl | |
| 1-adamantyl | 1-adamantyl | 3-tert-butylphenyl | phenyl | |
| 1-adamantyl | 1-adamantyl | 4-tert-butylphenyl | phenyl | |
| 1-adamantyl | 1-adamantyl | 2-ethenylphenyl | phenyl | |
| 1-adamantyl | 1-adamantyl | 3-ethenylphenyl | phenyl | |
| 1-adamantyl | 1-adamantyl | 4-ethenylphenyl | phenyl | |
| 1-adamantyl | 1-adamantyl | 2-biphenylyl | phenyl | |
| 1-adamantyl | 1-adamantyl | 3-biphenylyl | phenyl | |
| 1-adamantyl | 1-adamantyl | 4-biphenylyl | phenyl | |
| 1-adamantyl | 1-adamantyl | 1-naphthyl | phenyl | |
| 1-adamantyl | 1-adamantyl | 2-naphthyl | phenyl | |
| 1-adamantyl | 1-adamantyl | 1,1'-binaphthalene-2-yl | phenyl | |
| 1-adamantyl | 1-adamantyl | 2-methoxyphenyl | phenyl | |
| 1-adamantyl | 1-adamantyl | 3-methoxyphenyl | phenyl | |
| 1-adamantyl | 1-adamantyl | 4-methoxyphenyl | phenyl | |
| 1-adamantyl | 1-adamantyl | 2-tert-butoxyphenyl | phenyl | |
| 1-adamantyl | 1-adamantyl | 3-tert-butoxyphenyl | phenyl | |
| 1-adamantyl | 1-adamantyl | 4-tert-butoxyphenyl | phenyl | |

TABLE 23

Table 13-3

| R¹ | R² | R³ | Ar | Melting point (° C.) (Decomp. temp.) |
|---|---|---|---|---|
| 1-adamantyl | 1-adamantyl | 2-dimethyl-aminophenyl | phenyl | |
| 1-adamantyl | 1-adamantyl | 3-dimethyl-aminophenyl | phenyl | |
| 1-adamantyl | 1-adamantyl | 4-dimethyl-aminophenyl | phenyl | |
| 1-adamantyl | 1-adamantyl | 2'-dimethylamino-2-biphenylyl | phenyl | |
| 1-adamantyl | 1-adamantyl | 8-dimethylamino-1-naphthyl | phenyl | |
| 1-adamantyl | 1-adamantyl | 2'-dimethylamino-1,1'-binaphthalene-2-yl | phenyl | |
| 1-adamantyl | 1-adamantyl | benzyl | phenyl | |
| 1-adamantyl | 1-adamantyl | 1-phenylethyl | phenyl | |
| 1-adamantyl | 1-adamantyl | 2-phenylethyl | phenyl | |
| 1-adamantyl | 1-adamantyl | 2-ethenylbenzyl | phenyl | |
| 1-adamantyl | 1-adamantyl | 3-ethenylbenzyl | phenyl | |
| 1-adamantyl | 1-adamantyl | 4-ethenylbenzyl | phenyl | |
| 1-adamantyl | 1-adamantyl | 4-(2-ethenyl-phenyl)butyl | phenyl | |
| 1-adamantyl | 1-adamantyl | 4-(3-ethenyl-phenyl)butyl | phenyl | |
| 1-adamantyl | 1-adamantyl | 4-(4-ethenyl-phenyl)butyl | phenyl | |
| 1-adamantyl | 1-adamantyl | vinyl | phenyl | |
| 1-adamantyl | 1-adamantyl | methallyl | phenyl | |
| 1-adamantyl | 1-adamantyl | 1-octenyl | phenyl | |
| 1-adamantyl | 1-adamantyl | ethynyl | phenyl | |
| 1-adamantyl | 1-adamantyl | 1-propynyl | phenyl | |
| 1-adamantyl | 1-adamantyl | 1-octynyl | phenyl | |
| 1-adamantyl | 1-adamantyl | allyl | phenyl | |
| 1-adamantyl | 1-adamantyl | 2-octenyl | phenyl | |

TABLE 24

Table 14-1

| R¹ | R² | R³ | Ar | Melting point (° C.) (Decomp. temp.) |
|---|---|---|---|---|
| 2-adamantyl | 2-adamantyl | hydrogen | phenyl | |
| 2-adamantyl | 2-adamantyl | methyl | phenyl | |
| 2-adamantyl | 2-adamantyl | ethyl | phenyl | |
| 2-adamantyl | 2-adamantyl | n-propyl | phenyl | |
| 2-adamantyl | 2-adamantyl | n-butyl | phenyl | |
| 2-adamantyl | 2-adamantyl | isobutyl | phenyl | |
| 2-adamantyl | 2-adamantyl | n-pentyl | phenyl | |
| 2-adamantyl | 2-adamantyl | isopentyl | phenyl | |
| 2-adamantyl | 2-adamantyl | n-hexyl | phenyl | |
| 2-adamantyl | 2-adamantyl | 2-methyl-1-pentyl | phenyl | |
| 2-adamantyl | 2-adamantyl | 2,2-diethyl-1-ethyl | phenyl | |
| 2-adamantyl | 2-adamantyl | n-heptyl | phenyl | |
| 2-adamantyl | 2-adamantyl | n-octyl | phenyl | |
| 2-adamantyl | 2-adamantyl | isopropyl | phenyl | |
| 2-adamantyl | 2-adamantyl | sec-butyl | phenyl | |
| 2-adamantyl | 2-adamantyl | 2-pentyl | phenyl | |
| 2-adamantyl | 2-adamantyl | 3-pentyl | phenyl | |
| 2-adamantyl | 2-adamantyl | 2-hexyl | phenyl | |
| 2-adamantyl | 2-adamantyl | 3-hexyl | phenyl | |
| 2-adamantyl | 2-adamantyl | tert-butyl | phenyl | |
| 2-adamantyl | 2-adamantyl | tert-amyl | phenyl | |
| 2-adamantyl | 2-adamantyl | 1,1-dimethylbutyl | phenyl | |
| 2-adamantyl | 2-adamantyl | 3-methyl-3-pentyl | phenyl | |
| 2-adamantyl | 2-adamantyl | 1,1,2-trimethylpropyl | phenyl | |
| 2-adamantyl | 2-adamantyl | 1-adamantyl | phenyl | |

TABLE 24-continued

Table 14-1

| R$^1$ | R$^2$ | R$^3$ | Ar | Melting point (° C.) (Decomp. temp.) |
|---|---|---|---|---|
| 2-adamantyl | 2-adamantyl | 2-methyl-1-adamantyl | phenyl | |
| 2-adamantyl | 2-adamantyl | cyclopropyl | phenyl | |
| 2-adamantyl | 2-adamantyl | cyclopentyl | phenyl | |
| 2-adamantyl | 2-adamantyl | cyclohexyl | phenyl | |
| 2-adamantyl | 2-adamantyl | 1-methylcyclohexyl | phenyl | |
| 2-adamantyl | 2-adamantyl | 2-methylcyclohexyl | phenyl | |
| 2-adamantyl | 2-adamantyl | 2-adamantyl | phenyl | |
| 2-adamantyl | 2-adamantyl | 1-methyl-2-adamantyl | phenyl | |
| 2-adamantyl | 2-adamantyl | 2-methyl-2-adamantyl | phenyl | |
| 2-adamantyl | 2-adamantyl | phenyl | phenyl | |

TABLE 25

Table 14-2

| R$^1$ | R$^2$ | R$^3$ | Ar | Melting point (° C.) (Decomp. temp.) |
|---|---|---|---|---|
| 2-adamantyl | 2-adamantyl | ortho-tolyl | phenyl | |
| 2-adamantyl | 2-adamantyl | meta-tolyl | phenyl | |
| 2-adamantyl | 2-adamantyl | para-tolyl | phenyl | |
| 2-adamantyl | 2-adamantyl | 2,3-xylyl | phenyl | |
| 2-adamantyl | 2-adamantyl | 2,4-xylyl | phenyl | |
| 2-adamantyl | 2-adamantyl | 2,5-xylyl | phenyl | |
| 2-adamantyl | 2-adamantyl | 2,6-xylyl | phenyl | |
| 2-adamantyl | 2-adamantyl | 3,4-xylyl | phenyl | |
| 2-adamantyl | 2-adamantyl | 3,5-xylyl | phenyl | |
| 2-adamantyl | 2-adamantyl | mesityl | phenyl | |
| 2-adamantyl | 2-adamantyl | 2-tert-butylphenyl | phenyl | |
| 2-adamantyl | 2-adamantyl | 3-tert-butylphenyl | phenyl | |
| 2-adamantyl | 2-adamantyl | 4-tert-butylphenyl | phenyl | |
| 2-adamantyl | 2-adamantyl | 2-ethenylphenyl | phenyl | |
| 2-adamantyl | 2-adamantyl | 3-ethenylphenyl | phenyl | |
| 2-adamantyl | 2-adamantyl | 4-ethenylphenyl | phenyl | |
| 2-adamantyl | 2-adamantyl | 2-biphenylyl | phenyl | |
| 2-adamantyl | 2-adamantyl | 3-biphenylyl | phenyl | |
| 2-adamantyl | 2-adamantyl | 4-biphenylyl | phenyl | |
| 2-adamantyl | 2-adamantyl | 1-naphthyl | phenyl | |
| 2-adamantyl | 2-adamantyl | 2-naphthyl | phenyl | |
| 2-adamantyl | 2-adamantyl | 1,1'-binaphthalene-2-yl | phenyl | |
| 2-adamantyl | 2-adamantyl | 2-methoxyphenyl | phenyl | |
| 2-adamantyl | 2-adamantyl | 3-methoxyphenyl | phenyl | |
| 2-adamantyl | 2-adamantyl | 4-methoxyphenyl | phenyl | |
| 2-adamantyl | 2-adamantyl | 2-tert-butoxyphenyl | phenyl | |
| 2-adamantyl | 2-adamantyl | 3-tert-butoxyphenyl | phenyl | |
| 2-adamantyl | 2-adamantyl | 4-tert-butoxyphenyl | phenyl | |
| 2-adamantyl | 2-adamantyl | 2-dimethylaminophenyl | phenyl | |
| 2-adamantyl | 2-adamantyl | 3-dimethylaminophenyl | phenyl | |

TABLE 26

Table 14-3

| R$^1$ | R$^2$ | R$^3$ | Ar | Melting point (° C.) (Decomp. temp.) |
|---|---|---|---|---|
| 2-adamantyl | 2-adamantyl | 4-dimethylaminophenyl | phenyl | |
| 2-adamantyl | 2-adamantyl | 2'-dimethylamino-2-biphenylyl | phenyl | |
| 2-adamantyl | 2-adamantyl | 8-dimethylamino-1-naphthyl | phenyl | |
| 2-adamantyl | 2-adamantyl | 2'-dimethylamino-1,1'-binaphthalene-2-yl | phenyl | |
| 2-adamantyl | 2-adamantyl | benzyl | phenyl | |
| 2-adamantyl | 2-adamantyl | 1-phenylethyl | phenyl | |
| 2-adamantyl | 2-adamantyl | 2-phenylethyl | phenyl | |
| 2-adamantyl | 2-adamantyl | 2-ethenylbenzyl | phenyl | |
| 2-adamantyl | 2-adamantyl | 3-ethenylbenzyl | phenyl | |
| 2-adamantyl | 2-adamantyl | 4-ethenylbenzyl | phenyl | |
| 2-adamantyl | 2-adamantyl | 4-(2-ethenyl-phenyl)butyl | phenyl | |
| 2-adamantyl | 2-adamantyl | 4-(3-ethenyl-phenyl)butyl | phenyl | |
| 2-adamantyl | 2-adamantyl | 4-(4-ethenyl-phenyl)butyl | phenyl | |
| 2-adamantyl | 2-adamantyl | vinyl | phenyl | |
| 2-adamantyl | 2-adamantyl | methallyl | phenyl | |
| 2-adamantyl | 2-adamantyl | 1-octenyl | phenyl | |
| 2-adamantyl | 2-adamantyl | ethynyl | phenyl | |
| 2-adamantyl | 2-adamantyl | 1-propynyl | phenyl | |
| 2-adamantyl | 2-adamantyl | 1-octynyl | phenyl | |
| 2-adamantyl | 2-adamantyl | allyl | phenyl | |
| 2-adamantyl | 2-adamantyl | 2-octenyl | phenyl | |

TABLE 27

Table 15-1

| R$^1$ | R$^2$ | R$^3$ | Ar | Melting point (° C.) (Decomp. temp.) |
|---|---|---|---|---|
| tert-butyl | tert-butyl | hydrogen | para-tolyl | |
| tert-butyl | tert-butyl | methyl | para-tolyl | 157–166 |
| tert-butyl | tert-butyl | ethyl | para-tolyl | |
| tert-butyl | tert-butyl | n-propyl | para-tolyl | |
| tert-butyl | tert-butyl | n-butyl | para-tolyl | |
| tert-butyl | tert-butyl | isobutyl | para-tolyl | |
| tert-butyl | tert-butyl | n-pentyl | para-tolyl | |
| tert-butyl | tert-butyl | isopentyl | para-tolyl | |
| tert-butyl | tert-butyl | n-hexyl | para-tolyl | |
| tert-butyl | tert-butyl | 2-methyl-1-pentyl | para-tolyl | |
| tert-butyl | tert-butyl | 2,2-diethyl-1-ethyl | para-tolyl | |
| tert-butyl | tert-butyl | n-heptyl | para-tolyl | |
| tert-butyl | tert-butyl | n-octyl | para-tolyl | |
| tert-butyl | tert-butyl | isopropyl | para-tolyl | |
| tert-butyl | tert-butyl | sec-butyl | para-tolyl | |
| tert-butyl | tert-butyl | 2-pentyl | para-tolyl | |
| tert-butyl | tert-butyl | 3-pentyl | para-tolyl | |
| tert-butyl | tert-butyl | 2-hexyl | para-tolyl | |
| tert-butyl | tert-butyl | 3-hexyl | para-tolyl | |
| tert-butyl | tert-butyl | tert-butyl | para-tolyl | 179–201 |
| tert-butyl | tert-butyl | tert-amyl | para-tolyl | |
| tert-butyl | tert-butyl | 1,1-dimethylbutyl | para-tolyl | |
| tert-butyl | tert-butyl | 3-methyl-3-pentyl | para-tolyl | |
| tert-butyl | tert-butyl | 1,1,2-trimethylpropyl | para-tolyl | |
| tert-butyl | tert-butyl | 1-adamantyl | para-tolyl | |
| tert-butyl | tert-butyl | 2-methyl-1-adamantyl | para-tolyl | |
| tert-butyl | tert-butyl | cyclopropyl | para-tolyl | |
| tert-butyl | tert-butyl | cyclopentyl | para-tolyl | |
| tert-butyl | tert-butyl | cyclohexyl | para-tolyl | |
| tert-butyl | tert-butyl | 1-methylcyclohexyl | para-tolyl | |
| tert-butyl | tert-butyl | 2-methylcyclohexyl | para-tolyl | |
| tert-butyl | tert-butyl | 2-adamantyl | para-tolyl | |
| tert-butyl | tert-butyl | 1-methyl-2-adamantyl | para-tolyl | |
| tert-butyl | tert-butyl | 2-methyl-2-adamantyl | para-tolyl | |
| tert-butyl | tert-butyl | phenyl | para-tolyl | |

TABLE 28

Table 15-2

| R$^1$ | R$^2$ | R$^3$ | Ar | Melting point (° C.) (Decomp. temp.) |
|---|---|---|---|---|
| tert-butyl | tert-butyl | ortho-tolyl | para-tolyl | |
| tert-butyl | tert-butyl | meta-tolyl | para-tolyl | |
| tert-butyl | tert-butyl | para-tolyl | para-tolyl | |
| tert-butyl | tert-butyl | 2,3-xylyl | para-tolyl | |
| tert-butyl | tert-butyl | 2,4-xylyl | para-tolyl | |
| tert-butyl | tert-butyl | 2,5-xylyl | para-tolyl | |
| tert-butyl | tert-butyl | 2,6-xylyl | para-tolyl | |
| tert-butyl | tert-butyl | 3,4-xylyl | para-tolyl | |
| tert-butyl | tert-butyl | 3,5-xylyl | para-tolyl | |
| tert-butyl | tert-butyl | mesityl | para-tolyl | |
| tert-butyl | tert-butyl | 2-tert-butylphenyl | para-tolyl | |
| tert-butyl | tert-butyl | 3-tert-butylphenyl | para-tolyl | |
| tert-butyl | tert-butyl | 4-tert-butylphenyl | para-tolyl | |
| tert-butyl | tert-butyl | 2-ethenylphenyl | para-tolyl | |
| tert-butyl | tert-butyl | 3-ethenylphenyl | para-tolyl | |
| tert-butyl | tert-butyl | 4-ethenylphenyl | para-tolyl | |
| tert-butyl | tert-butyl | 2-biphenylyl | para-tolyl | |
| tert-butyl | tert-butyl | 3-biphenylyl | para-tolyl | |
| tert-butyl | tert-butyl | 4-biphenylyl | para-tolyl | |
| tert-butyl | tert-butyl | 1-naphthyl | para-tolyl | |
| tert-butyl | tert-butyl | 2-naphthyl | para-tolyl | |
| tert-butyl | tert-butyl | 1,1'-binaphthalene-2-yl | para-tolyl | |
| tert-butyl | tert-butyl | 2-methoxyphenyl | para-tolyl | |
| tert-butyl | tert-butyl | 3-methoxyphenyl | para-tolyl | |
| tert-butyl | tert-butyl | 4-methoxyphenyl | para-tolyl | |
| tert-butyl | tert-butyl | 2-tert-butoxyphenyl | para-tolyl | |
| tert-butyl | tert-butyl | 3-tert-butoxyphenyl | para-tolyl | |
| tert-butyl | tert-butyl | 4-tert-butoxyphenyl | para-tolyl | |
| tert-butyl | tert-butyl | 2-dimethylaminophenyl | para-tolyl | |
| tert-butyl | tert-butyl | 3-dimethylaminophenyl | para-tolyl | |

TABLE 29

Table 15-3

| R$^1$ | R$^2$ | R$^3$ | Ar | Melting point (° C.) (Decomp. temp.) |
|---|---|---|---|---|
| tert-butyl | tert-butyl | 4-dimethyl-aminophenyl | para-tolyl | |
| tert-butyl | tert-butyl | 2'-dimethylamino-2-biphenylyl | para-tolyl | |
| tert-butyl | tert-butyl | 8-dimethylamino-1-naphthyl | para-tolyl | |
| tert-butyl | tert-butyl | 2'-dimethylamino-1,1'-binaphthalene-2-yl | para-tolyl | |
| tert-butyl | tert-butyl | benzyl | para-tolyl | |
| tert-butyl | tert-butyl | 1-phenylethyl | para-tolyl | |
| tert-butyl | tert-butyl | 2-phenylethyl | para-tolyl | |
| tert-butyl | tert-butyl | 2-ethenylbenzyl | para-tolyl | |
| tert-butyl | tert-butyl | 3-ethenylbenzyl | para-tolyl | |
| tert-butyl | tert-butyl | 4-ethenylbenzyl | para-tolyl | |
| tert-butyl | tert-butyl | 4-(2-ethenyl-phenyl)butyl | para-tolyl | |
| tert-butyl | tert-butyl | 4-(3-ethenyl-phenyl)butyl | para-tolyl | |
| tert-butyl | tert-butyl | 4-(4-ethenyl-phenyl)butyl | para-tolyl | |
| tert-butyl | tert-butyl | vinyl | para-tolyl | |
| tert-butyl | tert-butyl | methallyl | para-tolyl | |
| tert-butyl | tert-butyl | 1-octenyl | para-tolyl | |
| tert-butyl | tert-butyl | ethynyl | para-tolyl | |
| tert-butyl | tert-butyl | 1-propynyl | para-tolyl | |
| tert-butyl | tert-butyl | 1-octynyl | para-tolyl | |

TABLE 29-continued

Table 15-3

| R$^1$ | R$^2$ | R$^3$ | Ar | Melting point (° C.) (Decomp. temp.) |
|---|---|---|---|---|
| tert-butyl | tert-butyl | allyl | para-tolyl | |
| tert-butyl | tert-butyl | 2-octenyl | para-tolyl | |
| isopropyl | isopropyl | isopropyl | para-tolyl | |
| n-butyl | cyclohexyl | cyclohexyl | para-tolyl | |
| cyclopentyl | cyclopentyl | cyclopentyl | para-tolyl | |
| cyclohexyl | cyclohexyl | cyclohexyl | para-tolyl | 129–131 |

TABLE 30

Table 16-1

| R$^1$ | R$^2$ | R$^3$ | Ar | Melting point (° C.) (Decomp. temp.) |
|---|---|---|---|---|
| tert-amyl | tert-amyl | hydrogen | para-tolyl | |
| tert-amyl | tert-amyl | methyl | para-tolyl | |
| tert-amyl | tert-amyl | ethyl | para-tolyl | |
| tert-amyl | tert-amyl | n-propyl | para-tolyl | |
| tert-amyl | tert-amyl | n-butyl | para-tolyl | |
| tert-amyl | tert-amyl | isobutyl | para-tolyl | |
| tert-amyl | tert-amyl | n-pentyl | para-tolyl | |
| tert-amyl | tert-amyl | isopentyl | para-tolyl | |
| tert-amyl | tert-amyl | n-hexyl | para-tolyl | |
| tert-amyl | tert-amyl | 2-methyl-1-pentyl | para-tolyl | |
| tert-amyl | tert-amyl | 2,2-diethyl-1-ethyl | para-tolyl | |
| tert-amyl | tert-amyl | n-heptyl | para-tolyl | |
| tert-amyl | tert-amyl | n-octyl | para-tolyl | |
| tert-amyl | tert-amyl | isopropyl | para-tolyl | |
| tert-amyl | tert-amyl | sec-butyl | para-tolyl | |
| tert-amyl | tert-amyl | 2-pentyl | para-tolyl | |
| tert-amyl | tert-amyl | 3-pentyl | para-tolyl | |
| tert-amyl | tert-amyl | 2-hexyl | para-tolyl | |
| tert-amyl | tert-amyl | 3-hexyl | para-tolyl | |
| tert-amyl | tert-amyl | tert-butyl | para-tolyl | |
| tert-amyl | tert-amyl | tert-amyl | para-tolyl | |
| tert-amyl | tert-amyl | 1,1-dimethylbutyl | para-tolyl | |
| tert-amyl | tert-amyl | 3-methyl-3-pentyl | para-tolyl | |
| tert-amyl | tert-amyl | 1,1,2-trimethylpropyl | para-tolyl | |
| tert-amyl | tert-amyl | 1-adamantyl | para-tolyl | |
| tert-amyl | tert-amyl | 2-methyl-1-adamantyl | para-tolyl | |
| tert-amyl | tert-amyl | cyclopropyl | para-tolyl | |
| tert-amyl | tert-amyl | cyclopentyl | para-tolyl | |
| tert-amyl | tert-amyl | cyclohexyl | para-tolyl | |
| tert-amyl | tert-amyl | 1-methylcyclohexyl | para-tolyl | |
| tert-amyl | tert-amyl | 2-methylcyclohexyl | para-tolyl | |
| tert-amyl | tert-amyl | 2-adamantyl | para-tolyl | |
| tert-amyl | tert-amyl | 1-methyl-2-adamantyl | para-tolyl | |
| tert-amyl | tert-amyl | 2-methyl-2-adamantyl | para-tolyl | |
| tert-amyl | tert-amyl | phenyl | para-tolyl | |

TABLE 31

Table 16-2

| R$^1$ | R$^2$ | R$^3$ | Ar | Melting point (° C.) (Decomp. temp.) |
|---|---|---|---|---|
| tert-amyl | tert-amyl | ortho-tolyl | para-tolyl | |
| tert-amyl | tert-amyl | meta-tolyl | para-tolyl | |
| tert-amyl | tert-amyl | para-tolyl | para-tolyl | |
| tert-amyl | tert-amyl | 2,3-xylyl | para-tolyl | |

TABLE 31-continued

Table 16-2

| R¹ | R² | R³ | Ar | Melting point (° C.) (Decomp. temp.) |
|---|---|---|---|---|
| tert-amyl | tert-amyl | 2,4-xylyl | para-tolyl | |
| tert-amyl | tert-amyl | 2,5-xylyl | para-tolyl | |
| tert-amyl | tert-amyl | 2,6-xylyl | para-tolyl | |
| tert-amyl | tert-amyl | 3,4-xylyl | para-tolyl | |
| tert-amyl | tert-amyl | 3,5-xylyl | para-tolyl | |
| tert-amyl | tert-amyl | mesityl | para-tolyl | |
| tert-amyl | tert-amyl | 2-tert-butylphenyl | para-tolyl | |
| tert-amyl | tert-amyl | 3-tert-butylphenyl | para-tolyl | |
| tert-amyl | tert-amyl | 4-tert-butylphenyl | para-tolyl | |
| tert-amyl | tert-amyl | 2-ethenylphenyl | para-tolyl | |
| tert-amyl | tert-amyl | 3-ethenylphenyl | para-tolyl | |
| tert-amyl | tert-amyl | 4-ethenylphenyl | para-tolyl | |
| tert-amyl | tert-amyl | 2-biphenylyl | para-tolyl | |
| tert-amyl | tert-amyl | 3-biphenylyl | para-tolyl | |
| tert-amyl | tert-amyl | 4-biphenylyl | para-tolyl | |
| tert-amyl | tert-amyl | 1-naphthyl | para-tolyl | |
| tert-amyl | tert-amyl | 2-naphthyl | para-tolyl | |
| tert-amyl | tert-amyl | 1,1'-binaphthalene-2-yl | para-tolyl | |
| tert-amyl | tert-amyl | 2-methoxyphenyl | para-tolyl | |
| tert-amyl | tert-amyl | 3-methoxyphenyl | para-tolyl | |
| tert-amyl | tert-amyl | 4-methoxyphenyl | para-tolyl | |
| tert-amyl | tert-amyl | 2-tert-butoxyphenyl | para-tolyl | |
| tert-amyl | tert-amyl | 3-tert-butoxyphenyl | para-tolyl | |
| tert-amyl | tert-amyl | 4-tert-butoxyphenyl | para-tolyl | |
| tert-amyl | tert-amyl | 2-dimethylaminophenyl | para-tolyl | |
| tert-amyl | tert-amyl | 3-dimethylaminophenyl | para-tolyl | |

TABLE 32

Table 16-3

| R¹ | R² | R³ | Ar | Melting point (° C.) (Decomp. temp.) |
|---|---|---|---|---|
| tert-amyl | tert-amyl | 4-dimethylaminophenyl | para-tolyl | |
| tert-amyl | tert-amyl | 2'-dimethylamino-2-biphenylyl | para-tolyl | |
| tert-amyl | tert-amyl | 8-dimethylamino-1-naphthyl | para-tolyl | |
| tert-amyl | tert-amyl | 2'-dimethylamino-1,1'-binaphthalene-2-yl | para-tolyl | |
| tert-amyl | tert-amyl | benzyl | para-tolyl | |
| tert-amyl | tert-amyl | 1-phenylethyl | para-tolyl | |
| tert-amyl | tert-amyl | 2-phenylethyl | para-tolyl | |
| tert-amyl | tert-amyl | 2-ethenylbenzyl | para-tolyl | |
| tert-amyl | tert-amyl | 3-ethenylbenzyl | para-tolyl | |
| tert-amyl | tert-amyl | 4-ethenylbenzyl | para-tolyl | |
| tert-amyl | tert-amyl | 4-(2-ethenylphenyl)butyl | para-tolyl | |
| tert-amyl | tert-amyl | 4-(3-ethenylphenyl)butyl | para-tolyl | |
| tert-amyl | tert-amyl | 4-(4-ethenylphenyl)butyl | para-tolyl | |
| tert-amyl | tert-amyl | vinyl | para-tolyl | |
| tert-amyl | tert-amyl | methallyl | para-tolyl | |
| tert-amyl | tert-amyl | 1-octenyl | para-tolyl | |
| tert-amyl | tert-amyl | ethynyl | para-tolyl | |
| tert-amyl | tert-amyl | 1-propynyl | para-tolyl | |
| tert-amyl | tert-amyl | 1-octynyl | para-tolyl | |
| tert-amyl | tert-amyl | allyl | para-tolyl | |
| tert-amyl | tert-amyl | 2-octenyl | para-tolyl | |

TABLE 33

Table 17-1

| R¹ | R² | R³ | Ar | Melting point (° C.) (Decomp. temp.) |
|---|---|---|---|---|
| 1-adamantyl | 1-adamantyl | hydrogen | para-tolyl | |
| 1-adamantyl | 1-adamantyl | methyl | para-tolyl | |
| 1-adamantyl | 1-adamantyl | ethyl | para-tolyl | |
| 1-adamantyl | 1-adamantyl | n-propyl | para-tolyl | |
| 1-adamantyl | 1-adamantyl | n-butyl | para-tolyl | |
| 1-adamantyl | 1-adamantyl | isobutyl | para-tolyl | |
| 1-adamantyl | 1-adamantyl | n-pentyl | para-tolyl | |
| 1-adamantyl | 1-adamantyl | isopentyl | para-tolyl | |
| 1-adamantyl | 1-adamantyl | n-hexyl | para-tolyl | |
| 1-adamantyl | 1-adamantyl | 2-methyl-1-pentyl | para-tolyl | |
| 1-adamantyl | 1-adamantyl | 2,2-diethyl-1-ethyl | para-tolyl | |
| 1-adamantyl | 1-adamantyl | n-heptyl | para-tolyl | |
| 1-adamantyl | 1-adamantyl | n-octyl | para-tolyl | |
| 1-adamantyl | 1-adamantyl | isopropyl | para-tolyl | |
| 1-adamantyl | 1-adamantyl | sec-butyl | para-tolyl | |
| 1-adamantyl | 1-adamantyl | 2-pentyl | para-tolyl | |
| 1-adamantyl | 1-adamantyl | 3-pentyl | para-tolyl | |
| 1-adamantyl | 1-adamantyl | 2-hexyl | para-tolyl | |
| 1-adamantyl | 1-adamantyl | 3-hexyl | para-tolyl | |
| 1-adamantyl | 1-adamantyl | tert-butyl | para-tolyl | |
| 1-adamantyl | 1-adamantyl | tert-amyl | para-tolyl | |
| 1-adamantyl | 1-adamantyl | 1,1-dimethylbutyl | para-tolyl | |
| 1-adamantyl | 1-adamantyl | 3-methyl-3-pentyl | para-tolyl | |
| 1-adamantyl | 1-adamantyl | 1,1,2-trimethylpropyl | para-tolyl | |
| 1-adamantyl | 1-adamantyl | 1-adamantyl | para-tolyl | |
| 1-adamantyl | 1-adamantyl | 2-methyl-1-adamantyl | para-tolyl | |
| 1-adamantyl | 1-adamantyl | cyclopropyl | para-tolyl | |
| 1-adamantyl | 1-adamantyl | cyclopentyl | para-tolyl | |
| 1-adamantyl | 1-adamantyl | cyclohexyl | para-tolyl | |
| 1-adamantyl | 1-adamantyl | 1-methylcyclohexyl | para-tolyl | |
| 1-adamantyl | 1-adamantyl | 2-methylcyclohexyl | para-tolyl | |
| 1-adamantyl | 1-adamantyl | 2-adamantyl | para-tolyl | |
| 1-adamantyl | 1-adamantyl | 1-methyl-2-adamantyl | para-tolyl | |
| 1-adamantyl | 1-adamantyl | 2-methyl-2-adamantyl | para-tolyl | |
| 1-adamantyl | 1-adamantyl | phenyl | para-tolyl | |

TABLE 34

Table 17-2

| R¹ | R² | R³ | Ar | Melting point (° C.) (Decomp. temp.) |
|---|---|---|---|---|
| 1-adamantyl | 1-adamantyl | ortho-tolyl | para-tolyl | |
| 1-adamantyl | 1-adamantyl | meta-tolyl | para-tolyl | |
| 1-adamantyl | 1-adamantyl | para-tolyl | para-tolyl | |
| 1-adamantyl | 1-adamantyl | 2,3-xylyl | para-tolyl | |
| 1-adamantyl | 1-adamantyl | 2,4-xylyl | para-tolyl | |
| 1-adamantyl | 1-adamantyl | 2,5-xylyl | para-tolyl | |
| 1-adamantyl | 1-adamantyl | 2,6-xylyl | para-tolyl | |
| 1-adamantyl | 1-adamantyl | 3,4-xylyl | para-tolyl | |
| 1-adamantyl | 1-adamantyl | 3,5-xylyl | para-tolyl | |
| 1-adamantyl | 1-adamantyl | mesityl | para-tolyl | |
| 1-adamantyl | 1-adamantyl | 2-tert-butylphenyl | para-tolyl | |
| 1-adamantyl | 1-adamantyl | 3-tert-butylphenyl | para-tolyl | |
| 1-adamantyl | 1-adamantyl | 4-tert-butylphenyl | para-tolyl | |
| 1-adamantyl | 1-adamantyl | 2-ethenylphenyl | para-tolyl | |
| 1-adamantyl | 1-adamantyl | 3-ethenylphenyl | para-tolyl | |
| 1-adamantyl | 1-adamantyl | 4-ethenylphenyl | para-tolyl | |
| 1-adamantyl | 1-adamantyl | 2-biphenylyl | para-tolyl | |
| 1-adamantyl | 1-adamantyl | 3-biphenylyl | para-tolyl | |

TABLE 34-continued

Table 17-2

| R¹ | R² | R³ | Ar | Melting point (° C.) (Decomp. temp.) |
|---|---|---|---|---|
| 1-adamantyl | 1-adamantyl | 4-biphenylyl | para-tolyl | |
| 1-adamantyl | 1-adamantyl | 1-naphthyl | para-tolyl | |
| 1-adamantyl | 1-adamantyl | 2-naphthyl | para-tolyl | |
| 1-adamantyl | 1-adamantyl | 1,1'-binaphthalene-2-yl | para-tolyl | |
| 1-adamantyl | 1-adamantyl | 2-methoxyphenyl | para-tolyl | |
| 1-adamantyl | 1-adamantyl | 3-methoxyphenyl | para-tolyl | |
| 1-adamantyl | 1-adamantyl | 4-methoxyphenyl | para-tolyl | |
| 1-adamantyl | 1-adamantyl | 2-tert-butoxyphenyl | para-tolyl | |
| 1-adamantyl | 1-adamantyl | 3-tert-butoxyphenyl | para-tolyl | |
| 1-adamantyl | 1-adamantyl | 4-tert-butoxyphenyl | para-tolyl | |
| 1-adamantyl | 1-adamantyl | 2-dimethylaminophenyl | para-tolyl | |
| 1-adamantyl | 1-adamantyl | 3-dimethylaminophenyl | para-tolyl | |

TABLE 35

Table 17-3

| R¹ | R² | R³ | Ar | Melting point (° C.) (Decomp. temp.) |
|---|---|---|---|---|
| 1-adamantyl | 1-adamantyl | 4-dimethylaminophenyl | para-tolyl | |
| 1-adamantyl | 1-adamantyl | 2'-dimethylamino-2-biphenylyl | para-tolyl | |
| 1-adamantyl | 1-adamantyl | 8-dimethylamino-1-naphthyl | para-tolyl | |
| 1-adamantyl | 1-adamantyl | 2'-dimethylamino-1,1'-binaphthalene-2-yl | para-tolyl | |
| 1-adamantyl | 1-adamantyl | benzyl | para-tolyl | |
| 1-adamantyl | 1-adamantyl | 1-phenylethyl | para-tolyl | |
| 1-adamantyl | 1-adamantyl | 2-phenylethyl | para-tolyl | |
| 1-adamantyl | 1-adamantyl | 2-ethenylbenzyl | para-tolyl | |
| 1-adamantyl | 1-adamantyl | 3-ethenylbenzyl | para-tolyl | |
| 1-adamantyl | 1-adamantyl | 4-ethenylbenzyl | para-tolyl | |
| 1-adamantyl | 1-adamantyl | 4-(2-ethenylphenyl)butyl | para-tolyl | |
| 1-adamantyl | 1-adamantyl | 4-(3-ethenylphenyl)butyl | para-tolyl | |
| 1-adamantyl | 1-adamantyl | 4-(4-ethenylphenyl)butyl | para-tolyl | |
| 1-adamantyl | 1-adamantyl | vinyl | para-tolyl | |
| 1-adamantyl | 1-adamantyl | methallyl | para-tolyl | |
| 1-adamantyl | 1-adamantyl | 1-octenyl | para-tolyl | |
| 1-adamantyl | 1-adamantyl | ethynyl | para-tolyl | |
| 1-adamantyl | 1-adamantyl | 1-propynyl | para-tolyl | |
| 1-adamantyl | 1-adamantyl | 1-octynyl | para-tolyl | |
| 1-adamantyl | 1-adamantyl | allyl | para-tolyl | |
| 1-adamantyl | 1-adamantyl | 2-octenyl | para-tolyl | |

TABLE 36

Table 18-1

| R¹ | R² | R³ | Ar | Melting point (° C.) (Decomp. temp.) |
|---|---|---|---|---|
| 2-adamantyl | 2-adamantyl | hydrogen | para-tolyl | |
| 2-adamantyl | 2-adamantyl | methyl | para-tolyl | |
| 2-adamantyl | 2-adamantyl | ethyl | para-tolyl | |
| 2-adamantyl | 2-adamantyl | n-propyl | para-tolyl | |
| 2-adamantyl | 2-adamantyl | n-butyl | para-tolyl | |
| 2-adamantyl | 2-adamantyl | isobutyl | para-tolyl | |
| 2-adamantyl | 2-adamantyl | n-pentyl | para-tolyl | |
| 2-adamantyl | 2-adamantyl | isopentyl | para-tolyl | |
| 2-adamantyl | 2-adamantyl | n-hexyl | para-tolyl | |
| 2-adamantyl | 2-adamantyl | 2-methyl-1-pentyl | para-tolyl | |
| 2-adamantyl | 2-adamantyl | 2,2-diethyl-1-ethyl | para-tolyl | |
| 2-adamantyl | 2-adamantyl | n-heptyl | para-tolyl | |
| 2-adamantyl | 2-adamantyl | n-octyl | para-tolyl | |
| 2-adamantyl | 2-adamantyl | isopropyl | para-tolyl | |
| 2-adamantyl | 2-adamantyl | sec-butyl | para-tolyl | |
| 2-adamantyl | 2-adamantyl | 2-pentyl | para-tolyl | |
| 2-adamantyl | 2-adamantyl | 3-pentyl | para-tolyl | |
| 2-adamantyl | 2-adamantyl | 2-hexyl | para-tolyl | |
| 2-adamantyl | 2-adamantyl | 3-hexyl | para-tolyl | |
| 2-adamantyl | 2-adamantyl | tert-butyl | para-tolyl | |
| 2-adamantyl | 2-adamantyl | tert-amyl | para-tolyl | |
| 2-adamantyl | 2-adamantyl | 1,1-dimethylbutyl | para-tolyl | |
| 2-adamantyl | 2-adamantyl | 3-methyl-3-pentyl | para-tolyl | |
| 2-adamantyl | 2-adamantyl | 1,1,2-trimethylpropyl | para-tolyl | |
| 2-adamantyl | 2-adamantyl | 1-adamantyl | para-tolyl | |
| 2-adamantyl | 2-adamantyl | 2-methyl-1-adamantyl | para-tolyl | |
| 2-adamantyl | 2-adamantyl | cyclopropyl | para-tolyl | |
| 2-adamantyl | 2-adamantyl | cyclopentyl | para-tolyl | |
| 2-adamantyl | 2-adamantyl | cyclohexyl | para-tolyl | |
| 2-adamantyl | 2-adamantyl | 1-methylcyclohexyl | para-tolyl | |
| 2-adamantyl | 2-adamantyl | 2-methylcyclohexyl | para-tolyl | |
| 2-adamantyl | 2-adamantyl | 2-adamantyl | para-tolyl | |
| 2-adamantyl | 2-adamantyl | 1-methyl-2-adamantyl | para-tolyl | |
| 2-adamantyl | 2-adamantyl | 2-methyl-2-adamantyl | para-tolyl | |
| 2-adamantyl | 2-adamantyl | phenyl | para-tolyl | |

TABLE 37

Table 18-2

| R¹ | R² | R³ | Ar | Melting point (° C.) (Decomp. temp.) |
|---|---|---|---|---|
| 2-adamantyl | 2-adamantyl | ortho-tolyl | para-tolyl | |
| 2-adamantyl | 2-adamantyl | meta-tolyl | para-tolyl | |
| 2-adamantyl | 2-adamantyl | para-tolyl | para-tolyl | |
| 2-adamantyl | 2-adamantyl | 2,3-xylyl | para-tolyl | |
| 2-adamantyl | 2-adamantyl | 2,4-xylyl | para-tolyl | |
| 2-adamantyl | 2-adamantyl | 2,5-xylyl | para-tolyl | |
| 2-adamantyl | 2-adamantyl | 2,6-xylyl | para-tolyl | |
| 2-adamantyl | 2-adamantyl | 3,4-xylyl | para-tolyl | |
| 2-adamantyl | 2-adamantyl | 3,5-xylyl | para-tolyl | |
| 2-adamantyl | 2-adamantyl | mesityl | para-tolyl | |
| 2-adamantyl | 2-adamantyl | 2-tert-butylphenyl | para-tolyl | |
| 2-adamantyl | 2-adamantyl | 3-tert-butylphenyl | para-tolyl | |
| 2-adamantyl | 2-adamantyl | 4-tert-butylphenyl | para-tolyl | |
| 2-adamantyl | 2-adamantyl | 2-ethenylphenyl | para-tolyl | |
| 2-adamantyl | 2-adamantyl | 3-ethenylphenyl | para-tolyl | |
| 2-adamantyl | 2-adamantyl | 4-ethenylphenyl | para-tolyl | |
| 2-adamantyl | 2-adamantyl | 2-biphenylyl | para-tolyl | |
| 2-adamantyl | 2-adamantyl | 3-biphenylyl | para-tolyl | |

TABLE 37-continued

Table 18-2

| R¹ | R² | R³ | Ar | Melting point (° C.) (Decomp. temp.) |
|---|---|---|---|---|
| 2-adamantyl | 2-adamantyl | 4-biphenylyl | para-tolyl | |
| 2-adamantyl | 2-adamantyl | 1-naphthyl | para-tolyl | |
| 2-adamantyl | 2-adamantyl | 2-naphthyl | para-tolyl | |
| 2-adamantyl | 2-adamantyl | 1,1'-binaphthalene-2-yl | para-tolyl | |
| 2-adamantyl | 2-adamantyl | 2-methoxyphenyl | para-tolyl | |
| 2-adamantyl | 2-adamantyl | 3-methoxyphenyl | para-tolyl | |
| 2-adamantyl | 2-adamantyl | 4-methoxyphenyl | para-tolyl | |
| 2-adamantyl | 2-adamantyl | 2-tert-butoxyphenyl | para-tolyl | |
| 2-adamantyl | 2-adamantyl | 3-tert-butoxyphenyl | para-tolyl | |
| 2-adamantyl | 2-adamantyl | 4-tert-butoxyphenyl | para-tolyl | |
| 2-adamantyl | 2-adamantyl | 2-dimethyl-aminophenyl | para-tolyl | |
| 2-adamantyl | 2-adamantyl | 3-dimethyl-aminophenyl | para-tolyl | |

TABLE 38

Table 18-3

| R¹ | R² | R³ | Ar | Melting point (° C.) (Decomp. temp.) |
|---|---|---|---|---|
| 2-adamantyl | 2-adamantyl | 4-dimethyl-aminophenyl | para-tolyl | |
| 2-adamantyl | 2-adamantyl | 2'-dimethylamino-2-biphenylyl | para-tolyl | |
| 2-adamantyl | 2-adamantyl | 8-dimethylamino-1-naphthyl | para-tolyl | |
| 2-adamantyl | 2-adamantyl | 2'-dimethylamino-1,1'-binaphthalene-2-yl | para-tolyl | |
| 2-adamantyl | 2-adamantyl | benzyl | para-tolyl | |
| 2-adamantyl | 2-adamantyl | 1-phenylethyl | para-tolyl | |
| 2-adamantyl | 2-adamantyl | 2-phenylethyl | para-tolyl | |
| 2-adamantyl | 2-adamantyl | 2-ethenylbenzyl | para-tolyl | |
| 2-adamantyl | 2-adamantyl | 3-ethenylbenzyl | para-tolyl | |
| 2-adamantyl | 2-adamantyl | 4-ethenylbenzyl | para-tolyl | |
| 2-adamantyl | 2-adamantyl | 4-(2-ethenylphenyl)butyl | para-tolyl | |
| 2-adamantyl | 2-adamantyl | 4-(3-ethenylphenyl)butyl | para-tolyl | |
| 2-adamantyl | 2-adamantyl | 4-(4-ethenylphenyl)butyl | para-tolyl | |
| 2-adamantyl | 2-adamantyl | vinyl | para-tolyl | |
| 2-adamantyl | 2-adamantyl | methallyl | para-tolyl | |
| 2-adamantyl | 2-adamantyl | 1-octenyl | para-tolyl | |
| 2-adamantyl | 2-adamantyl | ethynyl | para-tolyl | |
| 2-adamantyl | 2-adamantyl | 1-propynyl | para-tolyl | |
| 2-adamantyl | 2-adamantyl | 1-octynyl | para-tolyl | |
| 2-adamantyl | 2-adamantyl | allyl | para-tolyl | |
| 2-adamantyl | 2-adamantyl | 2-octenyl | para-tolyl | |

EXAMPLES

The present invention will be described with reference to the following examples, but it should be construed that the invention is in no way limited to the examples. The processes for producing a phosphonium borate compound, the novel phosphonium borate compounds, and the use of the compounds will be described by Examples A relating to trialkylphosphonium tetraphenylborates and Examples B relating to novel phosphonium borate compounds.

Example A-1

Production of tri-tert-butylphosphonium tetraphenylborate

A 30-ml four-necked flask sufficiently purged with argon was equipped with a stirrer, a thermometer and a reflux condenser. 8.1 g (40 mmol) of tri-tert-butylphosphine and 8.1 ml of heptane were weighed in the flask, followed by stirring to dissolve tri-tert-butylphosphine. While the stirring was continuously carried out, 8.0 ml (40 mmol) of 5N hydrochloric acid was added to the solution, and the mixture was stirred at 25° C. for 1 hour. Thereafter, the organic phase was analyzed by gas chromatography, which confirmed the disappearance of tri-tert-butylphosphine, and the reaction was completed. After the completion of the reaction, the liquid was separated. The aqueous phase was washed with 8.1 ml of heptane. The aqueous phase was assumed to contain tri-tert-butylphosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of tri-tert-butylphosphine hydrochloride was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 18.2 g of objective tri-tert-butylphosphonium tetraphenylborate as white crystal. The yield (mol %) was 87% based on tri-tert-butylphosphine.

The crystal was analyzed by the methods indicated below and was identified to be tri-tert-butylphosphonium tetraphenylborate. The analytical values and properties were as follows.

(1) Melting point: 185-201° C. (decomposition)

(2) $^1$H-NMR spectrum (δ in DMSO-d6) 1.54 ppm (d, 27H, J=15.2 Hz, H$_3$C—C—P) 5.23-7.07 ppm (brd, 1H, H—P) 6.79 ppm (t, 4H, J=7.34 Hz, Ph-B) 6.92 ppm (t, 8H, J=7.34 Hz, Ph-B) 7.18 ppm (brs, 8H, Ph-B)

(3) $^{13}$C-NMR spectrum (δ in DMSO-d6) 29.3 ppm (s, H$_3$C—C—P) 36.3 ppm (d, J=28.6 Hz, H$_3$C—C—P) 121.4 ppm (s, Ph-B) 125.2 ppm (dd, J=3.1 Hz, 5.6 Hz, Ph-B) 135.5 ppm (d, J=1.2 Hz, Ph-B) 163.3 ppm (dd, J=49.4 Hz, 98.5 Hz, Ph quaternary-B)

(4) IR spectrum (KBr) 2395 cm$^{-1}$

Example A-2

Production of tri-tert-butylphosphonium tetraphenylborate

A 30-ml four-necked flask sufficiently purged with argon was equipped with a stirrer, a thermometer and a reflux condenser. 8.1 g (40 mmol) of tri-tert-butylphosphine and 8.1 ml of heptane were weighed in the flask, followed by stirring to dissolve tri-tert-butylphosphine. While the stirring was continuously carried out, 11.0 ml (22 mmol) of 4N sulfuric acid was added to the solution, and the mixture was stirred at 25° C. for 1 hour. Thereafter, the organic phase was analyzed by gas chromatography, which confirmed the disappearance of tri-tert-butylphosphine, and the reaction was completed. After the completion of the reaction, the liquid was separated. The aqueous phase was washed with 8.1 ml of heptane. The aqueous phase was assumed to contain tri-tert-butylphosphine sulfate dissolved therein.

A 300-ml four-necked flask was equipped with a stirrer, a thermometer and a reflux condenser. 16.4 g (48 mmol) of sodium tetraphenylborate and 66 ml of water were weighed in the flask, followed by stirring to dissolve sodium tetraphenylborate. While the stirring was continuously carried out, the aqueous solution of tri-tert-butylphosphine sulfate was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 19.4 g of objective tri-tert-butylphosphonium tetraphenylborate as white crystal. The yield (mol %) was 93% based on tri-tert-butylphosphine.

The crystal was analyzed by the methods indicated below and was identified to be tri-tert-butylphosphonium tetraphenylborate. The analytical values and properties were as follows.

(1) Melting point: 185-201° C. (decomposition)

(2) $^1$H-NMR spectrum (δ in DMSO-d6) 1.54 ppm (d, 27H, J=15.2 Hz, $\underline{H_3}$C—C—P) 5.23-7.07 ppm (brd, 1H, $\underline{H}$—P) 6.79 ppm (t, 4H, J=7.34 Hz, $\underline{Ph}$-B) 6.92 ppm (t, 8H, J=7.34 Hz, $\underline{Ph}$-B) 7.18 ppm (brs, 8H, $\underline{Ph}$-B)

(3) $^{13}$C-NMR spectrum (δ in DMSO-d6) 29.3 ppm (s, $H_3\underline{C}$—C—P) 36.3 ppm (d, J=28.6 Hz, $H_3$C—$\underline{C}$—P) 121.4 ppm (s, $\underline{Ph}$-B) 125.2 ppm (dd, J=3.1 Hz, 5.6 Hz, $\underline{Ph}$-B) 135.5 ppm (d, J=1.2 Hz, $\underline{Ph}$-B) 163.3 ppm (dd, J=49.1 Hz, 98.5 Hz, $\underline{Ph}$ quaternary-B)

(4) IR spectrum (KBr) 2395 cm$^{-1}$

Example A-3

Production of tri-n-butylphosphonium tetraphenylborate

The procedures in Example A-1 were repeated except that 8.1 g (40 mmol) of tri-tert-butylphosphine was replaced with 8.1 g (40 mmol) of tri-n-butylphosphine. Consequently, 18.8 g of objective tri-n-butylphosphonium tetraphenylborate was obtained as white crystal. The yield (mol %) was 90% based on tri-n-butylphosphine.

The crystal was analyzed by the methods indicated below and was identified to be tri-n-butylphosphonium tetraphenylborate. The analytical values and properties were as follows.

(1) Melting point: 114-116° C. (decomposition)

(2) $^1$H-NMR spectrum (δ in DMSO-d6) 0.91 ppm (t, 9H, J=7.15 Hz, $\underline{H_3}$C—(CH$_2$)$_3$—P) 1.33-1.46 ppm (m, 6H, H$_3$C—(C$\underline{H_2}$)$_3$—P) 1.48-1.60 ppm (m, 6H, H$_3$C—(C$\underline{H_2}$)$_3$—P) 2.10-2.30 ppm (m, 6H, H$_3$C—(C$\underline{H_2}$)$_3$—P) 5.34-7.18 ppm (brd, 1H, $\underline{H}$—P) 6.79 ppm (t, 4H, J=7.06 Hz, $\underline{Ph}$-B) 6.92 ppm (t, 8H, J=7.06 Hz, $\underline{Ph}$-B) 7.18 ppm (brs, 8H, $\underline{Ph}$-B)

(3) $^{13}$C-NMR spectrum (δ in DMSO-d6) 13.1 ppm (s, $H_3\underline{C}$—CH$_2$—CH$_2$—CH$_2$—P) 15.8 ppm (d, J=46.0 Hz, $H_3$C—CH$_2$—CH$_2$—$\underline{C}H_2$—P) 23.0 ppm (d, J=15.5 Hz, $H_3$C—CH$_2$—$\underline{C}H_2$—CH$_2$—P) 23.9 ppm (d, J=4.4 Hz, $H_3$C—$\underline{C}H_2$—CH$_2$—CH$_2$—P) 121.5 ppm (s, $\underline{Ph}$-B) 125.3 ppm (dd, J=2.5 Hz, 5.0 Hz, $\underline{Ph}$-B) 135.7 ppm (s, $\underline{Ph}$-B) 163.5 ppm (dd, J=49.1 Hz, 98.8 Hz, $\underline{Ph}$ quaternary-B)

(4) IR spectrum (KBr) 2361 cm$^{-1}$

Example A-4

Production of tricyclohexylphosphonium tetraphenylborate

The procedures in Example A-1 were repeated except that 8.1 g (40 mmol) of tri-tert-butylphosphine was replaced with 11.2 g (40 mmol) of tricyclohexylphosphine. Consequently, 21.4 g of objective tricyclohexylphosphonium tetraphenylborate was obtained as white crystal. The yield (mol %) was 89% based on tricyclohexylphosphine.

The crystal was analyzed by the methods indicated below and was identified to be tricyclohexylphosphonium tetraphenylborate. The analytical values and properties were as follows.

(1) Melting point: 171-177° C. (decomposition)

(2) $^1$H-NMR spectrum (δ in DMSO-d6) 1.17-1.89 ppm (m, 30H, cyclohexyl secondary) 2.43-2.56 ppm (m, 3H, cyclohexyl tertiary) 5.76 ppm (brd, 1H, J=470.6 Hz, $\underline{H}$—P) 6.79 ppm (t, 4H, J=7.34 Hz, $\underline{Ph}$-B) 6.93 ppm (t, 8H, J=7.34 Hz, $\underline{Ph}$-B) 7.19 ppm (brs, 8H, $\underline{Ph}$-B)

(3) $^{13}$C-NMR spectrum (δ in DMSO-d6) 24.6 ppm (d, J=1.2 Hz, cyclohexyl secondary) 25.6 ppm (d, J=13.1 Hz, cyclohexyl secondary) 26.9 ppm (d, J=39.8 Hz, cyclohexyl tertiary) 27.0 ppm (d, J=3.1 Hz, cyclohexyl secondary) 121.4 ppm (s, $\underline{Ph}$-B) 125.2 ppm (dd, J=3.1 Hz, 5.6 Hz, $\underline{Ph}$-B) 135.5 ppm (d, J=1.2 Hz, $\underline{Ph}$-B) 163.3 ppm (dd, J=49.1 Hz, 98.8 Hz, $\underline{Ph}$ quaternary-B)

(4) IR spectrum (KBr) 2359 cm$^{-1}$

Example A-5

Synthesis of 2-ortho-tolylpyridine from 2-chloropyridine and ortho-tolylboronic acid Synthesis in which tri-tert-butylphosphonium tetraphenylborate was handled in air A 50-ml four-necked flask was equipped with a stirrer, a thermometer and a reflux condenser. 0.568 g (5 mmol) of 2-chloropyridine, 0.748 g (5.5 mmol) of ortho-tolylboronic acid, 0.011 g (0.05 mmol) of palladium (II) acetate, 0.959 g (17 mmol) of potassium fluoride and 10 ml of tetrahydrofuran were weighed in the flask, followed by stirring. Further, 0.026 g (0.05 mmol) of tri-tert-butylphosphonium tetraphenylborate obtained in Example A-1 was weighed in air and added into the flask. The flask was purged with argon, followed by stirring at 25° C. for 24 hours. After the completion of the reaction, 10 ml of 10% aqueous sodium hydroxide solution was added, followed by separation. The organic phase was purified by column chromatography to afford 0.711 g of 2-ortho-tolylpyridine (yield: 84 mol % based on 2-chloropyridine). The identification of the product was made by mass spectroscopy.

Mass spectrum [EI mode] M/Z 169 (M$^+$)

Example A-6

Synthesis of 4-methylbiphenyl from 4-bromotoluene and phenylmagnesium chloride

Synthesis in which tri-tert-butylphosphonium tetraphenylborate was handled in air A 30-ml four-necked flask was equipped with a stirrer, a thermometer, a dropping funnel and a reflux condenser. 0.014 g (0.08 mmol) of palladium (II) chloride, 0.0194 g (0.19 mmol) of triethylamine and 5.5 ml of tetrahydrofuran were weighed in the flask, followed by stirring. Further, 0.084 g (0.16 mmol) of tri-tert-butylphosphonium tetraphenylborate obtained in Example A-1 was weighed in air and added into the flask. The flask was purged with argon, followed by stirring at 21° C. for 30 minutes. 1.368 g (8 mmol) of 4-bromotoluene was added, followed by stirring at 21° C. for 30 minutes. 4 ml (8.8 mmol) of 2.2M tetrahydrofuran solution of phenylmagnesium chloride was added dropwise at 21° C. over a period of 10 minutes, followed by stirring at 21° C. for 2 hours. After the completion of the reaction, 5 ml of saturated aqueous ammonium chloride solution was added, followed by separation. The organic phase was purified by column chromatography to afford 1.175 g of 4-methylbiphenyl (yield: 87 mol % based on 4-bromotoluene). The identification of the product was made by mass spectroscopy.

Mass spectrum [EI mode] M/Z 168 ($M^+$)

Example A-7

Synthesis of 4-vinylbiphenyl from bromobenzene and 4-vinylphenylmagnesium chloride Synthesis in which tri-tert-butylphosphonium tetraphenylborate was handled in air A 100-ml four-necked flask was equipped with a stirrer, a thermometer, a dropping funnel and a reflux condenser. 0.0674 g (0.3 mmol) of palladium (II) acetate and 6 ml of tetrahydrofuran were weighed in the flask, followed by stirring. Further, 0.314 g (0.6 mmol) of tri-tert-butylphosphonium tetraphenylborate obtained in Example A-1 was weighed in air and added into the flask. The flask was purged with argon, followed by stirring at 19° C. for 30 minutes. 4.710 g (30 mmol) of bromobenzene was added, followed by stirring at 19° C. for 30 minutes. 40 ml (50 mmol) of 1.25M tetrahydrofuran solution of 4-vinylphenylmagnesium chloride was added dropwise at 19° C. over a period of 2 hours, followed by stirring at 30° C. for 2 hours. After the completion of the reaction, 10 ml of saturated aqueous ammonium chloride solution was added, followed by separation. The organic phase was purified by column chromatography to afford 4.450 g of 4-vinylbiphenyl (yield: 82 mol % based on bromobenzene). The identification of the product was made by mass spectroscopy.

Mass spectrum [EI mode] M/Z 180 ($M^+$)

Example A-8

Synthesis of 1-phenylheptane from n-heptyl chloride and phenylmagnesium chloride Synthesis in which tricyclohexylphosphonium tetraphenylborate was handled in air A 30-ml four-necked flask was equipped with a stirrer, a thermometer, a dropping funnel and a reflux condenser. 0.027 g (0.12 mmol) of palladium (II) acetate and 7 ml of N-methylpyrrolidinone were weighed in the flask, followed by stirring. Further, 0.072 g (0.12 mmol) of tricyclohexylphosphonium tetraphenylborate obtained in Example A-4 was weighed in air and added into the flask. The flask was purged with argon, followed by stirring at 25° C. for 30 minutes. 0.404 g (3 mmol) of n-heptyl chloride was added, followed by stirring at 25° C. for 30 minutes. 2 ml (4.4 mmol) of 2.2M tetrahydrofuran solution of phenylmagnesium chloride was added dropwise at 25° C. over a period of 10 minutes, followed by stirring at 25° C. for 19 hours. After the completion of the reaction, 6 ml of tetrahydrofuran and 10 ml of saturated aqueous ammonium chloride solution were added, followed by separation. The organic phase was purified by column chromatography to afford 0.435 g of 1-phenylheptane (yield: 82 mol % based on n-heptyl chloride). The identification of the product was made by mass spectroscopy.

Mass spectrum [EI mode] M/Z 176 ($M^+$)

Example A-9

Synthesis of 4-cyanobiphenyl from 4-chlorobenzonitrile and phenylzinc chloride

Synthesis in which tri-tert-butylphosphonium tetraphenylborate was handled in air A 30-ml four-necked flask was equipped with a stirrer, a thermometer and a reflux condenser. 0.022 g (0.1 mmol) of palladium (II) acetate and 7 ml of N-methylpyrrolidinone were weighed in the flask, followed by stirring. Further, 0.105 g (0.2 mmol) of tri-tert-butylphosphonium tetraphenylborate obtained in Example A-1 was weighed in air and added into the flask. The flask was purged with argon, followed by stirring at 25° C. for 30 minutes to prepare a reaction liquid.

A 50-ml four-necked flask was equipped with a stirrer, a thermometer, a dropping funnel and a reflux condenser. 1.090 g (8 mmol) of zinc chloride and 4 ml of N-methylpyrrolidinone were weighed in the flask. The flask was purged with argon, followed by stirring. 3.4 ml (7.5 mmol) of 2.2M tetrahydrofuran solution of phenylmagnesium chloride was added dropwise at 25° C. over a period of 30 minutes, followed by stirring at 25° C. for 30 minutes. The reaction liquid previously obtained was added, followed by stirring at 25° C. for 30 minutes. Further, 0.688 g (5 mmol) of 4-chlorobenzonitrile was added, followed by stirring at 120° C. for 9 hours. After the completion of the reaction, 10 ml of toluene and 10 ml of saturated aqueous ammonium chloride solution were added, followed by separation. The organic phase was purified by column chromatography to afford 0.670 g of 4-cyanobiphenyl (yield: 75 mol % based on 4-chlorobenzonitrile). The identification of the product was made by mass spectroscopy.

Mass spectrum [EI mode] M/Z 179 ($M^+$)

Example A-10

Synthesis of 1-phenylheptane from chlorobenzene and n-heptylzinc chloride

Synthesis in which tri-tert-butylphosphonium tetraphenylborate was handled in air A 30-ml four-necked flask was equipped with a stirrer, a thermometer and a reflux condenser. 0.022 g (0.1 mmol) of palladium (II) acetate and 7 ml of N-methylpyrrolidinone were weighed in the flask, followed by stirring. Further, 0.105 g (0.2 mmol) of tri-tert-butylphosphonium tetraphenylborate obtained in Example A-1 was weighed in air and added into the flask. The flask was purged with argon, followed by stirring at 25° C. for 30 minutes to prepare a reaction liquid.

A 50-ml four-necked flask was equipped with a stirrer, a thermometer, a dropping funnel and a reflux condenser. 1.090 g (8 mmol) of zinc chloride and 4 ml of N-methylpyrrolidinone were weighed in the flask. The flask was purged with argon, followed by stirring. 3.5 ml (7 mmol) of 2M tetrahydrofuran solution of n-heptylmagnesium chloride was added dropwise at 25° C. over a period of 30 minutes, followed by stirring at 25° C. for 30 minutes. The reaction liquid previously obtained was added, followed by stirring at 25° C. for 30 minutes. Further, 0.558 g (5 mmol) of chlorobenzene was added, followed by stirring at 120° C. for 16 hours. After the completion of the reaction, 10 ml of toluene and 10 ml of saturated aqueous ammonium chloride solution were added, followed by separation. The organic phase was purified by column chromatography to afford 0.684 g of 1-phenylheptane (yield: 78 mol % based on chlorobenzene). The identification of the product was made by mass spectroscopy.

Mass spectrum [EI mode] M/Z 176 ($M^+$)

Example A-11

Synthesis of 2-methylbiphenyl from 2-chlorotoluene and tri-n-butylphenyltin

Synthesis in which tri-tert-butylphosphonium tetraphenylborate was handled in air A 50-ml four-necked flask was equipped with a stirrer, a thermometer and a reflux condenser. 0.045 g (0.2 mmol) of palladium (II) acetate, 1.337 g (8.8 mmol) of cesium fluoride and 4 ml of 1,4-dioxane were weighed in the flask, followed by stirring. Further, 0.418 g (0.8 mmol) of tri-tert-butylphosphonium tetraphenylborate obtained in Example A-1 was weighed in air and added into the flask. The flask was purged with argon, followed by stirring at 25° C. for 30 minutes. 0.506 g (4 mmol) of 2-chlorotoluene and 1.391 g (4.2 mmol) of tri-n-butylphenyltin were added, followed by stirring at 95° C. for 18 hours. After the completion of the reaction, 10 ml of toluene and 10 ml of saturated sodium chloride solution were added, followed by separation. The organic phase was purified by column chromatography to afford 0.508 g of 2-methylbiphenyl (yield: 76 mol % based on 2-chlorotoluene). The identification of the product was made by mass spectroscopy.

Mass spectrum [EI mode] M/Z 168 ($M^+$)

Example A-12

Synthesis of 2-methylbiphenyl from 2-bromotoluene and tri-n-butylphenyltin

Synthesis in which tri-tert-butylphosphonium tetraphenylborate was handled in air A 50-ml four-necked flask was equipped with a stirrer, a thermometer and a reflux condenser. 0.045 g (0.2 mmol) of palladium (II) acetate, 1.337 g (8.8 mmol) of cesium fluoride and 4 ml of N-methylpyrrolidinone were weighed in the flask, followed by stirring. Further, 0.418 g (0.8 mmol) of tri-tert-butylphosphonium tetraphenylborate obtained in Example A-1 was weighed in air and added into the flask. The flask was purged with argon, followed by stirring at 25° C. for 30 minutes. 0.684 g (4 mmol) of 2-bromotoluene and 1.391 g (4.2 mmol) of tri-n-butylphenyltin were added, followed by stirring at 40° C. for 17 hours. After the completion of the reaction, 10 ml of toluene and 10 ml of saturated sodium chloride solution were added, followed by separation. The organic phase was purified by column chromatography to afford 0.495 g of 2-methylbiphenyl (yield: 74 mol % based on 2-bromotoluene). The identification of the product was made by mass spectroscopy.

Mass spectrum [EI mode] M/Z 168 ($M^+$)

Example A-13

Synthesis of (E)-3-(4-dimethylaminophenyl)-2-methylacrylic acid methyl ester from 4-dimethylaminobromobenzene and methyl methacrylate Synthesis in which tri-tert-butylphosphonium tetraphenylborate was handled in air A 30-ml four-necked flask was equipped with a stirrer, a thermometer and a reflux condenser. 1.000 g (5 mmol) of 4-dimethylaminobromobenzene, 1.001 g (10 mmol) of methyl methacrylate, 0.011 g (0.012 mmol) of tris (dibenzylideneacetone)dipalladium (0), 1.074 g (5.5 mmol) of dicyclohexylmethylamine and 5 ml of tetrahydrofuran were weighed in the flask, followed by stirring. Further, 0.026 g (0.05 mmol) of tri-tert-butylphosphonium tetraphenylborate obtained in Example A-1 was weighed in air and added into the flask. The flask was purged with argon, followed by stirring at 30° C. for 25 hours. After the completion of the reaction, 5 ml of toluene and 10 ml of saturated sodium chloride solution were added, followed by separation. The organic phase was purified by column chromatography to afford 0.951 g of (E)-3-(4-dimethylaminophenyl)-2-methylacrylic acid methyl ester (yield: 87 mol % based on 4-dimethylaminobromobenzene). The identification of the product was made by $^1$H-NMR and $^{13}$C-NMR.

(1) $^1$H-NMR spectrum (δ in $CDCl_3$) 2.15 ppm (s, 3H, $H_3C$—C) 2.98 ppm (s, 6H, $H_3CN$) 3.78 ppm (s, 3H, $H_3CO$) 6.69 ppm (d, J=8.8 Hz, 2H, ring proton) 7.37 ppm (d, J=8.8 Hz, 2H, ring proton) 7.62 ppm (s, 1H, $\underline{H}C=$)

(2) $^{13}$C-NMR spectrum (δ in $CDCl_3$) 14.2, 40.1, 51.8, 111.6, 123.1, 123.7, 131.6, 139.4, 150.3, 169.8 ppm

Example A-14

Synthesis of (trans)-4-acetylstilbene from 4'-chloroacetophenone and styrene

Synthesis in which tri-tert-butylphosphonium tetraphenylborate was handled in air A 30-ml four-necked flask was equipped with a stirrer, a thermometer and a reflux condenser. 0.773 g (5 mmol) of 4'-chloroacetophenone, 1.042 g (10 mmol) of styrene, 0.034 g (0.038 mmol) of tris(dibenzylideneacetone)dipalladium (0), 1.074 g (5.5 mmol) of dicyclohexylmethylamine and 5 ml of tetrahydrofuran were weighed in the flask, followed by stirring. Further, 0.078 g (0.15 mmol) of tri-tert-butylphosphonium tetraphenylborate obtained in Example A-1 was weighed in air and added into the flask. The flask was purged with argon, followed by stirring at 30° C. for 37 hours. After the completion of the reaction, 5 ml of toluene and 10 ml of saturated sodium chloride solution were added, followed by separation. The organic phase was purified by column chromatography to afford 0.834 g of (trans)-4-acetylstilbene (yield: 75 mol % based on 4'-chloroacetophenone). The identification of the product was made by mass spectroscopy, $^1$H-NMR and $^{13}$C-NMR.

(1) Mass spectrum [EI mode] M/Z 222 (M$^+$)

(2) $^1$H-NMR spectrum (δ in CDCl$_3$) 2.60 ppm (s, 3H, H$_3$C) 7.11 ppm (d, J=16.5 Hz, 1H, HC=) 7.22 ppm (d, J=16.5 Hz, 1H, HC=) 7.24-40 ppm (m, 3H, ring proton) 7.53 ppm (d, J=7.2 Hz, 2H, ring proton) 7.57 ppm (d, J=8.7 Hz, 2H, ring proton) 7.94 ppm (d, J=8.7 Hz, 2H, ring proton)

(3) $^{13}$C-NMR spectrum (δ in CDCl$_3$) 26.9, 126.6, 126.9, 127.5, 128.4, 128.9, 129.0, 131.5, 136.0, 136.8, 142.1, 197.5 ppm Example A-15

Synthesis of (E)-3-(2,6-dimethylphenyl)-2-methylacrylic acid methyl ester from 2-chloro-meta-xylene and methyl methacrylate Synthesis in which tri-tert-butylphosphonium tetraphenylborate was handled in air A 30-ml four-necked flask was equipped with a stirrer, a thermometer and a reflux condenser. 0.703 g (5 mmol) of 2-chloro-meta-xylene, 1.001 g (10 mmol) of methyl methacrylate, 0.034 g (0.038 mmol) of tris(dibenzylideneacetone)dipalladium (0), 1.074 g (5.5 mmol) of dicyclohexylmethylamine and 5 ml of 1,4-dioxane were weighed in the flask, followed by stirring. Further, 0.078 g (0.15 mmol) of tri-tert-butylphosphonium tetraphenylborate obtained in Example A-1 was weighed in air and added into the flask. The flask was purged with argon, followed by stirring at 120° C. for 37 hours. After the completion of the reaction, 5 ml of toluene and 10 ml of saturated sodium chloride solution were added, followed by separation. The organic phase was purified by column chromatography to afford 0.774 g of (E)-3-(2,6-dimethylphenyl)-2-methylacrylic acid methyl ester (yield: 76 mol % based on 2-chloro-meta-xylene). The identification of the product was made by $^1$H-NMR and $^{13}$C-NMR.

(1) $^1$H-NMR spectrum (δ in CDCl$_3$) 1.71 ppm (d, J=1.1 Hz, 3H, H$_3$C—C=) 2.18 ppm (s, 6H, H$_3$C) 3.84 ppm (s, 3H, H$_3$CO) 7.00-7.15 ppm (m, 3H, ring proton) 7.66 ppm (s, 1H, HC=)

(2) $^{13}$C-NMR spectrum (δ in CDCl$_3$) 13.6, 19.9, 51.8, 127.2, 127.3, 130.3, 135.0, 135.2, 139.0, 168.2 ppm Example A-16

Synthesis of diphenylacetylene from bromobenzene and phenylacetylene

Synthesis in which tri-tert-butylphosphonium tetraphenylborate was handled in air A 50-ml four-necked flask was equipped with a stirrer, a thermometer and a reflux condenser. 0.034 g (0.15 mmol) of palladium (II) acetate, 0.019 g (0.1 mmol) of copper (I) iodide, 1.088 g (6 mmol) of dicyclohexylamine and 5 ml of tetrahydrofuran were weighed in the flask, followed by stirring. Further, 0.157 g (0.3 mmol) of tri-tert-butylphosphonium tetraphenylborate obtained in Example A-1 was weighed in air and added into the flask. The flask was purged with argon, followed by stirring at 30° C. for 30 minutes. 0.785 g (5 mmol) of bromobenzene and 1.021 g (10 mmol) of phenylacetylene were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.880 g of diphenylacetylene (yield: 99 mol % based on bromobenzene). The identification of the product was made by mass spectroscopy.

Mass spectrum [EI mode] M/Z 178 (M$^+$)

Example A-17

Synthesis of diphenylacetylene from bromobenzene and phenylacetylene

Synthesis in which tri-tert-butylphosphonium tetraphenylborate was handled in air A 50-ml four-necked flask was equipped with a stirrer, a thermometer and a reflux condenser. 0.034 g (0.15 mmol) of palladium (II) acetate, 1.088 g (6 mmol) of dicyclohexylamine and 5 ml of tetrahydrofuran were weighed in the flask, followed by stirring. Further, 0.157 g (0.3 mmol) of tri-tert-butylphosphonium tetraphenylborate obtained in Example A-1 was weighed in air and added into the flask. The flask was purged with argon, followed by stirring at 30° C. for 30 minutes. 0.785 g (5 mmol) of bromobenzene and 0.613 g (6 mmol) of phenylacetylene were added, followed by stirring at 30° C. for 14 hours. After the completion of the reaction, 10 ml of tetrahydrofuran, 5 ml of toluene and 15 ml of saturated sodium chloride solution were added, followed by separation. The organic phase was purified by column chromatography to afford 0.840 g of diphenylacetylene (yield: 94 mol % based on bromobenzene). The identification of the product was made by mass spectroscopy.

Mass spectrum [EI mode] M/Z 178 (M$^+$)

Example A-18

Synthesis of 4-[(trimethylsilyl)ethynyl]benzaldehyde from 4-bromobenzaldehyde and trimethylsilylacetylene Synthesis in which tri-tert-butylphosphonium tetraphenylborate was handled in air A 50-ml four-necked flask was equipped with a stirrer, a thermometer and a reflux condenser. 0.034 g (0.15 mmol) of palladium (II) acetate, 0.019 g (0.1 mmol) of copper (I) iodide, 1.088 g (6 mmol) of dicyclohexylamine and 9 ml of tetrahydrofuran were weighed in the flask, followed by stirring. Further, 0.157 g (0.3 mmol) of tri-tert-butylphosphonium tetraphenylborate obtained in Example A-1 was weighed in air and added into the flask. The flask was purged with argon, followed by stirring at 30° C. for 30 minutes. 0.925 g (5 mmol) of 4-bromobenzaldehyde and 0.589 g (6 mmol) of trimethylsilylacetylene were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.893 g of 4-[(trimethylsilyl)ethynyl]benzaldehyde (yield: 88 mol % based on 4-bromobenzaldehyde). The identification of the product was made by $^1$H-NMR and $^{13}$C-NMR.

(1) $^1$H-NMR spectrum (δ in CDCl$_3$) 0.26 ppm (s, 9H, H$_3$C) 7.59 ppm (d, J=8.1 Hz, 2H, ring proton) 7.81 ppm (d, J=8.1 Hz, 2H, ring proton) 9.99 ppm (s, 1H, HC)

(2) $^{13}$C-NMR spectrum (δ in CDCl$_3$) −0.2, 99.0, 103.8, 129.3, 129.4, 132.5, 135.6, 191.4 ppm

Example A-19

Synthesis of 4-(N,N-dimethylaminophenyl)-2-methyl-3-butyne-2-ol from 4-bromo-N,N-dimethylaniline and 2-methyl-3-butyne-2-ol Synthesis in which tri-tert-butylphosphonium tetraphenylborate was handled in air A 50-ml four-necked flask was equipped with a stirrer, a thermometer and a reflux condenser. 0.034 g (0.15 mmol) of palladium (II) acetate, 0.019 g (0.1 mmol) of copper (I) iodide, 1.088 g (6 mmol) of dicyclohexylamine and 5 ml of tetrahydrofuran were weighed in the flask, followed by stirring. Further, 0.157 g (0.3 mmol) of tri-tert-butylphosphonium tetraphenylborate obtained in Example A-1 was weighed in air and added into the flask. The flask was purged with argon, followed by stirring at 30° C. for 30 minutes. 1.000 g (5 mmol) of 4-bromo-N,N-dimethylaniline and 0.505 g (6 mmol) of 2-methyl-3-butyne-2-ol were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.876 g of 4-(N,N-dimethylaminophenyl)-2-methyl-3-butyne-2-ol (yield: 86 mol % based on 4-bromo-N,N-dimethylaniline). The identification of the product was made by mass spectroscopy, $^1$H-NMR and $^{13}$C-NMR.

(1) Mass spectrum [EI mode] M/Z 203 (M$^+$)

(2) $^1$H-NMR spectrum ($\delta$ in CDCl$_3$) 1.58 ppm (s, 6H, H$_3$CC) 2.86 ppm (s, 6H, H$_3$CN) 3.38 ppm (s, 1H, HO) 6.54 ppm (d, J=9.0 Hz, 2H, ring proton) 7.76 ppm (d, J=9.0 Hz, 2H, ring proton)

(3) $^{13}$C-NMR spectrum ($\delta$ in CDCl$_3$) 31.4, 39.8, 65.0, 82.4, 91.6, 109.6, 111.6, 132.3, 149.7 ppm

Example A-20

Synthesis of (4-fluorophenyl)-2-methyl-3-butyne-2-ol from 1-bromo-4-fluorobenzene and 2-methyl-3-butyne-2-ol Synthesis in which tri-tert-butylphosphonium tetraphenylborate was handled in air A 50-ml four-necked flask was equipped with a stirrer, a thermometer and a reflux condenser. 0.034 g (0.15 mmol) of palladium (II) acetate, 1.088 g (6 mmol) of dicyclohexylamine and 5 ml of tetrahydrofuran were weighed in the flask, followed by stirring. Further, 0.157 g (0.3 mmol) of tri-tert-butylphosphonium tetraphenylborate obtained in Example A-1 was weighed in air and added into the flask. The flask was purged with argon, followed by stirring at 30° C. for 30 minutes. 0.875 g (5 mmol) of 1-bromo-4-fluorobenzene and 0.505 g (6 mmol) of 2-methyl-3-butyne-2-ol were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.864 g of (4-fluorophenyl)-2-methyl-3-butyne-2-ol (yield: 97 mol % based on 1-bromo-4-fluorobenzene). The identification of the product was made by $^1$H-NMR and $^{13}$C-NMR.

(1) $^1$H-NMR spectrum ($\delta$ in CDCl$_3$) 1.59 ppm (s, 6H, H$_3$C) 3.41 ppm (s, 1H, HO) 6.88-6.95 ppm (m, 2H, ring proton) 7.30-7.36 ppm (m, 2H, ring proton)

(2) $^{13}$C-NMR spectrum ($\delta$ in CDCl$_3$) 31.5, 65.3, 80.8, 93.6, 115.3 (d, J=21.8 Hz), 122.1 (d, J=492.3 Hz), 133.3 (d, J=8.7 Hz), 162.2 (d, J=249.2 Hz) ppm

Example A-21

Synthesis of 1,2-diphenyl-1-propanone from chlorobenzene and propiophenone

Synthesis in which tri-tert-butylphosphonium tetraphenylborate was handled in air A 30-ml four-necked flask was equipped with a stirrer, a thermometer and a reflux condenser. 0.022 g (0.1 mmol) of palladium (II) acetate, 0.721 g (7.5 mmol) of sodium-tert-butoxide and 5 ml of tetrahydrofuran were weighed in the flask, followed by stirring. Further, 0.052 g (0.1 mmol) of tri-tert-butylphosphonium tetraphenylborate obtained in Example A-1 was weighed in air and added into the flask. The flask was purged with argon, followed by stirring at 22° C. for 30 minutes. 0.563 g (5 mmol) of chlorobenzene was added, followed by stirring at 22° C. for 30 minutes. 0.738 g (5.5 mmol) of propiophenone was added, followed by stirring at 70° C. for 6 hours. After the completion of the reaction, 2.5 ml of water was added, followed by separation. The organic phase was purified by column chromatography to afford 0.814 g of 1,2-diphenyl-1-propanone (yield: 77 mol % based on chlorobenzene). The identification of the product was made by mass spectroscopy, $^1$H-NMR and $^{13}$C-NMR.

(1) Mass spectrum [EI mode] M/Z 210 (M$^+$)

(2) $^1$H-NMR spectrum ($\delta$ in CDCl$_3$) 1.54 ppm (d, J=6.8 Hz, 3H, H$_3$C) 4.70 ppm (q, J=6.8 Hz, 1H, HC) 7.17-7.23 ppm (m, 1H, Ph) 7.29-7.30 ppm (m, 4H, Ph) 7.37-7.40 ppm (m, 2H, Ph) 7.48 ppm (t, J=7.3 Hz, 1H, Ph) 7.95 ppm (d, J=7.3 Hz, 2H, Ph)

(3) $^{13}$C-NMR spectrum ($\delta$ in CDCl$_3$) 19.6, 47.9, 127.0, 127.8, 128.5, 128.8, 129.0, 132.3, 136.5, 141.6, 200.3 ppm

Example A-22

Synthesis of 1,2-diphenyl-1-propanone from bromobenzene and propiophenone

Synthesis in which tri-tert-butylphosphonium tetraphenylborate was handled in air A 30-ml four-necked flask was equipped with a stirrer, a thermometer and a reflux condenser. 0.011 g (0.05 mmol) of palladium (II) acetate, 1.442 g (15 mmol) of sodium-tert-butoxide and 10 ml of tetrahydrofuran were weighed in the flask, followed by stirring. Further, 0.026 g (0.05 mmol) of tri-tert-butylphosphonium tetraphenylborate obtained in Example A-1 was weighed in air and added into the flask. The flask was purged with argon, followed by stirring at 25° C. for 30 minutes. 1.570 g (10 mmol) of bromobenzene was added, followed by stirring at 25° C. for 30 minutes. 1.476 g (11 mmol) of propiophenone was added, followed by stirring at 25° C. for 17 hours. After the completion of the reaction, 5 ml of water was added, followed by separation. The organic phase was purified by column chromatography to afford 2.065 g of 1,2-diphenyl-1-propanone (yield: 98 mol % based on bromobenzene). The identification of the product was made by mass spectroscopy, $^1$H-NMR and $^{13}$C-NMR.

(1) Mass spectrum [EI mode] M/Z 210 (M$^+$)

(2) $^1$H-NMR spectrum ($\delta$ in CDCl$_3$) 1.54 ppm (d, J=6.8 Hz, 3H, H$_3$C) 4.70 ppm (q, J=6.8 Hz, 1H, HC) 7.17-7.23 ppm (m, 1H, Ph) 7.29-7.30 ppm (m, 4H, Ph) 7.37-7.40 ppm (m, 2H, Ph) 7.48 ppm (t, J=7.3 Hz, 1H, Ph) 7.95 ppm (d, J=7.3 Hz, 2H, Ph)

(3) $^{13}$C-NMR spectrum ($\delta$ in CDCl$_3$) 19.6, 47.9, 127.0, 127.8, 128.5, 128.8, 129.0, 132.3, 136.5, 141.6, 200.3 ppm Example A-23

Synthesis of di-tert-butylphenyl malonate from chlorobenzene and di-tert-butyl malonate Synthesis in which tri-tert-butylphosphonium tetraphenylborate was handled in air A 30-ml four-necked flask was equipped with a stirrer, a thermometer and a reflux condenser. 0.013 g (0.06 mmol) of palladium (II) acetate, 0.317 g (3.3 mmol) of sodium-tert-butoxide and 9 ml of dioxane were weighed in the flask, followed by stirring. Further, 0.031 g (0.06 mmol) of tri-tert-butylphosphonium tetraphenylborate obtained in Example A-1 was weighed in air and added into the flask. The flask was purged with argon, followed by stirring at 25° C. for 30 minutes. 0.338 g (3 mmol) of chlorobenzene was added, followed by stirring at 25° C. for 30 minutes. 0.714 g (3.3 mmol) of di-tert-butyl malonate was added, followed by stirring at 100° C. for 12 hours. After the completion of the reaction, 9 ml of tetrahydrofuran and 9 ml of water were added, followed by separation. The organic phase was purified by column chromatography to afford 0.745 g of di-tert-butylphenyl malonate (yield: 85 mol % based on chlorobenzene). The identification of the product was made by $^1$H-NMR and $^{13}$C-NMR.

(1) $^1$H-NMR spectrum ($\delta$ in CDCl$_3$) 1.47 ppm (s, 18H, H$_3$C) 4.44 ppm (s, 1H, HC) 7.33-7.40 ppm (m, 5H, Ph)

(2) $^{13}$C-NMR spectrum ($\delta$ in CDCl$_3$) 27.9, 60.1, 81.9, 127.8, 128.4, 129.3, 133.5, 167.4 ppm Example A-24

Synthesis of ethyl-2-phenylcyanoacetate from chlorobenzene and ethyl cyanoacetate Synthesis in which tri-tert-butylphosphonium tetraphenylborate was handled in air A 30-ml four-necked flask was equipped with a stirrer, a thermometer and a reflux condenser. 0.022 g (0.1 mmol) of palladium (II) acetate, 2.459 g (15 mmol) of sodium phosphate and 15 ml of toluene were weighed in the flask, followed by stirring. Further, 0.105 g (0.2 mmol) of tri-tert-butylphosphonium tetraphenylborate obtained in Example A-1 was weighed in air and added into the flask. The flask was purged with argon, followed by stirring at 25° C. for 30 minutes. 0.563 g (5 mmol) of chlorobenzene was added, followed by stirring at 25° C. for 30 minutes. 0.622 g (5.5 mmol) of ethyl cyanoacetate was added, followed by stirring at 100° C. for 12 hours. After the completion of the reaction, 5 ml of water was added, followed by separation. The organic phase was purified by column chromatography to afford 0.501 g of ethyl-2-phenylcyanoacetate (yield: 53 mol % based on chlorobenzene). The identification of the product was made by mass spectroscopy, $^1$H-NMR and $^{13}$C-NMR.

(1) Mass spectrum [EI mode] M/Z 189 (M$^+$)

(2) $^1$H-NMR spectrum ($\delta$ in CDCl$_3$) 1.29 ppm (t, J=7.2 Hz, 3H, H$_3$C) 4.21-4.29 ppm (m, 2H, H$_2$C) 4.73 ppm (s, 1H, HC) 7.42-7.49 ppm (m, 5H, Ph)

(3) $^{13}$C-NMR spectrum ($\delta$ in CDCl$_3$) 13.9, 43.7, 63.3, 115.7, 127.9, 129.2, 129.3, 130.0, 165.0 ppm Example A-25

Synthesis of triphenylamine from chlorobenzene and diphenylamine

Synthesis in which tri-tert-butylphosphonium tetraphenylborate was handled in air A 100-ml four-necked flask was equipped with a stirrer, a thermometer and a reflux condenser. 5.403 g (48 mmol) of chlorobenzene, 6.769 g (40 mmol) of diphenylamine, 4.613 g (48 mmol) of sodium-tert-butoxide, 0.002 g (0.01 mmol) of palladium (II) acetate and 5 ml of xylene were weighed in the flask, followed by stirring. Further, 0.021 g (0.04 mmol) of tri-tert-butylphosphonium tetraphenylborate obtained in Example A-1 was weighed in air and added into the flask. The flask was purged with argon, followed by stirring at 100-120° C. for 10 hours. After the completion of the reaction, 45 ml of xylene and 50 ml of saturated sodium chloride solution were added, followed by separation. The organic phase was purified by column chromatography to afford 9.008 g of triphenylamine (yield: 92 mol % based on diphenylamine). The melting point was 125-126° C.

Example A-26

Synthesis of tert-butyl-2-methylphenyl ether from 2-chlorotoluene and sodium-tert-butoxide Synthesis in which tri-tert-butylphosphonium tetraphenylborate was handled in air A 100-ml four-necked flask was equipped with a stirrer, a thermometer and a reflux condenser. 6.330 g (50 mmol) of 2-chlorotoluene, 5.766 g (60 mmol) of sodium-tert-butoxide, 0.112 g (0.5 mmol) of palladium (II) acetate and 50 ml of xylene were weighed in the flask, followed by stirring. Further, 0.784 g (1.5 mmol) of tri-tert-butylphosphonium tetraphenylborate obtained in Example A-1 was weighed in air and added into the flask. The flask was purged with argon, followed by stirring at 125° C. for 3 hours. After the completion of the reaction, 10 ml of water was added, followed by separation. The organic phase was purified by distillation to afford 7.695 g of tert-butyl-2-methylphenyl ether (yield: 94 mol % based on 2-chlorotoluene). The boiling point was 75° C./9 Torr.

Example A-27

Synthesis of 2-methoxy-4,2'-dimethylphenyl ether from 2-chlorotoluene and 2-methoxy-4-methylphenol Synthesis in which tri-tert-butylphosphonium tetraphenylborate was handled in air A 200-ml four-necked flask was equipped with a stirrer, a thermometer and a reflux condenser. 1.920 g (48 mmol) of 60 wt % sodium hydride and 50 ml of toluene were weighed in the flask. The flask was purged with argon, followed by stirring. 6.632 g (48 mmol) of 2-methoxy-4-methylphenol was added, followed by stirring at 25° C. for 30 minutes. Further, 5.064 g (40 mmol) of 2-chlorotoluene and 0.449 g (2 mmol) of palladium (II) acetate were added, followed by stirring.

Further, 1.045 g (2 mmol) of tri-tert-butylphosphonium tetraphenylborate obtained in Example A-1 was weighed in air and added into the flask, followed by stirring at 104° C. for 9 hours. After the completion of the reaction, 50 ml of saturated sodium chloride solution was added, followed by separation. The organic phase was purified by column chromatography to afford 6.803 g of 2-methoxy-4,2'-dimethylphenyl ether (yield: 75 mol % based on 2-chlorotoluene). The identification of the product was made by mass spectroscopy, $^1$H-NMR and $^{13}$C-NMR.

(1) Mass spectrum [EI mode] M/Z 228 (M$^+$)

(2) $^1$H-NMR spectrum (δ in CDCl$_3$) 2.32 ppm (s, 3H, H$_3$C) 2.34 ppm (s, 3H, H$_3$C) 3.84 ppm (s, 3H, H$_3$CO) 6.68-6.81 ppm (m, 4H, ring proton) 6.95-7.22 ppm (m, 3H, ring proton)

(3) $^{13}$C-NMR spectrum (δ in CDCl$_3$) 16.2, 21.2, 56.0, 113.7, 117.1, 117.2, 119.3, 121.3, 122.8, 126.8, 131.1, 133.7, 143.8, 150.5, 155.8 ppm Example B-1

Production of di-tert-butylmethylphosphonium tetraphenylborate

A 30-ml four-necked flask sufficiently purged with argon was equipped with a stirrer, a thermometer and a reflux condenser. 6.4 g (40 mmol) of di-tert-butylmethylphosphine and 6.4 ml of heptane were weighed in the flask, followed by stirring to dissolve di-tert-butylmethylphosphine. While the stirring was continuously carried out, 8.0 ml (40 mmol) of 5N hydrochloric acid was added to the solution, and the mixture was stirred at 25° C. for 1 hour. Thereafter, the organic phase was analyzed by gas chromatography, which confirmed the disappearance of di-tert-butylmethylphosphine. After the completion of the reaction, the liquid was separated. The aqueous phase was washed with 6.4 ml of heptane. The aqueous phase was assumed to contain di-tert-butylmethylphosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of di-tert-butylmethylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 17.1 g of objective di-tert-butylmethylphosphonium tetraphenylborate as white crystal. The yield (mol %) was 89% based on di-tert-butylmethylphosphine.

The crystal was analyzed by the methods indicated below and was identified to be di-tert-butylmethylphosphonium tetraphenylborate. The analytical values and properties were as follows.

(1) Melting point: 192-196° C. (decomposition temperature)

(2) IR spectrum (KBr) 2359 cm$^{-1}$ (3) $^1$H-NMR spectrum (δ in DMSO-d6) 1.33 ppm (d, 18H, J=16.7 Hz, H$_3$C—C—P) 1.83 ppm (d, 3H, J=13.6 Hz, H$_3$C—P) 5.27-7.18 ppm (brd, 1H, H—P) 6.80 ppm (t, 4H, J=7.15 Hz, Ph-B) 6.93 ppm (t, 8H, J=7.34 Hz, Ph-B) 7.20 ppm (brs, 8H, Ph-B)

(4) $^{13}$C-NMR spectrum (δ in DMSO-d6) −3.2 ppm (d, J=43.5 Hz, H$_3$C—P) 26.0 ppm (s, H$_3$C—C—P) 30.8 ppm (d, J=37.9 Hz, H$_3$C—C—P) 121.4 ppm (s, Ph-B) 125.2 ppm (dd, J=2.5 Hz, 5.6 Hz, Ph-B) 135.5 ppm (d, J=1.9 Hz, Ph-B) 163.3 ppm (dd, J=49.4 Hz, 98.5 Hz, Ph quaternary-B)

Example B-2

Production of di-tert-butylmethylphosphonium tetra-para-tolylborate

A 30-ml four-necked flask sufficiently purged with argon was equipped with a stirrer, a thermometer and a reflux condenser. 6.4 g (40 mmol) of di-tert-butylmethylphosphine and 6.4 ml of heptane were weighed in the flask, followed by stirring to dissolve di-tert-butylmethylphosphine. While the stirring was continuously carried out, 11.0 ml (22 mmol) of 4N sulfuric acid was added to the solution, and the mixture was stirred at 25° C. for 1 hour. Thereafter, the organic phase was analyzed by gas chromatography, which confirmed the disappearance of di-tert-butylmethylphosphine. After the completion of the reaction, the liquid was separated. The aqueous phase was washed with 6.4 ml of heptane. The aqueous phase was assumed to contain di-tert-butylmethylphosphine sulfate dissolved therein.

A 300-ml four-necked flask was equipped with a stirrer, a thermometer and a reflux condenser. 19.1 g (48 mmol) of sodium tetra-para-tolylborate, 100 ml of tetrahydrofuran and 100 ml of toluene were weighed in the flask, followed by stirring to dissolve sodium tetra-para-tolylborate. While the stirring was continuously carried out, the aqueous solution of di-tert-butylmethylphosphine sulfate previously obtained was added to the solution, and the mixture was stirred at 25° C. for 3 hours. After the completion of the reaction, the precipitated product was filtered off and washed with 200 ml of toluene. The so obtained crystal was suspended in 200 ml of water at 50° C., and the suspension was cooled to 25° C. and filtered. The product filtered off was washed with 200 ml of water. The crystal was then suspended in 200 ml of methanol at 50° C., and the suspension was cooled to 25° C. and filtered. The product filtered off was washed with 200 ml of methanol. The crystal obtained was dried to give 17.2 g of objective di-tert-butylmethylphosphonium tetra-para-tolylborate as white crystal. The yield (mol %) was 80% based on di-tert-butylmethylphosphine.

The crystal was analyzed by the methods indicated below and was identified to be di-tert-butylmethylphosphonium tetra-para-tolylborate. The analytical values and properties were as follows.

(1) Melting point: 157-166° C. (decomposition temperature)

(2) IR spectrum (KBr) 2359 cm$^{-1}$ (3) $^1$H-NMR spectrum (δ in DMSO-d6) 1.32 ppm (d, 18H, J=16.5 Hz, H$_3$C—C—P) 1.81 ppm (d, 3H, J=13.6 Hz, H$_3$C—P) 2.15 ppm (s, 12H, H$_3$C—C$_6$H$_4$—B) 5.18-7.08 ppm (brd, 1H, H—P) 6.72 ppm (t, 8H, J=7.70 Hz, H$_3$C—C$_6$H$_4$—B) 7.05 ppm (brs, 8H, H$_3$C—C$_6$H$_4$—B)

(4) $^{13}$C-NMR spectrum (δ in DMSO-d6) 3.2 ppm (d, J=45.4 Hz, H$_3$C—P) 20.8 ppm (s, H$_3$C—C$_6$H$_4$—B) 26.1 ppm (s, H$_3$C—C—P) 30.8 ppm (d, J=37.9 Hz, H$_3$C—C—P) 126.0 ppm (dd, J=2.5 Hz, 5.6 Hz, H$_3$C—C$_6$H$_4$—B) 129.0 ppm (s, H$_3$C—C$_6$H$_4$ quaternary-B) 135.5 ppm (d, J=1.2 Hz, H$_3$C—C$_6$H$_4$—B) 160.2 ppm (dd, J=49.7 Hz, 98.8 Hz, H$_3$C—C$_6$H$_4$ quaternary-B)

Example B-3

Production of tri-tert-butylphosphonium tetra-para-tolylborate

The procedures in Example B-2 were repeated except that 6.4 g (40 mmol) of di-tert-butylmethylphosphine was replaced with 8.1 g (40 mmol) of tri-tert-butylphosphine. Consequently, 19.0 g of objective tri-tert-butylphosphonium tetra-para-tolylborate was obtained as white crystal. The yield (mol %) was 82% based on tri-tert-butylphosphine.

The crystal was analyzed by the methods indicated below and was identified to be tri-tert-butylphosphonium tetra-para-tolylborate. The analytical values and properties were as follows.

(1) Melting point: 179-201° C. (decomposition temperature)

(2) IR spectrum (KBr) 2359 cm$^{-1}$ (3) $^1$H-NMR spectrum (δ in DMSO-d6) 1.49 ppm (d, 27H, J=15.2 Hz, $\underline{H}_3$C—C—P) 2.15 ppm (s, 12H, $\underline{H}_3$C—C$_6$H$_4$—B) 5.23-7.07 ppm (brd, 1H, $\underline{H}$—P) 6.72 ppm (t, 8H, J=7.70 Hz, H$_3$C—C$_6\underline{H}_4$—B) 7.05 ppm (brs, 8H, H$_3$C—C$_6\underline{H}_4$—B)

(4) $^{13}$C-NMR spectrum (δ in DMSO-d6) 20.8 ppm (s, H$_3$$\underline{C}$—C$_6$H$_4$—B) 29.3 ppm (s, H$_3$$\underline{C}$—C—P) 36.3 ppm (d, J=28.6 Hz, H$_3$C—$\underline{C}$—P) 125.9 ppm (dd, J=2.5 Hz, 5.6 Hz, H$_3$C—$\underline{C}_6$H$_4$—B) 129.0 ppm (s, H$_3$C—$\underline{C}_6$H$_4$ quaternary-B) 135.5 ppm (s, H$_3$C—$\underline{C}_6$H$_4$—B) 160.2 ppm (dd, J=49.7 Hz, 99.4 Hz, H$_3$C—$\underline{C}_6$H$_4$ quaternary-B)

Example B-4

Production of di-tert-butylethylphosphonium tetraphenylborate

The procedures in Example B-1 were repeated except that 6.4 g (40 mmol) of di-tert-butylmethylphosphine was replaced with 7.0 g (40 mmol) of di-tert-butylethylphosphine. Consequently, 15.8 g of objective di-tert-butylethylphosphonium tetraphenylborate was obtained as white crystal. The yield (mol %) was 80% based on di-tert-butylethylphosphine.

The crystal was analyzed by the methods indicated below and was identified to be di-tert-butylethylphosphonium tetraphenylborate. The analytical values and properties were as follows.

(1) Melting point: 174-188° C. (decomposition temperature)

(2) IR spectrum (KBr) 2359 cm$^{-1}$ (3) $^1$H-NMR spectrum (δ in DMSO-d6) 1.30 ppm (dt, 3H, J=18.7, 7.70 Hz, $\underline{H}_3$C—CH$_2$—P) 1.38 ppm (d, 18H, J=16.1 Hz, $\underline{H}_3$C—C—P) 2.33-2.39 ppm (m, 2H, H$_3$C—C$\underline{H}_2$—P) 5.92 ppm (brd, 1H, J=466.6 Hz, $\underline{H}$—P) 6.79 ppm (t, 4H, J=7.15 Hz, $\underline{Ph}$-B) 6.93 ppm (t, 8H, J=7.34 Hz, $\underline{Ph}$-B) 7.19 ppm (brs, 8H, $\underline{Ph}$-B)

(4) $^{13}$C-NMR spectrum (δ in DMSO-d6) 7.0 ppm (d, J=41.0 Hz, H$_3$C—$\underline{C}$H$_2$—P) 11.0 ppm (d, J=6.2 Hz, H$_3$$\underline{C}$—CH$_2$—P) 26.3 ppm (s, H$_3$$\underline{C}$—C—P) 32.2 ppm (d, J=35.4 Hz, H$_3$C—$\underline{C}$—P) 121.5 ppm (s, $\underline{Ph}$-B) 125.2 ppm (dd, J=3.1 Hz, 5.6 Hz, $\underline{Ph}$-B) 135.5 ppm (d, J=1.2 Hz, $\underline{Ph}$-B) 163.3 ppm (dd, J=49.5 Hz, 98.5 Hz, $\underline{Ph}$ quaternary-B)

Production of n-butyl-di-tert-butylphosphonium tetraphenylborate

The procedures in Example B-1 were repeated except that 6.4 g (40 mmol) of di-tert-butylmethylphosphine was replaced with 8.1 g (40 mmol) of n-butyl-di-tert-butylphosphine. Consequently, 15.9 g of objective n-butyl-di-tert-butylphosphonium tetraphenylborate was obtained as white crystal. The yield (mol %) was 76% based on n-butyl-di-tert-butylphosphine.

The crystal was analyzed by the methods indicated below and was identified to be n-butyl-di-tert-butylphosphonium tetraphenylborate. The analytical values and properties were as follows.

(1) Melting point: 156-162° C. (decomposition temperature)

(2) IR spectrum (KBr) 2359 cm$^{-1}$ (3) $^1$H-NMR spectrum (δ in DMSO-d6) 0.93 ppm (t, 3H, J=7.34 Hz, $\underline{H}_3$C—CH$_2$—CH$_2$—CH$_2$—P) 1.40 ppm (d, 18H, J=16.1 Hz, $\underline{H}_3$C—C—P) 1.43-1.51 ppm (m, 2H, H$_3$C—C$\underline{H}_2$—CH$_2$—CH$_2$—P) 1.59-1.61 ppm (m, 2H, H$_3$C—CH$_2$—C$\underline{H}_2$—CH$_2$—P) 2.28-2.38 ppm (m, 2H, H$_3$C—CH$_2$—CH$_2$—C$\underline{H}_2$—P) 5.21-7.18 ppm (brd, 1H, $\underline{H}$—P) 6.79 ppm (t, 4H, J=7.15 Hz, $\underline{Ph}$-B) 6.92 ppm (t, 8H, J=7.34 Hz, $\underline{Ph}$-B) 7.18 ppm (brs, 8H, $\underline{Ph}$-B)

(4) $^{13}$C-NMR spectrum (δ in DMSO-d6) 12.8 ppm (d, J=40.4 Hz, H$_3$C—CH$_2$—CH$_2$—$\underline{C}$H$_2$—P) 13.2 ppm (s, H$_3$$\underline{C}$—CH$_2$—CH$_2$—CH$_2$—P) 23.0 ppm (d, J=13.1 Hz, H$_3$C—CH$_2$—$\underline{C}$H$_2$—CH$_2$—P) 26.3 ppm (s, H$_3$$\underline{C}$—C—P) 28.5 ppm (d, J=5.6 Hz, H$_3$C—$\underline{C}$H$_2$—CH$_2$—CH$_2$—P) 32.1 ppm (d, J=35.4 Hz, H$_3$C—$\underline{C}$—P) 121.4 ppm (s, $\underline{Ph}$-B) 125.2 ppm (dd, J=2.5 Hz, 5.6 Hz, $\underline{Ph}$-B) 135.5 ppm (d, J=1.2 Hz, $\underline{HPh}$-B) 163.4 ppm (dd, J=49.4 Hz, 98.5 Hz, $\underline{Ph}$ quaternary-B)

Example B-6

Production of sec-butyl-di-tert-butylphosphonium tetraphenylborate

A 100-ml four-necked flask sufficiently purged with nitrogen was equipped with a stirrer, a thermometer and a reflux condenser. 7.2 g (40 mmol) of di-tert-butylphosphinas chloride, 0.040 g (0.40 mmol) of copper (I) chloride and 7.2 ml of tetrahydrofuran were weighed in the flask. A sec-butylmagnesium chloride solution was added dropwise to the flask at an internal temperature of 10-20° C. over a period of 1 hour, wherein the solution had been previously prepared from 4.8 g (52 mmol) of sec-butyl chloride and 1.3 g (52 mmol) of metallic magnesium in 20 g of tetrahydrofuran. The mixture was stirred at 20-30° C. for 2 hours. Gas chromatography analysis confirmed the disappearance of di-tert-butylphosphinas chloride. After the completion of the reaction, 26 ml of toluene was added, and 11.8 g (6 mmol) of 5% sulfuric acid was added dropwise to dissolve the magnesium salt, followed by separation. The organic phase was washed with 11.8 ml of water.

A 100-ml four-necked flask sufficiently purged with argon was equipped with a stirrer, a thermometer and a reflux condenser. The solution of sec-butyl-di-tert-butylphosphine prepared above was weighed in the flask, to which 8.0 ml (40 mmol) of 5N hydrochloric acid was added, followed by stirring at 25° C. for 1 hour. The organic phase was analyzed by gas chromatography, which confirmed the disappearance of sec-butyl-di-tert-butylphosphine. After the completion of the reaction, the liquid was separated and the aqueous phase was washed with 8.0 ml of heptane. The aqueous phase was assumed to contain sec-butyl-di-tert-butylphosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of sec-butyl-di-tert-butylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 15.7 g of objective sec-butyl-di-tert-butylphosphonium tetraphenylborate as white crystal. The yield (mol %) was 75% based on di-tert-butylphosphinas chloride.

The crystal was analyzed by the methods indicated below and was identified to be sec-butyl-di-tert-butylphosphonium tetraphenylborate. The analytical values and properties were as follows.

(1) Melting point: 184-187° C. (decomposition temperature)

(2) IR spectrum (KBr) 2359 cm$^{-1}$ (3) $^1$H-NMR spectrum (δ in DMSO-d6) 1.03 ppm (t, 3H, J=7.34 Hz, $\underline{H}_3$C—CH$_2$—CH—P) 1.38-1.44 ppm (m, 3H, $\underline{H}_3$C—CH—P) 1.41 ppm (d, 9H, J=16.0 Hz, $\underline{H}_3$C—C—P) 1.45 ppm (d, 9H, J=15.8 Hz, $\underline{H}_3$C—C—P) 1.64-1.78 ppm (m, 1H, H$_3$C—C$\underline{H}_2$—CH—P) 1.81-1.93 ppm (m, 1H, H$_3$C—C$\underline{H}_2$—CH—P) 2.73-2.76 ppm (m, 1H, H$_3$C—CH$_2$—C$\underline{H}$—P) 5.22-7.19 ppm (brd, 1H, $\underline{H}$—P) 6.79 ppm (t, 4H, J=7.14 Hz, $\underline{Ph}$-B) 6.93 ppm (t, 8H, J=7.34 Hz, $\underline{Ph}$-B) 7.19 ppm (brs, 8H, $\underline{Ph}$-B)

(4) $^{13}$C-NMR spectrum (δ in DMSO-d6) 12.3 ppm (d, J=11.2 Hz, H$_3\underline{C}$—CH—P) 15.2 ppm (d, J=2.5 Hz, H$_3\underline{C}$—CH$_2$—CH—P) 26.5 ppm (s, H$_3$C—$\underline{C}$H$_2$—CH—P) 27.1 ppm (d, J=34.9 Hz, H$_3$C—CH$_2$—$\underline{C}$H—P) 27.4 ppm (s, H$_3\underline{C}$—C—P) 27.8 ppm (s, H$_3\underline{C}$—C—P) 33.8 ppm (d, J=32.3 Hz, H$_3$C—$\underline{C}$—P) 34.2 ppm (d, J=31.1 Hz, H$_3$C—$\underline{C}$—P) 121.5 ppm (s, $\underline{Ph}$-B) 125.2 ppm (dd, J=3.1 Hz, 5.6 Hz, $\underline{Ph}$-B) 135.5 ppm (d, J=1.2 Hz, $\underline{Ph}$-B) 163.3 ppm (dd, J=49.4 Hz, 98.5 Hz, $\underline{Ph}$ quaternary-B)

Example B-7

Production of cyclohexyl-di-tert-butylphosphonium tetraphenylborate

A 100-ml four-necked flask sufficiently purged with nitrogen was equipped with a stirrer, a thermometer and a reflux condenser. 7.2 g (40 mmol) of di-tert-butylphosphinas chloride, 0.040 g (0.40 mmol) of copper (I) chloride and 7.2 ml of tetrahydrofuran were weighed in the flask. A cyclohexyl magnesium chloride solution was added dropwise to the flask at an internal temperature of 10-20° C. over a period of 1 hour, wherein the solution had been previously prepared from 6.2 g (52 mmol) of cyclohexyl chloride and 1.3 g (52 mmol) of metallic magnesium in 19 g of tetrahydrofuran. The mixture was stirred at 20-30° C. for 2 hours. Gas chromatography analysis confirmed the disappearance of di-tert-butylphosphinas chloride. After the completion of the reaction, 26 ml of toluene was added, and 11.8 g (6 mmol) of 5% sulfuric acid was added dropwise to dissolve the magnesium salt, followed by separation. The organic phase was washed with 11.8 ml of water.

A 100-ml four-necked flask sufficiently purged with argon was equipped with a stirrer, a thermometer and a reflux condenser. The solution of cyclohexyl-di-tert-butylphosphine prepared above was weighed in the flask, to which 8.8 ml (44 mmol) of 5N hydrochloric acid was added, followed by stirring at 25° C. for 1 hour. The organic phase was analyzed by gas chromatography, which confirmed the disappearance of cyclohexyl-di-tert-butylphosphine. After the completion of the reaction, the liquid was separated and the aqueous phase was washed with 8.8 ml of heptane. The aqueous phase was assumed to contain cyclohexyl-di-tert-butylphosphine hydrochloride dissolved therein.

A 300-ml four-necked flask was equipped with a stirrer, a thermometer and a reflux condenser. 16.4 g (48 mmol) of sodium tetraphenylborate and 66 ml of water were weighed in the flask, followed by stirring to dissolve sodium tetraphenylborate. While the stirring was continuously carried out, the aqueous solution of cyclohexyl-di-tert-butylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 15.8 g of objective cyclohexyl-di-tert-butylphosphonium tetraphenylborate as white crystal. The yield (mol %) was 72% based on di-tert-butylphosphinas chloride.

The crystal was analyzed by the methods indicated below and was identified to be cyclohexyl-di-tert-butylphosphonium tetraphenylborate. The analytical values and properties were as follows.

(1) Melting point: 171-178° C. (decomposition temperature)

(2) IR spectrum (KBr) 2390 cm$^{-1}$ (3) $^1$H-NMR spectrum (δ in DMSO-d6) 1.16-1.35 ppm (m, 3H, cyclohexyl secondary) 1.38 ppm (d, 18H, J=15.8 Hz, $\underline{H}_3$C—C—P) 1.62-1.75 ppm (m, 5H, cyclohexyl secondary) 1.83-2.03 ppm (m, 2H, cyclohexyl secondary) 2.60-2.72 ppm (m, 1H, cyclohexyl tertiary) 5.75 ppm (brd, 1H, J=462.3 Hz, $\underline{H}_{-P}$) 6.80 ppm (t, 4H, J=7.15 Hz, $\underline{Ph}$-B) 6.94 ppm (t, 8H, J=7.34 Hz, $\underline{Ph}$-B) 7.22 ppm (brs, 8H, $\underline{Ph}$-B)

(4) $^{13}$C-NMR spectrum (δ in DMSO-d6) 24.7 ppm (d, J=1.2 Hz, cyclohexyl secondary) 26.2 ppm (d, J=11.8 Hz, cyclohexyl secondary) 27.6 ppm (s, H$_3\underline{H}$C—C—P) 28.9 ppm (d, J=3.7 Hz, cyclohexyl secondary) 30.8 ppm (d, J=34.2 Hz, cyclohexyl tertiary) 34.0 ppm (d, J=31.7 Hz, H$_3$C—$\underline{H}$C—P) 121.5 ppm (s, $\underline{Ph}$-B) 125.3 ppm (dd, J=2.5 Hz, 5.6 Hz, $\underline{Ph}$-B) 135.6 ppm (d, J=1.2 Hz, $\underline{Ph}$-B) 163.4 ppm (dd, J=49.4 Hz, 98.5 Hz, $\underline{Ph}$ quaternary-B)

Example B-8

Production of di-tert-butyl-n-octylphosphonium tetraphenylborate

A 100-ml four-necked flask sufficiently purged with nitrogen was equipped with a stirrer, a thermometer and a reflux condenser. 7.2 g (40 mmol) of di-tert-butylphosphinas chloride, 0.040 g (0.40 mmol) of copper (I) chloride and 7.2 ml of tetrahydrofuran were weighed in the flask. A n-octylmagnesium chloride solution was added dropwise to the flask at an internal temperature of 10-20° C. over a period of 1 hour, wherein the solution had been previously prepared from 7.7 g (52 mmol) of n-octyl chloride and 1.3 g (52 mmol) of metallic magnesium in 17 g of tetrahydrofuran. The mixture was stirred at 20-30° C. for 2 hours. Gas chromatography analysis confirmed the disappearance of di-tert-butylphosphinas chloride. After the completion of the reaction, 26 ml of toluene was added, and 11.8 g (6 mmol) of 5% sulfuric acid was added dropwise to dissolve the magnesium salt, followed by separation. The organic phase was washed with 11.8 ml of water.

A 100-ml four-necked flask sufficiently purged with argon was equipped with a stirrer, a thermometer and a reflux condenser. The solution of di-tert-butyl-n-octylphosphine prepared above was weighed in the flask, to which 8.8 ml (44 mmol) of 5N hydrochloric acid was added, followed by stirring at 25° C. for 1 hour. The organic phase was analyzed by gas chromatography, which confirmed the disappearance of di-tert-butyl-n-octylphosphine. After the completion of the reaction, the liquid was separated and the aqueous phase was washed with 8.8 ml of heptane. The aqueous phase was assumed to contain di-tert-butyl-n-octylphosphine hydrochloride dissolved therein.

A 300-ml four-necked flask was equipped with a stirrer, a thermometer and a reflux condenser. 16.4 g (48 mmol) of sodium tetraphenylborate and 66 ml of water were weighed in the flask, followed by stirring to dissolve sodium tetraphenylborate. While the stirring was continuously carried out, the aqueous solution of di-tert-butyl-n-octylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 17.4 g of objective di-tert-butyl-n-octylphosphonium tetraphenylborate as white crystal. The yield (mol %) was 75% based on di-tert-butylphosphinas chloride.

The crystal was analyzed by the methods indicated below and was identified to be di-tert-butyl-n-octylphosphonium tetraphenylborate. The analytical values and properties were as follows.

(1) Melting point: 108-113° C. (decomposition temperature)

(2) IR spectrum (KBr) 2359 $cm^{-1}$ (3) $^1$H-NMR spectrum (δ in DMSO-d6) 0.86 ppm (t, 3H, J=5.87 Hz, $\underline{H}_3$C—(CH)$_5$—CH$_2$—CH$_2$—P) 1.27 ppm (brs, 10H, H$_3$C—(C$\underline{H}_2$)$_5$—CH$_2$—CH$_2$—P) 1.39 ppm (d, 18H, J=16.1 Hz, $\underline{H}_3$C—C—P) 1.60-1.71 ppm (m, 2H, H$_3$C—(CH$_2$)$_5$—C$\underline{H}_2$—CH$_2$—P) 2.25-2.35 ppm (m, 2H, H$_3$C—(CH$_2$)$_5$—CH$_2$—C$\underline{H}_2$—P) 5.20-7.19 ppm (brd, 1H, $\underline{H}$—P) 6.79 ppm (t, 4H, J=7.15 Hz, $\underline{Ph}$-B) 6.92 ppm (t, 8H, J=7.25 Hz, $\underline{Ph}$-B) 7.19 ppm (brs, 8H, $\underline{Ph}$-B)

(4) $^{13}$C-NMR spectrum (δ in DMSO-d6) 13.8 ppm (d, J=40.0 Hz, H$_3$C—(CH$_2$)$_6$—$\underline{C}$H$_2$—P) 13.9 ppm (s, H$_3$$\underline{C}$—CH$_2$—CH$_2$—CH$_2$—P) 22.0 ppm (s, H$_3$C—(P$\underline{H}_2$)$_4$—(CH$_2$)$_3$—P) 26.3 ppm (s, H$_3$$\underline{C}$—C—P) 26.5 ppm (d, J=6.2 Hz, H$_3$C—(CH$_2$)$_4$—$\underline{C}$H$_2$—(CH$_2$)$_2$—P) 28.2 ppm (s, H$_3$C—($\underline{C}$H$_2$)$_4$—(CH$_2$)$_3$—P) 28.4 ppm (s, H$_3$C—($\underline{C}$H$_2$)$_4$—(CH$_2$)$_3$—P) 29.8 ppm (d, J=11.8 Hz, H$_3$C—(CH$_2$)$_5$—$\underline{C}$H$_2$—CH$_2$—P) 31.1 ppm (s, H$_3$C—($\underline{C}$H$_2$)$_4$—(CH$_2$)$_3$—P) 32.1 ppm (d, J=35.4 Hz, H$_3$C—$\underline{C}$—P) 121.4 ppm (s, $\underline{Ph}$-B) 125.2 ppm (dd, J=2.5 Hz, 5.6 Hz, $\underline{Ph}$-B) 135.5 ppm (d, J=1.2 Hz, $\underline{Ph}$-B) 163.3 ppm (dd, J=49.0 Hz, 98.5 Hz, $\underline{Ph}$ quaternary-B)

Example B-9

Production of di-tert-butylphenylphosphonium tetraphenylborate

The procedures in Example B-1 were repeated except that 6.4 g (40 mmol) of di-tert-butylmethylphosphine was replaced with 8.9 g (40 mmol) of di-tert-butylphenylphosphine. Consequently, 17.8 g of objective di-tert-butylphenylphosphonium tetraphenylborate was obtained as white crystal. The yield (mol %) was 82% based on di-tert-butylphenylphosphine.

The crystal was analyzed by the methods indicated below and was identified to be di-tert-butylphenylphosphonium tetraphenylborate. The analytical values and properties were as follows.

(1) Melting point: 135-140° C. (decomposition temperature)

(2) IR spectrum (KBr) 2359 $cm^{-1}$ (3) $^1$H-NMR spectrum (δ in DMSO-d6) 1.40 ppm (d, 18H, J=16.7 Hz, $\underline{H}_3$C—C—P) 6.76-7.95 ppm (brd, 1H, H—P) 6.79 ppm (t, 4H, J=7.15 Hz, $\underline{Ph}$-B) 6.92 ppm (t, 8H, J=7.54 Hz, $\underline{Ph}$-B) 7.19 ppm (brs, 8H, $\underline{Ph}$-B) 7.70 ppm (t, 2H, J=7.70 Hz, $\underline{Ph}$-P) 7.83 ppm (t, 1H, J=7.89 Hz, $\underline{Ph}$-P) 7.92 ppm (t, 2H, J=7.89 Hz, $\underline{Ph}$-P)

(4) $^{13}$C-NMR spectrum (δ in DMSO-d6) 27.0 ppm (s, H$_3$$\underline{C}$—C—P) 33.3 ppm (d, J=31.7 Hz, H$_3$C—$\underline{C}$—P) 121.5 ppm (s, $\underline{Ph}$-B) 125.3 ppm (dd, J=3.1 Hz, 5.6 Hz, $\underline{Ph}$-B) 126.6 ppm (s, $\underline{Ph}$-P) 128.3 ppm (s, $\underline{Ph}$ quaternary-P) 130.0 ppm (d, J=11.2 Hz, $\underline{Ph}$-P) 133.3 ppm (s, $\underline{Ph}$-P) 135.5 ppm (d, J=1.2 Hz, $\underline{Ph}$-B) 163.4 ppm (dd, J=49.4 Hz, 98.5 Hz, $\underline{Ph}$ quaternary-B)

Example B-10

Production of 2-biphenylyl-di-tert-butylphosphonium tetraphenylborate

A 50-ml four-necked flask sufficiently purged with argon was equipped with a stirrer, a thermometer and a reflux condenser. 11.9 g (40 mmol) of 2-biphenylyl-di-tert-butylphosphine and 11.9 ml of heptane were weighed in the flask, followed by stirring to dissolve 2-biphenylyl-di-tert-butylphosphine. While the stirring was continuously carried out, 12.0 ml (60 mmol) of 5N hydrochloric acid was added, followed by stirring at 25° C. for 1 hour. The organic phase was analyzed by gas chromatography, which confirmed the disappearance of 2-biphenylyl-di-tert-butylphosphine. After the completion of the reaction, the liquid was separated and the aqueous phase was washed with 11.9 ml of heptane. The aqueous phase was assumed to contain 2-biphenylyl-di-tert-butylphosphine hydrochloride dissolved therein.

A 300-ml four-necked flask was equipped with a stirrer, a thermometer and a reflux condenser. 22.6 g (66 mmol) of sodium tetraphenylborate and 90 ml of water were weighed in the flask, followed by stirring to dissolve sodium tetraphenylborate. While the stirring was continuously carried out, the aqueous solution of 2-biphenylyl-di-tert-butylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 19.3 g of objective 2-biphenylyl-di-tert-butylphosphonium tetraphenylborate as white crystal. The yield (mol %) was 78% based on 2-biphenylyl-di-tert-butylphosphine.

The crystal was analyzed by the methods indicated below and was identified to be 2-biphenylyl-di-tert-butylphosphonium tetraphenylborate. The analytical values and properties were as follows.

(1) Melting point: 163-174° C. (decomposition temperature)

(2) IR spectrum (KBr) 2359 cm$^{-1}$ (3) $^1$H-NMR spectrum (δ in DMSO-d6) 1.26 ppm (d, 18H, J=17.1 Hz, H$_3$C—C—P) 6.77-7.96 ppm (brd, 1H, H—P) 6.80 ppm (t, 4H, J=7.06 Hz, Ph-B) 6.94 ppm (t, 8H, J=7.34 Hz, Ph-B) 7.18-7.21 ppm (m, 2H, 2-biphenyl) 7.28 ppm (brs, 8H, Ph-B) 7.45-7.47 ppm (m, 4H, 2-biphenyl) 7.62 ppm (d, 1H, J=7.52 Hz, 2-biphenyl) 7.72 ppm (d, 1H, J=7.61 Hz, 2-biphenyl) 7.93 ppm (d, 1H, J=8.63 Hz, 2-biphenyl)

(4) $^{13}$C-NMR spectrum (δ in DMSO-d6) 27.3 ppm (s, H$_3$C—C—P) 34.2 ppm (d, J=30.5 Hz, H$_3$C—C—P) 121.5 ppm (s, Ph-B) 125.3 ppm (dd, J=2.5 Hz, 5.6 Hz, Ph-B) 126.5 ppm (s, 2-biphenyl) 128.2 ppm (s, 2-biphenyl) 128.6 ppm (s, 2-biphenyl) 128.8 ppm (s, 2-biphenyl) 129.3 ppm (s, 2-biphenyl) 132.2 ppm (d, J=8.1 Hz, 2-biphenyl) 133.0 ppm (d, J=17.4 Hz, 2-biphenyl) 134.0 ppm (s, 2-biphenyl quaternary) 135.6 ppm (s, Ph-B) 138.4 ppm (s, 2-biphenyl quaternary) 148.3 ppm (s, 2-biphenyl quaternary) 163.4 ppm (dd, J=49.7 Hz, 98.8 Hz, Ph quaternary-B)

Example B-11

Production of di-tert-butyl-1-naphthylphosphonium tetraphenylborate

The procedures in Example B-10 were repeated except that 11.9 g (40 mmol) of 2-biphenylyl-di-tert-butylphosphine was replaced with 10.9 g (40 mmol) of di-tert-butyl-1-naphthylphosphine. Consequently, 19.0 g of objective di-tert-butyl-1-naphthylphosphonium tetraphenylborate was obtained as white crystal. The yield (mol %) was 80% based on di-tert-butyl-1-naphthylphosphine.

The crystal was analyzed by the methods indicated below and was identified to be di-tert-butyl-1-naphthylphosphonium tetraphenylborate. The analytical values and properties were as follows.

(1) Melting point: 165-174° C. (decomposition temperature)

(2) IR spectrum (KBr) 2359 cm$^{-1}$ (3) $^1$H-NMR spectrum (δ in DMSO-d6) 1.39 ppm (d, 18H, J=16.9 Hz, H$_3$C—C—P) 6.82-8.51 ppm (brd, 1H, H—P) 6.84 ppm (t, 4H, J=7.06 Hz, Ph-B) 6.99 ppm (t, 8H, J=7.34 Hz, Ph-B) 7.35 ppm (brs, 8H, Ph-B) 7.65-7.82 ppm (m, 3H, 1-naphthyl) 8.10 ppm (d, 1H, J=8.07 Hz, 1-naphthyl) 8.13-8.19 ppm (m, 1H, 1-naphthyl) 8.32 ppm (d, 1H, J=8.25 Hz, 1-naphthyl) 8.50 ppm (d, 1H, J=8.62 Hz, 1-naphthyl)

(4) $^{13}$C-NMR spectrum (δ in DMSO-d6) 27.3 ppm (s, H$_3$C—C—P) 34.4 ppm (d, J=29.2 Hz, H$_3$C—C—P) 121.5 ppm (s, Ph-B) 124.1 ppm (d, J=9.9 Hz, 1-naphthyl) 125.1 ppm (s, 1-naphthyl) 125.3 ppm (dd, J=2.5 Hz, 5.6 Hz, Ph-B) 126.5 ppm (s, 1-naphthyl) 127.3 ppm (s, 1-naphthyl) 128.2 ppm (s, 1-naphthyl) 128.9 ppm (s, 1-naphthyl) 129.9 ppm (s, 1-naphthyl) 133.1 ppm (s, 1-naphthyl quaternary) 133.3 ppm (d, J=7.5 Hz, 1-naphthyl quaternary) 134.4 ppm (d, J=6.7 Hz, 1-naphthyl quaternary) 135.7 ppm (s, Ph-B) 163.5 ppm (dd, J=49.4 Hz, 98.5 Hz, Ph quaternary-B)

Example B-12

Production of benzyl-di-tert-butylphosphonium tetraphenylborate

The procedures in Example B-1 were repeated except that 6.4 g (40 mmol) of di-tert-butylmethylphosphine was replaced with 9.5 g (40 mmol) of benzyl-di-tert-butylphosphine. Consequently, 18.0 g of objective benzyl-di-tert-butylphosphonium tetraphenylborate was obtained as white crystal. The yield (mol %) was 81% based on benzyl-di-tert-butylphosphine.

The crystal was analyzed by the methods indicated below and was identified to be benzyl-di-tert-butylphosphonium tetraphenylborate. The analytical values and properties were as follows.

(1) Melting point: 149-158° C. (decomposition temperature)

(2) IR spectrum (KBr) 2359 cm$^{-1}$ (3) $^1$H-NMR spectrum (δ in DMSO-d6) 1.38 ppm (d, 18H, J=15.8 Hz, H$_3$C—C—P) 3.99 ppm (brs, 2H, Ph-CH$_2$—P) 6.76-7.44 ppm (brd, 1H, H—P) 6.79 ppm (t, 4H, J=7.15 Hz, Ph-B) 6.92 ppm (t, 8H, J=7.34 Hz, Ph-B) 7.18 ppm (brs, 8H, Ph-B) 7.32-7.44 ppm (m, 5H, Ph-CH$_2$—P)

(4) $^{13}$C-NMR spectrum (δ in DMSO-d6) 20.4 ppm (d, J=40.0 Hz, Ph-CH$_2$—P) 26.7 ppm (s, H$_3$C—C—P) 32.9 ppm (d, J=32.3 Hz, H$_3$C—C—P) 121.5 ppm (s, Ph-B) 125.2 ppm (dd, J=2.5 Hz, 5.6 Hz, Ph-B) 127.6 ppm (s, Ph-CH$_2$—P) 129.1 ppm (s, Ph-CH$_2$—P) 129.7 ppm (d, J=6.2 Hz, Ph-CH$_2$—P) 133.0 ppm (s, Ph quaternary-CH$_2$—P) 135.5 ppm (d, J=1.2 Hz, Ph-B) 163.3 ppm (dd, J=49.4 Hz, 98.5 Hz, Ph quaternary-B)

Example B-13

Production of di-tert-butyl(4-ethenylbenzyl)phosphonium tetraphenylborate

A 100-ml four-necked flask sufficiently purged with nitrogen was equipped with a stirrer, a thermometer and a reflux condenser. 7.2 g (40 mmol) of di-tert-butylphosphinas chloride, 0.040 g (0.40 mmol) of copper (I) chloride and 7.2 ml of tetrahydrofuran were weighed in the flask. A 4-ethenylbenzylmagnesium chloride solution was added dropwise to the flask at an internal temperature of 10-20° C. over a period of 1 hour, wherein the solution had been previously prepared from 7.9 g (52 mmol) of 4-ethenylbenzyl chloride and 1.3 g (52 mmol) of metallic magnesium in 17 g of tetrahydrofuran. The mixture was stirred at 20-30° C. for 2 hours. Gas chromatography analysis confirmed the disappearance of di-tert-butylphosphinas chloride. After the completion of the reaction, 26 ml of toluene was added, and 11.8 g (6 mmol) of 5% sulfuric acid was added dropwise to dissolve the magnesium salt, followed by separation. The organic phase was washed with 11.8 ml of water.

A 100-ml four-necked flask sufficiently purged with argon was equipped with a stirrer, a thermometer and a reflux condenser. The solution of di-tert-butyl(4-ethenylbenzyl)phosphine prepared above was weighed in the flask, to which 8.0 ml (40 mmol) of 5N hydrochloric acid was added, followed by stirring at 25° C. for 1 hour. The organic phase was analyzed by gas chromatography, which confirmed the disappearance of di-tert-butyl(4-ethenylbenzyl)phosphine. After the completion of the reaction, the liquid was separated and the aqueous phase was washed with 8.0 ml of heptane. The aqueous phase was assumed to contain di-tert-butyl(4-ethenylbenzyl)phosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of di-tert-butyl(4-ethenylbenzyl)phosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 17.7 g of objective di-tert-butyl(4-ethenylbenzyl)phosphonium tetraphenylborate as white crystal. The yield (mol %) was 76% based on di-tert-butylphosphinas chloride.

The crystal was analyzed by the methods indicated below and was identified to be di-tert-butyl(4-ethenylbenzyl)phosphonium tetraphenylborate. The analytical values and properties were as follows.

(1) Melting point: 122-132° C. (decomposition temperature)

(2) IR spectrum (KBr) 2359 cm$^{-1}$ (3) $^1$H-NMR spectrum (δ in DMSO-d6) 1.40 ppm (d, 18H, J=16.1 Hz, H$_3$C—C—P) 3.96 ppm (brs, 2H, H$_2$C=CH—C$_6$H$_4$—CH$_2$—P) 5.29 ppm (d, 1H, 11.0 Hz, H$_2$C=CH—C$_6$H$_4$—CH$_2$—P) 5.86 ppm (d, 1H, 17.8 Hz, H$_2$C=CH—C$_6$H$_4$—CH$_2$—P) 6.68-7.53 ppm (brd, 1H, H—P) 6.70 ppm (d, 1H, 10.8 Hz, H$_2$C=CH—C$_6$H$_4$—CH$_2$—P) 6.78 ppm (t, 4H, J=7.15 Hz, Ph-B) 6.92 ppm (t, 8H, J=7.24 Hz, Ph-B) 7.18 ppm (brs, 8H, Ph-B) 7.42 ppm (d, 2H, J=7.70 Hz, H$_2$C=CH—C$_6$H$_4$—CH$_2$—P) 7.51 ppm (d, 2H, J=7.89 Hz, H$_2$C=CH—C$_6$H$_4$—CH$_2$—P)

(4) $^{13}$C-NMR spectrum (δ in DMSO-d6) 20.3 ppm (d, J=34.8 Hz, H$_2$C=CH—C$_6$H$_4$—CH$_2$—P) 26.7 ppm (s, H$_3$C—C—P) 32.8 ppm (d, J=31.7 Hz, H$_3$C—C—P) 114.9 ppm (s, H$_2$C=CH—C$_6$H$_4$—CH$_2$—P) 121.5 ppm (s, Ph-B) 125.2 ppm (dd, J=2.5 Hz, 5.0 Hz, Ph-B) 126.7 ppm (s, H$_2$C=CH—C$_6$H$_4$—CH$_2$—P) 128.1 ppm (d, J=6.8 Hz, H$_2$C=CH—C$_6$H$_4$ quaternary-CH$_2$—P) 128.8 ppm (s, H$_2$C=CH—C$_6$H$_4$ quaternary-CH$_2$—P) 129.9 ppm (s, H$_2$C=CH—C$_6$H$_4$—CH$_2$—P) 135.6 ppm (s, Ph-B) 135.8 ppm (s, H$_2$C=CH—C$_6$H$_4$—CH$_2$—P) 163.4 ppm (dd, J=49.4 Hz, 98.5 Hz, Ph quaternary-B)

Example B-14

Production of di-tert-butylvinylphosphonium tetraphenylborate

A 100-ml four-necked flask sufficiently purged with nitrogen was equipped with a stirrer, a thermometer and a reflux condenser. 7.2 g (40 mmol) of di-tert-butylphosphinas chloride, 0.040 g (0.40 mmol) of copper (I) chloride and 7.2 ml of tetrahydrofuran were weighed in the flask. A vinylmagnesium chloride solution was added dropwise to the flask at an internal temperature of 10-20° C. over a period of 1 hour, wherein the solution had been previously prepared from 3.3 g (52 mmol) of vinyl chloride and 1.3 g (52 mmol) of metallic magnesium in 21 g of tetrahydrofuran. The mixture was stirred at 40-50° C. for 2 hours. Gas chromatography analysis confirmed the disappearance of di-tert-butylphosphinas chloride. After the completion of the reaction, 26 ml of toluene was added, and 11.8 g (6 mmol) of 5% sulfuric acid was added dropwise to dissolve the magnesium salt, followed by separation. The organic phase was washed with 11.8 ml of water.

A 100-ml four-necked flask sufficiently purged with argon was equipped with a stirrer, a thermometer and a reflux condenser. The solution of di-tert-butylvinylphosphine prepared above was weighed in the flask, to which 8.0 ml (40 mmol) of 5N hydrochloric acid was added, followed by stirring at 25° C. for 1 hour. The organic phase was analyzed by gas chromatography, which confirmed the disappearance of di-tert-butylvinylphosphine. After the completion of the reaction, the liquid was separated and the aqueous phase was washed with 8.0 ml of heptane. The aqueous phase was assumed to contain di-tert-butylvinylphosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of di-tert-butylvinylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 14.4 g of objective di-tert-butylvinylphosphonium tetraphenylborate as white crystal. The yield (mol %) was 73% based on di-tert-butylphosphinas chloride.

The crystal was analyzed by the methods indicated below and was identified to be di-tert-butylvinylphosphonium tetraphenylborate. The analytical values and properties were as follows.

(1) Melting point: 253-261° C. (decomposition temperature)

(2) IR spectrum (KBr) 2359 cm$^{-1}$

Example B-15

Production of allyl-di-tert-butylphosphonium tetraphenylborate

A 100-ml four-necked flask sufficiently purged with nitrogen was equipped with a stirrer, a thermometer and a reflux condenser. 7.2 g (40 mmol) of di-tert-butylphosphinas chloride, 0.040 g (0.40 mmol) of copper (I) chloride and 7.2 ml of tetrahydrofuran were weighed in the flask. An allylmagnesium chloride solution was added dropwise to the flask at an internal temperature of 10-20° C. over a period of 1 hour, wherein the solution had been previously prepared from 4.0 g (52 mmol) of allyl chloride and 1.3 g (52 mmol) of metallic magnesium in 21 g of tetrahydrofuran. The mixture was stirred at 20-30° C. for 1 hour. Gas chromatography analysis confirmed the disappearance of di-tert-butylphosphinas chloride. After the completion of the reaction, 26 ml of toluene was added, and 11.8 g (6 mmol) of 5% sulfuric acid was added dropwise to dissolve the magnesium salt, followed by separation. The organic phase was washed with 11.8 ml of water.

A 200-ml four-necked flask sufficiently purged with argon was equipped with a stirrer, a thermometer and a reflux condenser. The solution of allyl-di-tert-butylphosphine prepared above was weighed in the flask, to which 8.0 ml (40 mmol) of 5N hydrochloric acid was added, followed by stirring at 25° C. for 1 hour. The organic phase was analyzed by gas chromatography, which confirmed the disappearance of allyl-di-tert-butylphosphine. After the completion of the reaction, the liquid was separated and the aqueous phase was washed with 8.0 ml of heptane. The aqueous phase was assumed to contain allyl-di-tert-butylphosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of allyl-di-tert-butylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 15.2 g of objective allyl-di-tert-butylphosphonium tetraphenylborate as white crystal. The yield (mol %) was 75% based on di-tert-butylphosphinas chloride.

The crystal was analyzed by the methods indicated below and was identified to be allyl-di-tert-butylphosphonium tetraphenylborate. The analytical values and properties were as follows.

(1) Melting point: 148-160° C. (decomposition temperature)

(2) IR spectrum (KBr) 2384 $cm^{-1}$ (3) $^1$H-NMR spectrum (δ in DMSO-d6) 1.40 ppm (d, 18H, J=16.1 Hz, $\underline{H}_3$C—C—P) 3.34 ppm (brs, 2H, $H_2$C=CH—C$\underline{H}_2$—P) 5.33 ppm (d, 1H, 9.54 Hz, $\underline{H}_2$C=CH—$CH_2$—P) 5.47 ppm (d, 1H, 16.3 Hz, $\underline{H}_2$C=CH—$CH_2$—P) 5.84-5.97 ppm (m, 1H, $H_2$C=C$\underline{H}$—$CH_2$—P) 6.77-7.36 ppm (brd, 1H, $\underline{H}$—P) 6.79 ppm (t, 4H, J=7.06 Hz, Ph-B) 6.93 ppm (t, 8H, J=7.25 Hz, Ph-B) 7.18 ppm (brs, 8H, Ph-B)

(4) $^{13}$C-NMR spectrum (δ in DMSO-d6) 18.7 ppm (d, J=36.7 Hz, $H_2$C=CH—$\underline{C}H_2$—P) 26.6 ppm (s, $H_3$C—C—P) 32.6 ppm (d, J=32.3 Hz, $H_3$C—$\underline{C}$—P) 109.5 ppm (s, $H_2\underline{C}$=CH—$CH_2$—P) 115.2 ppm (s, $H_2$C=$\underline{C}$H—$CH_2$—P) 121.5 ppm (s, Ph-B) 125.2 ppm (dd, J=2.5 Hz, 5.6 Hz, Ph-B) 135.5 ppm (s, Ph-B) 163.4 ppm (dd, J=49.7 Hz, 98.8 Hz, Ph quaternary-B)

Example B-16

Production of tricyclohexylphosphonium tetra-para-tolylborate

The procedures in Example B-2 were repeated except that 6.4 g (40 mmol) of di-tert-butylmethylphosphine was replaced with 11.2 g (40 mmol) of tricyclohexylphosphine. Consequently, 22.3 g of objective tricyclohexylphosphonium tetra-para-tolylborate was obtained as white crystal. The yield (mol %) was 85% based on tricyclohexylphosphine.

The crystal was analyzed by the methods indicated below and was identified to be tricyclohexylphosphonium tetra-para-tolylborate. The analytical values and properties were as follows.

(1) Melting point: 129-131° C.

(2) IR spectrum (KBr) 2376 $cm^{-1}$ (3) $^1$H-NMR spectrum (δ in DMSO-d6) 1.18-1.89 ppm (m, 30H, cyclohexyl secondary) 2.15 ppm (s, 12H, $\underline{H}_3$C—$C_6H_4$—B) 2.51-2.57 ppm (m, 3H, cyclohexyl tertiary) 5.77 ppm (brd, 1H, J=470.4 Hz, $\underline{H}$—P) 6.71 ppm (t, 8H, J=7.70 Hz, $H_3$C—$C_6\underline{H}_4$—B) 7.03 ppm (brs, 8H, $H_3$C—$C_6\underline{H}_4$—B)

(4) $^{13}$C-NMR spectrum (δ in DMSO-d6) 20.8 ppm (s, $H_3\underline{C}$—$C_6H_4$—B) 24.6 ppm (s, cyclohexyl secondary) 25.6 ppm (d, J=13.1 Hz, cyclohexyl secondary) 26.8 ppm (d, J=31.1 Hz, cyclohexyl tertiary) 27.0 ppm (s, cyclohexyl secondary) 125.9 ppm (dd, J=3.1 Hz, 5.6 Hz, $H_3$C—$\underline{C}_6H_4$—B) 129.0 ppm (s, $H_3$C—$\underline{C}_6H_4$ quaternary-B) 135.5 ppm (d, J=1.2 Hz, $H_3$C—$\underline{C}_6H_4$—B) 160.2 ppm (dd, J=49.4 Hz, 99.1 Hz, $H_3$C—$C_6H_4$ quaternary-B)

Example B-17

Production of triisopropylphosphonium tetraphenylborate

The procedures in Example B-1 were repeated except that 6.4 g (40 mmol) of di-tert-butylmethylphosphine was replaced with 6.4 g (40 mmol) of triisopropylphosphine. Consequently, 16.9 g of objective triisopropylphosphonium tetraphenylborate was obtained as white crystal. The yield (mol %) was 88% based on triisopropylphosphine.

The crystal was analyzed by the methods indicated below and was identified to be triisopropylphosphonium tetraphenylborate. The analytical values and properties were as follows.

(1) Melting point: 194-214° C. (decomposition temperature)

(2) IR spectrum (KBr) 2390 $cm^{-1}$ (3) $^1$H-NMR spectrum (δ in DMSO-d6) 1.31 ppm (dt, 18H, J=17.4 Hz, 7.33 Hz, $(H_3C)_2$—CH—P) 2.82 ppm (dhep, 3H, J=12.3 Hz, 7.24 Hz, $(H_3C)_2$—C$\underline{H}$—P) 5.93 ppm (brd, 1H, J=482.3 Hz, $\underline{H}$—P) 6.79 ppm (t, 4H, J=7.15 Hz, Ph-B) 6.93 ppm (t, 8H, J=7.34 Hz, Ph-B) 7.19 ppm (brs, 8H, Ph-B)

(4) $^{13}$C-NMR spectrum (δ in DMSO-d6) 17.2 ppm (d, J=2.5 Hz, $(H_3\underline{C})_2$—HC—P) 18.1 ppm (d, J=39.8 Hz, $(H_3C)_2$—H$\underline{C}$—P) 121.4 ppm (s, Ph-B) 125.2 ppm (dd, J=2.3 Hz, 5.2 Hz, Ph-B) 135.5 ppm (d, J=1.2 Hz, Ph-B) 163.3 ppm (dd, J=49.1 Hz, 98.8 Hz, Ph quaternary-B)

Example B-18

Synthesis of 1-phenylheptane from n-heptyl bromide and phenylboronic acid

Synthesis in which di-tert-butylmethylphosphonium tetraphenylborate was handled in air A 50-ml four-necked flask was equipped with a stirrer, a thermometer and a reflux condenser. 0.896 g (5 mmol) of n-heptyl bromide, 0.914 g (7.5 mmol) of phenylboronic acid, 0.056 g (0.25 mmol) of palladium (II) acetate, 1.683 g (15 mmol) of potassium tert-butoxide and 25 ml of tert-amyl alcohol were weighed in the flask, followed by stirring. Further, 0.240 g (0.5 mmol) of di-tert-butylmethylphosphonium tetraphenylborate obtained in Example B-1 was weighed in air and added into the flask. The flask was purged with argon, followed by stirring at 25° C. for 24 hours. After the completion of the reaction, 20 ml of saturated sodium chloride solution was added, followed by separation. The organic phase was purified by column chromatography to afford 0.785 g of 1-phenylheptane (yield: 89 mol % based on n-heptyl bromide). The identification of the product was made by mass spectroscopy.

Mass spectrum [EI mode] M/Z 176 ($M^+$)

Example B-19

Synthesis of 4-n-heptyltoluene from n-heptyl bromide and para-tolylboronic acid

Synthesis in which di-tert-butylmethylphosphonium tetraphenylborate was handled in air The procedures in Example B-18 were repeated except that 0.914 g (7.5 mmol) of phenylboronic acid was replaced with 1.020 g (7.5 mmol) of para-tolylboronic acid. The organic phase was purified by column chromatography to afford 0.723 g of 4-n-heptyltoluene (yield: 76 mol % based on n-heptyl bromide) The identification of the product was made by mass spectroscopy.

Mass spectrum [EI mode] M/Z 190 (M$^+$)

Example B-20

Synthesis of 1-phenylheptane from n-heptyl bromide and phenylboronic acid

Synthesis in which di-tert-butylmethylphosphonium tetra-para-tolylborate was handled in air The procedures in Example B-18 were repeated except that 0.240 g (0.5 mmol) of di-tert-butylmethylphosphonium tetraphenylborate was replaced with 0.268 g (0.5 mmol) of di-tert-butylmethylphosphonium tetra-para-tolylborate obtained in Example B-2. Consequently, 0.732 g of 1-phenylheptane was obtained (yield: 83 mol % based on n-heptyl bromide). The identification of the product was made by mass spectroscopy.

Mass spectrum [EI mode] M/Z 176 (M$^+$)

Example B-21

Similar to Example A-5

Synthesis of 2-ortho-tolylpyridine from 2-chloropyridine and ortho-tolylboronic acid Synthesis in which tri-tert-butylphosphonium tetra-para-tolylborate was handled in air A 50-ml four-necked flask was equipped with a stirrer, a thermometer and a reflux condenser. 0.568 g (5 mmol) of 2-chloropyridine, 0.748 g (5.5 mmol) of ortho-tolylboronic acid, 0.011 g (0.05 mmol) of palladium (II) acetate, 0.959 g (17 mmol) of potassium fluoride and 10 ml of tetrahydrofuran were weighed in the flask, followed by stirring. Further, 0.029 g (0.05 mmol) of tri-tert-butylphosphonium tetra-para-tolylborate obtained in Example B-3 was weighed in air and added into the flask. The flask was purged with argon, followed by stirring at 25° C. for 24 hours. After the completion of the reaction, 10 ml of 10% aqueous sodium hydroxide solution was added, followed by separation. The organic phase was purified by column chromatography to afford 0.677 g of 2-ortho-tolylpyridine (yield: 80 mol % based on 2-chloropyridine). The identification of the product was made by mass spectroscopy.

Mass spectrum [EI mode] M/Z 169 (M$^+$)

Example B-22

Synthesis of 1-phenylheptane from n-heptyl bromide and phenylmagnesium chloride

Synthesis in which di-tert-butylmethylphosphonium tetraphenylborate was handled in air A 50-ml four-necked flask was equipped with a stirrer, a thermometer, a dropping funnel and a reflux condenser. 0.045 g (0.2 mmol) of palladium (II) acetate and 2 ml of tetrahydrofuran were weighed in the flask, followed by stirring. Further, 0.096 g (0.2 mmol) of di-tert-butylmethylphosphonium tetraphenylborate obtained in Example B-1 was weighed in air and added into the flask. The flask was purged with argon, followed by stirring at 22° C. for 30 minutes. 3.582 g (20 mmol) of n-heptyl bromide was added, followed by stirring at 22° C. for 30 minutes. 10 ml (22 mmol) of 2.2M tetrahydrofuran solution of phenylmagnesium chloride was added dropwise at 30° C. over a period of 10 minutes, followed by stirring at 30° C. for 3 hours. After the completion of the reaction, 10 ml of saturated aqueous ammonium chloride solution was added, followed by separation. The organic phase was purified by column chromatography to afford 2.997 g of 1-phenylheptane (yield: 85 mol % based on n-heptyl bromide). The identification of the product was made by mass spectroscopy.

Mass spectrum [EI mode] M/Z 176 (M$^+$)

Example B-23

Similar to Example A-6

Synthesis of 4-methylbiphenyl from 4-bromotoluene and phenylmagnesium chloride

Synthesis in which tri-tert-butylphosphonium tetra-para-tolylborate was handled in air A 30-ml four-necked flask was equipped with a stirrer, a thermometer, a dropping funnel and a reflux condenser. 0.014 g (0.08 mmol) of palladium (II) chloride, 0.0194 g (0.19 mmol) of triethylamine and 5.5 ml of tetrahydrofuran were weighed in the flask, followed by stirring. Further, 0.093 g (0.16 mmol) of tri-tert-butylphosphonium tetra-para-tolylborate obtained in Example B-3 was weighed in air and added into the flask. The flask was purged with argon, followed by stirring at 21° C. for 30 minutes. 1.368 g (8 mmol) of 4-bromotoluene was added, followed by stirring at 21° C. for 30 minutes. 4 ml (8.8 mmol) of 2.2M tetrahydrofuran solution of phenylmagnesium chloride was added dropwise at 21° C. over a period of 10 minutes, followed by stirring at 21° C. for 2 hours. After the completion of the reaction, 5 ml of saturated aqueous ammonium chloride solution was added, followed by separation. The organic phase was purified by column chromatography to afford 1.171 g of 4-methylbiphenyl (yield: 87 mol % based on 4-bromotoluene). The identification of the product was made by mass spectroscopy.

Mass spectrum [EI mode] M/Z 168 (M$^+$)

Example B-24

Similar to Example A-7

Synthesis of 4-vinylbiphenyl from bromobenzene and 4-vinylphenylmagnesium chloride Synthesis in which tri-tert-butylphosphonium tetra-para-tolylborate was handled in air A 100-ml four-necked flask was equipped with a stirrer, a thermometer, a dropping funnel and a reflux condenser. 0.0674 g (0.3 mmol) of palladium (II) acetate and 6 ml of tetrahydrofuran were weighed in the flask, followed by stirring. Further, 0.347 g (0.6 mmol) of tri-tert-butylphosphonium tetra-para-tolylborate obtained in Example B-3 was weighed in air and added into the flask. The flask was purged with argon, followed by stirring at 19° C. for 30 minutes. 4.710 g (30 mmol) of bromobenzene was added, followed by stirring at 19° C. for 30 minutes. 40 ml (50 mmol) of 1.25M tetrahydrofuran solution of 4-vinylphenylmagnesium chloride was added dropwise at 19° C. over a period of 2 hours, followed by stirring at 30° C. for 2 hours. After the completion of the reaction, 10 ml of saturated aqueous ammonium chloride solution was added, followed by separation. The organic phase was purified by column chromatography to afford 4.434 g of 4-vinylbiphenyl (yield: 82 mol % based on bromobenzene). The identification of the product was made by mass spectroscopy.

Mass spectrum [EI mode] M/Z 180 (M$^+$)

Example B-25

Similar to Example A-8

Synthesis of 1-phenylheptane from n-heptyl chloride and phenylmagnesium chloride Synthesis in which tricyclohexylphosphonium tetra-para-tolylborate was handled in air A 30-ml four-necked flask was equipped with a stirrer, a thermometer, a dropping funnel and a reflux condenser. 0.027 g (0.12 mmol) of palladium (II) acetate and 7 ml of N-methylpyrrolidinone were weighed in the flask, followed by stirring. Further, 0.079 g (0.12 mmol) of tricyclohexylphosphonium tetra-para-tolylborate obtained in Example B-16 was weighed in air and added into the flask. The flask was purged with argon, followed by stirring at 25° C. for 30 minutes. 0.404 g (3 mmol) of n-heptyl chloride was added, followed by stirring at 25° C. for 30 minutes. 2 ml (4.4 mmol) of 2.2M tetrahydrofuran solution of phenylmagnesium chloride was added dropwise at 25° C. over a period of 10 minutes, followed by stirring at 25° C. for 19 hours. After the completion of the reaction, 6 ml of tetrahydrofuran and 10 ml of saturated aqueous ammonium chloride solution were added, followed by separation. The organic phase was purified by column chromatography to afford 0.434 g of 1-phenylheptane (yield: 82 mol % based on n-heptyl chloride). The identification of the product was made by mass spectroscopy.

Mass spectrum [EI mode] M/Z 176 (M$^+$)

Example B-26

Similar to Example A-9

Synthesis of 4-cyanobiphenyl from 4-chlorobenzonitrile and phenylzinc chloride

Synthesis in which tri-tert-butylphosphonium tetra-para-tolylborate was handled in air A 30-ml four-necked flask was equipped with a stirrer, a thermometer and a reflux condenser. 0.022 g (0.1 mmol) of palladium (II) acetate and 7 ml of N-methylpyrrolidinone were weighed in the flask, followed by stirring. Further, 0.116 g (0.2 mmol) of tri-tert-butylphosphonium tetra-para-tolylborate obtained in Example B-3 was weighed in air and added into the flask. The flask was purged with argon, followed by stirring at 25° C. for 30 minutes to prepare a reaction liquid.

A 50-ml four-necked flask was equipped with a stirrer, a thermometer, a dropping funnel and a reflux condenser. 1.090 g (8 mmol) of zinc chloride and 4 ml of N-methylpyrrolidinone were weighed in the flask. The flask was purged with argon, followed by stirring. 3.4 ml (7.5 mmol) of 2.2M tetrahydrofuran solution of phenylmagnesium chloride was added dropwise at 25° C. over a period of 30 minutes, followed by stirring at 25° C. for 30 minutes. The reaction liquid previously obtained was added, followed by stirring at 25° C. for 30 minutes. Further, 0.688 g (5 mmol) of 4-chlorobenzonitrile was added, followed by stirring at 120° C. for 9 hours. After the completion of the reaction, 10 ml of toluene and 10 ml of saturated aqueous ammonium chloride solution were added, followed by separation. The organic phase was purified by column chromatography to afford 0.672 g of 4-cyanobiphenyl (yield: 75 mol % based on 4-chlorobenzonitrile). The identification of the product was made by mass spectroscopy.

Mass spectrum [EI mode] M/Z 179 (M$^+$)

Example B-27

Similar to Example A-10

Synthesis of 1-phenylheptane from chlorobenzene and n-heptylzinc chloride

Synthesis in which tri-tert-butylphosphonium tetra-para-tolylborate was handled in air A 30-ml four-necked flask was equipped with a stirrer, a thermometer and a reflux condenser. 0.022 g (0.1 mmol) of palladium (II) acetate and 7 ml of N-methylpyrrolidinone were weighed in the flask, followed by stirring. Further, 0.116 g (0.2 mmol) of tri-tert-butylphosphonium tetra-para-tolylborate obtained in Example B-3 was weighed in air and added into the flask. The flask was purged with argon, followed by stirring at 25° C. for 30 minutes to prepare a reaction liquid.

A 50-ml four-necked flask was equipped with a stirrer, a thermometer, a dropping funnel and a reflux condenser. 1.090 g (8 mmol) of zinc chloride and 4 ml of N-methylpyrrolidinone were weighed in the flask. The flask was purged with argon, followed by stirring. 3.5 ml (7 mmol) of 2M tetrahydrofuran solution of n-heptylmagnesium chloride was added dropwise at 25° C. over a period of 30 minutes, followed by stirring at 25° C. for 30 minutes. The reaction liquid previously obtained was added, followed by stirring at 25° C. for 30 minutes. Further, 0.558 g (5 mmol) of chlorobenzene was added, followed by stirring at 120° C. for 16 hours. After the completion of the reaction, 10 ml of toluene and 10 ml of saturated aqueous ammonium chloride solution were added, followed by separation. The organic phase was purified by column chromatography to afford 0.688 g of 1-phenylheptane (yield: 78 mol % based on chlorobenzene). The identification of the product was made by mass spectroscopy.

Mass spectrum [EI mode] M/Z 176 ($M^+$)

Example B-28

Synthesis of 1-phenylheptane from n-heptyl bromide and trimethoxyphenylsilane

Synthesis in which di-tert-butylmethylphosphonium tetraphenylborate was handled in air A 30-ml four-necked flask was equipped with a stirrer, a thermometer and a reflux condenser. 0.358 g (2 mmol) of n-heptyl bromide, 0.476 g (2.4 mmol) of trimethoxyphenylsilane, 0.021 g (0.08 mmol) of palladium (II) bromide, 4.8 ml (4.8 mmol) of 1M tetrahydrofuran solution of tetra-n-butylammonium fluoride and 4.8 ml of tetrahydrofuran were weighed in the flask, followed by stirring. Further, 0.096 g (0.2 mmol) of di-tert-butylmethylphosphonium tetraphenylborate obtained in Example B-1 was weighed in air and added into the flask. The flask was purged with argon, followed by stirring at 25° C. for 21 hours. After the completion of the reaction, 5 ml of toluene and 10 ml of saturated sodium chloride solution were added, followed by separation. The organic phase was purified by column chromatography to afford 0.300 g of 1-phenylheptane (yield: 85 mol % based on n-heptyl bromide). The identification of the product was made by mass spectroscopy.

Mass spectrum [EI mode] M/Z 176 ($M^+$)

Example B-29

Similar to Example A-11

Synthesis of 2-methylbiphenyl from 2-chlorotoluene and tri-n-butylphenyltin

Synthesis in which tri-tert-butylphosphonium tetra-para-tolylborate was handled in air A 50-ml four-necked flask was equipped with a stirrer, a thermometer and a reflux condenser. 0.045 g (0.2 mmol) of palladium (II) acetate, 1.337 g (8.8 mmol) of cesium fluoride and 4 ml of 1,4-dioxane were weighed in the flask, followed by stirring. Further, 0.463 g (0.8 mmol) of tri-tert-butylphosphonium tetra-para-tolylborate obtained in Example B-3 was weighed in air and added into the flask. The flask was purged with argon, followed by stirring at 25° C. for 30 minutes. 0.506 g (4 mmol) of 2-chlorotoluene and 1.391 g (4.2 mmol) of tri-n-butylphenyltin were added, followed by stirring at 95° C. for 18 hours. After the completion of the reaction, 10 ml of toluene and 10 ml of saturated sodium chloride solution were added, followed by separation. The organic phase was purified by column chromatography to afford 0.511 g of 2-methylbiphenyl (yield: 76 mol % based on 2-chlorotoluene). The identification of the product was made by mass spectroscopy.

Mass spectrum [EI mode] M/Z 168 ($M^+$)

Example B-30

Similar to Example A-12

Synthesis of 2-methylbiphenyl from 2-bromotoluene and tri-n-butylphenyltin

Synthesis in which tri-tert-butylphosphonium tetra-para-tolylborate was handled in air A 50-ml four-necked flask was equipped with a stirrer, a thermometer and a reflux condenser. 0.045 g (0.2 mmol) of palladium (II) acetate, 1.337 g (8.8 mmol) of cesium fluoride and 4 ml of N-methylpyrrolidinone were weighed in the flask, followed by stirring. Further, 0.463 g (0.8 mmol) of tri-tert-butylphosphonium tetra-para-tolylborate obtained in Example B-3 was weighed in air and added into the flask. The flask was purged with argon, followed by stirring at 25° C. for 30 minutes. 0.684 g (4 mmol) of 2-bromotoluene and 1.391 g (4.2 mmol) of tri-n-butylphenyltin were added, followed by stirring at 40° C. for 17 hours. After the completion of the reaction, 10 ml of toluene and 10 ml of saturated sodium chloride solution were added, followed by separation. The organic phase was purified by column chromatography to afford 0.498 g of 2-methylbiphenyl (yield: 74 mol % based on 2-bromotoluene). The identification of the product was made by mass spectroscopy.

Mass spectrum [EI mode] M/Z 168 ($M^+$)

Example B-31

Similar to Example A-13

Synthesis of (E)-3-(4-dimethylaminophenyl)-2-methylacrylic acid methyl ester from 4-dimethylaminobromobenzene and methyl methacrylate Synthesis in which tri-tert-butylphosphonium tetra-para-tolylborate was handled in air A 30-ml four-necked flask was equipped with a stirrer, a thermometer and a reflux condenser. 1.000 g (5 mmol) of 4-dimethylaminobromobenzene, 1.001 g (10 mmol) of methyl methacrylate, 0.011 g (0.012 mmol) of tris(dibenzylideneacetone)dipalladium (0), 1.074 g (5.5 mmol) of dicyclohexylmethylamine and 5 ml of tetrahydrofuran were weighed in the flask, followed by stirring. Further, 0.029 g (0.05 mmol) of tri-tert-butylphosphonium tetra-para-tolylborate obtained in Example B-3 was weighed in air and added into the flask. The flask was purged with argon, followed by stirring at 30° C. for 25 hours. After the completion of the reaction, 5 ml of toluene and 10 ml of saturated sodium chloride solution were added, followed by separation. The organic phase was purified by column chromatography to afford 0.954 g of (E)-3-(4-dimethylaminophenyl)-2-methylacrylic acid methyl ester (yield: 87 mol % based on 4-dimethylaminobromobenzene). The identification of the product was made by H-NMR and $^{13}$C-NMR.

(1) $^1$H-NMR spectrum (δ in $CDCl_3$) 2.15 ppm (s, 3H, $\underline{H}_3C$—C) 2.98 ppm (s, 6H, $\underline{H}_3CN$) 3.78 ppm (s, 3H, $\underline{H}_3CO$) 6.69 ppm (d, J=8.8 Hz, 2H, ring proton) 7.37 ppm (d, J=8.8 Hz, 2H, ring proton) 7.62 ppm (s, 1H, $\underline{H}C$=)

(2) $^{13}$C-NMR spectrum (δ in CDCl$_3$) 14.2, 40.1, 51.8, 111.6, 123.1, 123.7, 131.6, 139.4, 150.3, 169.8 ppm Example B-32

Similar to Example A-14

Synthesis of (trans)-4-acetylstilbene from 4'-chloroacetophenone and styrene

Synthesis in which tri-tert-butylphosphonium tetra-para-tolylborate was handled in air A 30-ml four-necked flask was equipped with a stirrer, a thermometer and a reflux condenser. 0.773 g (5 mmol) of 4'-chloroacetophenone, 1.042 g (10 mmol) of styrene, 0.034 g (0.038 mmol) of tris(dibenzylideneacetone)dipalladium (0), 1.074 g (5.5 mmol) of dicyclohexylmethylamine and 5 ml of tetrahydrofuran were weighed in the flask, followed by stirring. Further, 0.087 g (0.15 mmol) of tri-tert-butylphosphonium tetra-para-tolylborate obtained in Example B-3 was weighed in air and added into the flask. The flask was purged with argon, followed by stirring at 30° C. for 37 hours. After the completion of the reaction, 5 ml of toluene and 10 ml of saturated sodium chloride solution were added, followed by separation. The organic phase was purified by column chromatography to afford 0.841 g of (trans)-4-acetylstilbene (yield: 75 mol % based on 4'-chloroacetophenone). The identification of the product was made by mass spectroscopy, $^1$H-NMR and $^{13}$C-NMR.

(1) Mass spectrum [EI mode] M/Z 222 (M$^+$)

(2) $^1$H-NMR spectrum (δ in CDCl$_3$) 2.60 ppm (s, 3H, $\underline{H}_3$C) 7.11 ppm (d, J=16.5 Hz, 1H, $\underline{H}$C=) 7.22 ppm (d, J=16.5 Hz, 1H, $\underline{H}$C=) 7.24-40 ppm (m, 3H, ring proton) 7.53 ppm (d, J=7.2 Hz, 2H, ring proton) 7.57 ppm (d, J=8.7 Hz, 2H, ring proton) 7.94 ppm (d, J=8.7 Hz, 2H, ring proton)

(3) $^{13}$C-NMR spectrum (δ in CDCl$_3$) 26.9, 126.6, 126.9, 127.5, 128.4, 128.9, 129.0, 131.5, 136.0, 136.8, 142.1, 197.5 ppm Example B-33

Similar to Example A-15

Synthesis of (E)-3-(2,6-dimethylphenyl)-2-methylacrylic acid methyl ester from 2-chloro-meta-xylene and methyl methacrylate Synthesis in which tri-tert-butylphosphonium tetra-para-tolylborate was handled in air A 30-ml four-necked flask was equipped with a stirrer, a thermometer and a reflux condenser. 0.703 g (5 mmol) of 2-chloro-meta-xylene, 1.001 g (10 mmol) of methyl methacrylate, 0.034 g (0.038 mmol) of tris(dibenzylideneacetone) dipalladium (0), 1.074 g (5.5 mmol) of dicyclohexylmethylamine and 5 ml of 1,4-dioxane were weighed in the flask, followed by stirring. Further, 0.087 g (0.15 mmol) of tri-tert-butylphosphonium tetra-para-tolylborate obtained in Example B-3 was weighed in air and added into the flask. The flask was purged with argon, followed by stirring at 120° C. for 37 hours. After the completion of the reaction, 5 ml of toluene and 10 ml of saturated sodium chloride solution were added, followed by separation. The organic phase was purified by column chromatography to afford 0.775 g of (E)-3-(2,6-dimethylphenyl)-2-methylacrylic acid methyl ester (yield: 76 mol % based on 2-chloro-meta-xylene). The identification of the product was made by $^1$H-NMR and $^{13}$C-NMR.

(1) $^1$H-NMR spectrum (δ in CDCl$_3$) 1.71 ppm (d, J=1.1 Hz, 3H, $\underline{H}_3$C—C=) 2.18 ppm (s, 6H, $\underline{H}_3$C) 3.84?ppm (s, 3H, $\underline{H}_3$CO) 7.00-7.15 ppm (m, 3H, ring proton) 7.66 ppm (s, 1H, $\underline{H}$C=)

(2) $^{13}$C-NMR spectrum (δ in CDCl$_3$) 13.6, 19.9, 51.8, 127.2, 127.3, 130.3, 135.0, 135.2, 139.0, 168.2 ppm Example B-34

Similar to Example A-16

Synthesis of diphenylacetylene from bromobenzene and phenylacetylene

Synthesis in which tri-tert-butylphosphonium tetra-para-tolylborate was handled in air A 50-ml four-necked flask was equipped with a stirrer, a thermometer and a reflux condenser. 0.034 g (0.15 mmol) of palladium (II) acetate, 0.019 g (0.1 mmol) of copper (I) iodide, 1.088 g (6 mmol) of dicyclohexylamine and 5 ml of tetrahydrofuran were weighed in the flask, followed by stirring. Further, 0.174 g (0.3 mmol) of tri-tert-butylphosphonium tetra-para-tolylborate obtained in Example B-3 was weighed in air and added into the flask. The flask was purged with argon, followed by stirring at 30° C. for 30 minutes. 0.785 g (5 mmol) of bromobenzene and 1.021 g (10 mmol) of phenylacetylene were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.882 g of diphenylacetylene (yield: 99 mol % based on bromobenzene). The identification of the product was made by mass spectroscopy.

Mass spectrum [EI mode] M/Z 178 (M$^+$)

Example B-35

Similar to Example A-17

Synthesis of diphenylacetylene from bromobenzene and phenylacetylene

Synthesis in which tri-tert-butylphosphonium tetra-para-tolylborate was handled in air A 50-ml four-necked flask was equipped with a stirrer, a thermometer and a reflux condenser. 0.034 g (0.15 mmol) of palladium (II) acetate, 1.088 g (6 mmol) of dicyclohexylamine and 5 ml of tetrahydrofuran were weighed in the flask, followed by stirring. Further, 0.174 g (0.3 mmol) of tri-tert-butylphosphonium tetra-para-tolylborate obtained in Example B-3 was weighed in air and added into the flask. The flask was purged with argon, followed by stirring at 30° C. for 30 minutes. 0.785 g (5 mmol) of bromobenzene and 0.613 g (6 mmol) of phenylacetylene were added, followed by stirring at 30° C. for 14 hours. After the completion of the reaction, 10 ml of tetrahydrofuran, 5 ml of toluene and 15 ml of saturated sodium chloride solution were added, followed by separation. The organic phase was purified by column chromatography to afford 0.838 g of diphenylacetylene (yield: 94 mol % based on bromobenzene). The identification of the product was made by mass spectroscopy.

Mass spectrum [EI mode] M/Z 178 (M$^+$)

Example B-36

Similar to Example A-18

Synthesis of 4-[(trimethylsilyl)ethynyl]benzaldehyde from 4-bromobenzaldehyde and trimethylsilylacetylene Synthesis in which tri-tert-butylphosphonium tetra-para-tolylborate was handled in air A 50-ml four-necked flask was equipped with a stirrer, a thermometer and a reflux condenser. 0.034 g (0.15 mmol) of palladium (II) acetate, 0.019 g (0.1 mmol) of copper (I) iodide, 1.088 g (6 mmol) of dicyclohexylamine and 9 ml of tetrahydrofuran were weighed in the flask, followed by stirring. Further, 0.174 g (0.3 mmol) of tri-tert-butylphosphonium tetra-para-tolylborate obtained in Example B-3 was weighed in air and added into the flask. The flask was purged with argon, followed by stirring at 30° C. for 30 minutes. 0.925 g (5 mmol) of 4-bromobenzaldehyde and 0.589 g (6 mmol) of trimethylsilylacetylene were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.890 g of 4-[(trimethylsilyl)ethynyl]benzaldehyde (yield: 88 mol % based on 4-bromobenzaldehyde). The identification of the product was made by $^1$H-NMR and $^{13}$C-NMR.

(1) $^1$H-NMR spectrum (δ in CDCl$_3$) 0.26 ppm (s, 9H, H$_3$C) 7.59 ppm (d, J=8.1 Hz, 2H, ring proton) 7.81 ppm (d, J=8.1 Hz, 2H, ring proton) 9.99 ppm (s, 1H, HC)

(2) $^{13}$C-NMR spectrum (δ in CDCl$_3$) −0.2, 99.0, 103.8, 129.3, 129.4, 132.5, 135.6, 191.4 ppm

Example B-37

Similar to Example A-19

Synthesis of 4-(N,N-dimethylaminophenyl)-2-methyl-3-butyne-2-ol from 4-bromo-N,N-dimethylaniline and 2-methyl-3-butyne-2-ol Synthesis in which tri-tert-butylphosphonium tetra-para-tolylborate was handled in air A 50-ml four-necked flask was equipped with a stirrer, a thermometer and a reflux condenser. 0.034 g (0.15 mmol) of palladium (II) acetate, 0.019 g (0.1 mmol) of copper (I) iodide, 1.088 g (6 mmol) of dicyclohexylamine and 5 ml of tetrahydrofuran were weighed in the flask, followed by stirring. Further, 0.174 g (0.3 mmol) of tri-tert-butylphosphonium tetra-para-tolylborate obtained in Example B-3 was weighed in air and added into the flask. The flask was purged with argon, followed by stirring at 30° C. for 30 minutes. 1.000 g (5 mmol) of 4-bromo-N,N-dimethylaniline and 0.505 g (6 mmol) of 2-methyl-3-butyne-2-ol were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.875 g of 4-(N,N-dimethylaminophenyl)-2-methyl-3-butyne-2-ol (yield: 86 mol % based on 4-bromo-N,N-dimethylaniline). The identification of the product was made by mass spectroscopy, $^1$H-NMR and $^{13}$C-NMR.

(1) Mass spectrum [EI mode] M/Z 203 (M$^+$)

(2) $^1$H-NMR spectrum (δ in CDCl$_3$) 1.58 ppm (s, 6H, H$_3$CC) 2.86 ppm (s, 6H, H$_3$CN) 3.38 ppm (s, 1H, HO) 6.54 ppm .(d, J=9.0 Hz, 2H, ring proton) 7.76 ppm (d, J=9.0 Hz, 2H, ring proton)

(3) $^{13}$C-NMR spectrum (δ in CDCl$_3$) 31.4, 39.8, 65.0, 82.4, 91.6, 109.6, 111.6, 132.3, 149.7 ppm

Example B-38

Similar to Example A-20

Synthesis of (4-fluorophenyl)-2-methyl-3-butyne-2-ol from 1-bromo-4-fluorobenzene and 2-methyl-3-butyne-2-ol Synthesis in which tri-tert-butylphosphonium tetra-para-tolylborate was handled in air A 50-ml four-necked flask was equipped with a stirrer, a thermometer and a reflux condenser. 0.034 g (0.15 mmol) of palladium (II) acetate, 1.088 g (6 mmol) of dicyclohexylamine and 5 ml of tetrahydrofuran were weighed in the flask, followed by stirring. Further, 0.174 g (0.3 mmol) of tri-tert-butylphosphonium tetra-para-tolylborate obtained in Example B-3 was weighed in air and added into the flask. The flask was purged with argon, followed by stirring at 30° C. for 30 minutes. 0.875 g (5 mmol) of 1-bromo-4-fluorobenzene and 0.505 g (6 mmol) of 2-methyl-3-butyne-2-ol were added, followed by stirring at 30° C. for 17 hours. After the completion of the reaction, 10 ml of tetrahydrofuran, 5 ml of toluene and 15 ml of saturated sodium chloride solution were added, followed by separation. The organic phase was purified by column chromatography to afford 0.862 g of (4-fluorophenyl)-2-methyl-3-butyne-2-ol (yield: 97 mol % based on 1-bromo-4-fluorobenzene). The identification of the product was made by $^1$H-NMR and $^{13}$C-NMR.

(1) $^1$H-NMR spectrum (δ in CDCl$_3$) 1.59 ppm (s, 6H, H$_3$C) 3.41 ppm (s, 1H, HO) 6.88-6.95 ppm (m, 2H, ring proton) 7.30-7.36 ppm (m, 2H, ring proton)

(2) $^{13}$C-NMR spectrum (δ in CDCl$_3$) 31.5, 65.3, 80.8, 93.6, 115.3 (d, J=21.8 Hz), 122.1 (d, J=492.3 Hz), 133.3 (d, J=8.7 Hz), 162.2 (d, J=249.2 Hz) ppm

Example B-39

Similar to Example A-21

Synthesis of 1,2-diphenyl-1-propanone from chlorobenzene and propiophenone

Synthesis in which tri-tert-butylphosphonium tetra-para-tolylborate was handled in air A 30-ml four-necked flask was equipped with a stirrer, a thermometer and a reflux condenser. 0.022 g (0.1 mmol) of palladium (II) acetate, 0.721 g (7.5 mmol) of sodium-tert-butoxide and 5 ml of tetrahydrofuran were weighed in the flask, followed by stirring. Further, 0.058 g (0.1 mmol) of tri-tert-butylphosphonium tetra-para-tolylborate obtained in Example B-3 was weighed in air and added into the flask. The flask was purged with argon, followed by stirring at 22° C. for 30 minutes. 0.563 g (5 mmol) of chlorobenzene was added, followed by stirring at 22° C. for 30 minutes. 0.738 g (5.5 mmol) of propiophenone was added, followed by stirring at 70° C. for 6 hours. After the completion of the reaction, 2.5 ml of water was added, followed by separation. The organic phase was purified by column chromatography to afford 0.810 g of 1,2-diphenyl-1-propanone (yield: 77 mol % based on chlorobenzene). The identification of the product was made by mass spectroscopy, $^1$H-NMR and $^{13}$C-NMR.

(1) Mass spectrum [EI mode] M/Z 210 (M$^+$)

(2) $^1$H-NMR spectrum (δ in CDCl$_3$) 1.54 ppm (d, J=6.8 Hz, 3H, H$_3$C) 4.70 ppm (q, J=6.8 Hz, 1H, HC) 7.17-7.23 ppm (m, 1H, Ph) 7.29-7.30 ppm (m, 4H, Ph) 7.37-7.40 ppm (m, 2H, Ph) 7.48 ppm (t, J=7.3 Hz, 1H, Ph) 7.95 ppm (d, J=7.3 Hz, 2H, Ph)

(3) $^{13}$C-NMR spectrum (δ in CDCl$_3$) 19.6, 47.9, 127.0, 127.8, 128.5, 128.8, 129.0, 132.3, 136.5, 141.6, 200.3 ppm Example B-40

Similar to Example A-22

Synthesis of 1,2-diphenyl-1-propanone from bromobenzene and propiophenone

Synthesis in which tri-tert-butylphosphonium tetra-para-tolylborate was handled in air A 30-ml four-necked flask was equipped with a stirrer, a thermometer and a reflux condenser. 0.011 g (0.05 mmol) of palladium (II) acetate, 1.442 g (15 mmol) of sodium-tert-butoxide and 10 ml of tetrahydrofuran were weighed in the flask, followed by stirring. Further, 0.029 g (0.05 mmol) of tri-tert-butylphosphonium tetra-para-tolylborate obtained in Example B-3 was weighed in air and added into the flask. The flask was purged with argon, followed by stirring at 25° C. for 30 minutes. 1.570 g (10 mmol) of bromobenzene was added, followed by stirring at 25° C. for 30 minutes. 1.476 g (11 mmol) of propiophenone was added, followed by stirring at 25° C. for 17 hours. After the completion of the reaction, 5 ml of water was added, followed by separation. The organic phase was purified by column chromatography to afford 2.061 g of 1,2-diphenyl-1-propanone (yield: 98 mol % based on bromobenzene). The identification of the product was made by mass spectroscopy, $^1$H-NMR and $^{13}$C-NMR.

(1) Mass spectrum [EI mode] M/Z 210 (M$^+$)

(2) $^1$H-NMR spectrum (δ in CDCl$_3$) 1.54 ppm (d, J=6.8 Hz, 3H, H$_3$C) 4.70 ppm (q, J=6.8 Hz, 1H, HC) 7.17-7.23 ppm (m, 1H, Ph) 7.29-7.30 ppm (m, 4H, Ph) 7.37-7.40 ppm (m, 2H, Ph) 7.48 ppm (t, J=7.3 Hz, 1H, Ph) 7.95 ppm (d, J=7.3 Hz, 2H, Ph)

(3) $^{13}$C-NMR spectrum (δ in CDCl$_3$) 19.6, 47.9, 127.0, 127.8, 128.5, 128.8, 129.0, 132.3, 136.5, 141.6, 200.3 ppm Example B-41

Similar to Example A-23

Synthesis of di-tert-butylphenyl malonate from chlorobenzene and di-tert-butyl malonate Synthesis in which tri-tert-butylphosphonium tetra-para-tolylborate was handled in air A 30-ml four-necked flask was equipped with a stirrer, a thermometer and a reflux condenser. 0.013 g (0.06 mmol) of palladium (II) acetate, 0.317 g (3.3 mmol) of sodium-tert-butoxide and 9 ml of dioxane were weighed in the flask, followed by stirring. Further, 0.035 g (0.06 mmol) of tri-tert-butylphosphonium tetra-para-tolylborate obtained in Example B-3 was weighed in air and added into the flask. The flask was purged with argon, followed by stirring at 25° C. for 30 minutes. 0.338 g (3 mmol) of chlorobenzene was added, followed by stirring at 25° C. for 30 minutes. 0.714 g (3.3 mmol) of di-tert-butyl malonate was added, followed by stirring at 100° C. for 12 hours. After the completion of the reaction, 9 ml of tetrahydrofuran and 9 ml of water were added, followed by separation. The organic phase was purified by column chromatography to afford 0.744 g of di-tert-butylphenyl malonate (yield: 85 mol % based on chlorobenzene). The identification of the product was made by $^1$H-NMR and $^{13}$C-NMR.

(1) $^1$H-NMR spectrum (δ in CDCl$_3$) 1.47 ppm (s, 18H, H$_3$C) 4.44 ppm (s, 1H, HC) 7.33-7.40 ppm (m, 5H, Ph)

(2) $^{13}$C-NMR spectrum (δ in CDCl$_3$) 27.9, 60.1, 81.9, 127.8, 128.4, 129.3, 133.5, 167.4 ppm Example B-42

Similar to Example A-24

Synthesis of ethyl-2-phenylcyanoacetate from chlorobenzene and ethyl cyanoacetate Synthesis in which tri-tert-butylphosphonium tetra-para-tolylborate was handled in air A 30-ml four-necked flask was equipped with a stirrer, a thermometer and a reflux condenser. 0.022 g (0.1 mmol) of palladium (II) acetate, 2.459 g (15 mmol) of sodium phosphate and 15 ml of toluene were weighed in the flask, followed by stirring. Further, 0.116 g (0.2 mmol) of tri-tert-butylphosphonium tetra-para-tolylborate obtained in Example B-3 was weighed in air and added into the flask. The flask was purged with argon, followed by stirring at 25° C. for 30 minutes. 0.563 g (5 mmol) of chlorobenzene was added, followed by stirring at 25° C. for 30 minutes. 0.622 g (5.5 mmol) of ethyl cyanoacetate was added, followed by stirring at 100° C. for 12 hours. After the completion of the reaction, 5 ml of water was added, followed by separation. The organic phase was purified by column chromatography to afford 0.502 g of ethyl-2-phenylcyanoacetate (yield: 53 mol % based on chlorobenzene). The identification of the product was made by mass spectroscopy, $^1$H-NMR and $^{13}$C-NMR.

(1) Mass spectrum [EI mode] M/Z 189 (M$^+$)

(2) $^1$H-NMR spectrum (δ in CDCl$_3$) 1.29 ppm (t, J=7.2 Hz, 3H, H$_3$C) 4.21-4.29 ppm (m, 2H, H$_2$C) 4.73 ppm (s, 1H, HC) 7.42-7.49 ppm (m, 5H, Ph)

(3) $^{13}$C-NMR spectrum (δ in CDCl$_3$) 13.9, 43.7, 63.3, 115.7, 127.9, 129.2, 129.3, 130.0, 165.0 ppm Example B-43

Similar to Example A-25

Synthesis of triphenylamine from chlorobenzene and diphenylamine

Synthesis in which tri-tert-butylphosphonium tetra-para-tolylborate was handled in air A 100-ml four-necked flask was equipped with a stirrer, a thermometer and a reflux condenser. 5.403 g (48 mmol) of chlorobenzene, 6.769 g (40 mmol) of diphenylamine, 4.613 g (48 mmol) of sodium-tert-butoxide, 0.002 g (0.01 mmol) of palladium (II) acetate and 5 ml of xylene were weighed in the flask, followed by stirring. Further, 0.023 g (0.04 mmol) of tri-tert-butylphosphonium tetra-para-tolylborate obtained in Example B-3 was weighed in air and added into the flask. The flask was purged with argon, followed by stirring at 100-120° C. for 10 hours. After the completion of the reaction, 45 ml of xylene and 50 ml of saturated sodium chloride solution were added, followed by separation. The organic phase was purified by column chromatography to afford 9.028 g of triphenylamine (yield: 92 mol % based on diphenylamine). The melting point was 125-126° C.

Example B-44

Similar to Example A-26

Synthesis of tert-butyl-2-methylphenyl ether from 2-chlorotoluene and sodium-tert-butoxide Synthesis in which tri-tert-butylphosphonium tetra-para-tolylborate was handled in air A 100-ml four-necked flask was equipped with a stirrer, a thermometer and a reflux condenser. 6.330 g (50 mmol) of 2-chlorotoluene, 5.766 g (60 mmol) of sodium-tert-butoxide, 0.112 g (0.5 mmol) of palladium (II) acetate and 50 ml of xylene were weighed in the flask, followed by stirring. Further, 0.868 g (1.5 mmol) of tri-tert-butylphosphonium tetra-para-tolylborate obtained in Example B-3 was weighed in air and added into the flask. The flask was purged with argon, followed by stirring at 125° C. for 3 hours. After the completion of the reaction, 10 ml of water was added, followed by separation. The organic phase was purified by distillation to afford 7.720 g of tert-butyl-2-methylphenyl ether (yield: 94 mol % based on 2-chlorotoluene). The boiling point was 75° C./9 Torr.

Example B-45

Similar to Example A-27

Synthesis of 2-methoxy-4,2'-dimethylphenyl ether from 2-chlorotoluene and 2-methoxy-4-methylphenol Synthesis in which tri-tert-butylphosphonium tetra-para-tolylborate was handled in air A 200-ml four-necked flask was equipped with a stirrer, a thermometer and a reflux condenser. 1.920 g (48 mmol) of 60 wt % sodium hydride and 50 ml of toluene were weighed in the flask. The flask was purged with argon, followed by stirring. 6.632 g (48 mmol) of 2-methoxy-4-methylphenol was added, followed by stirring at 25° C. for 30 minutes. Further, 5.064 g (40 mmol) of 2-chlorotoluene and 0.449 g (2 mmol) of palladium (II) acetate were added, followed by stirring. Further, 1.157 g (2 mmol) of tri-tert-butylphosphonium tetra-para-tolylborate obtained in Example B-3 was weighed in air and added into the flask, followed by stirring at 104° C. for 9 hours. After the completion of the reaction, 50 ml of saturated sodium chloride solution was added, followed by separation. The organic phase was purified by column chromatography to afford 6.849 g of 2-methoxy-4,2'-dimethylphenyl ether (yield: 75 mol % based on 2-chlorotoluene). The identification of the product was made by mass spectroscopy, $^1$H-NMR and $^{13}$C-NMR.

(1) Mass spectrum [EI mode] M/Z 228 (M$^+$)

(2) $^1$H-NMR spectrum (δ in CDCl$_3$) 2.32 ppm (s, 3H, $\underline{H}_3$C) 2.34 ppm (s, 3H, $\underline{H}_3$C) 3.84 ppm (s, 3H, $\underline{H}_3$CO) 6.68-6.81 ppm (m, 4H, ring proton) 6.95-7.22 ppm (m, 3H, ring proton)

(3) $^{13}$C-NMR spectrum (δ in CDCl$_3$) 16.2, 21.2, 56.0, 113.7, 117.1, 117.2, 119.3, 121.3, 122.8, 126.8, 131.1, 133.7, 143.8, 150.5, 155.8 ppm Example B-46

Production of tricyclopentylphosphonium tetraphenylborate

A 200-ml four-necked flask sufficiently purged with nitrogen was equipped with a stirrer, a thermometer and a reflux condenser. 5.5 g (40 mmol) of trichlorophosphine and 40.0 ml of tetrahydrofuran were weighed in the flask. A cyclopentylmagnesium chloride solution was added dropwise to the flask at an internal temperature of 10-20° C. over a period of 3 hours, wherein the solution had been previously prepared from 13.8 g (132 mmol) of cyclopentyl chloride and 3.2 g (132 mmol) of metallic magnesium in 49 g of tetrahydrofuran. The mixture was stirred at 20-30° C. for 2 hours. Gas chromatography analysis confirmed the disappearance of trichlorophosphine. After the completion of the reaction, 61 ml of toluene was added, and 11.8 g (6 mmol) of 5% sulfuric acid was added dropwise to dissolve the magnesium salt, followed by separation. The organic phase was washed with 11.8 ml of water, and a solution of tricyclopentylphosphine was obtained.

A 100-ml four-necked flask sufficiently purged with argon was equipped with a stirrer, a thermometer and a reflux condenser. The solution of tricyclopentylphosphine prepared above was weighed in the flask, to which 8.0 ml (40 mmol) of 5N hydrochloric acid was added, followed by stirring at 25° C. for 1 hour. The organic phase was analyzed by gas chromatography, which confirmed the disappearance of tricyclopentylphosphine. After the completion of the reaction, the liquid was separated and the aqueous phase was washed with 8.0 ml of heptane. The aqueous phase was assumed to contain tricyclopentylphosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of tricyclopentylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 16.8 g of objective tricyclopentylphosphonium tetraphenylborate as white crystal. The yield (mol %) was 75% based on trichlorophosphine.

The crystal was analyzed by the methods indicated below and was identified to be tricyclopentylphosphonium tetraphenylborate. The analytical values and properties were as follows.

(1) Melting point: 178-187° C. (decomposition)

(2) IR spectrum (KBr) 2359 cm$^{-1}$ (3) $^1$H-NMR spectrum (δ in DMSO-d6) 1.18-1.77 ppm (m, 24H, cyclopentyl secondary) 2.43-2.56 ppm (m, 3H, cyclopentyl tertiary) 5.76 ppm (brd, 1H, J=470.6 Hz, $\underline{H}$—P) 6.79 ppm (t, 4H, J=7.34 Hz, $\underline{Ph}$-B) 6.93 ppm (t, 8H, J=7.34 Hz, $\underline{Ph}$-B) 7.19 ppm (brs, 8H, $\underline{Ph}$-B)

(4) $^{13}$C-NMR spectrum (δ in DMSO-d6) 25.6 ppm (d, J=13.1 Hz, cyclopentyl secondary) 26.8 ppm (d, J=39.8 Hz, cyclopentyl tertiary) 27.0 ppm (d, J=3.1 Hz, cyclopentyl secondary) 121.4 ppm (s, $\underline{Ph}$-B) 125.2 ppm (dd, J=3.1 Hz, 5.6 Hz, $\underline{Ph}$-B) 135.5 ppm (d, J=1.2 Hz, $\underline{Ph}$-B) 163.3 ppm (dd, J=49.1 Hz, 98.8 Hz, $\underline{Ph}$ quaternary-B)

Example B-47

Production of n-butyldicyclohexylphosphonium tetraphenylborate

A 100-ml four-necked flask sufficiently purged with nitrogen was equipped with a stirrer, a thermometer and a reflux condenser. 9.3 g (40 mmol) of dicyclohexylphosphinas chloride and 7.2 ml of tetrahydrofuran were weighed in the flask. A n-butylmagnesium chloride solution was added dropwise to the flask at an internal temperature of 10-20° C. over a period of 1 hour, wherein the solution had been previously prepared from 4.8 g (52 mmol) of n-butyl chloride and 1.3 g (52 mmol) of metallic magnesium in 20 g of tetrahydrofuran. The mixture was stirred at 20-30° C. for 2 hours. Gas chromatography analysis confirmed the disappearance of dicyclohexylphosphinas chloride. After the completion of the reaction, 26 ml of toluene was added, and 11.8 g (6 mmol) of 5% sulfuric acid was added dropwise to dissolve the magnesium salt, followed by separation. The organic phase was washed with 11.8 ml of water, and a solution of n-butyldicyclohexylphosphine was obtained.

A 100-ml four-necked flask sufficiently purged with argon was equipped with a stirrer, a thermometer and a reflux condenser. The solution of n-butyldicyclohexylphosphine prepared above was weighed in the flask, to which 8.0 ml (40 mmol) of 5N hydrochloric acid was added, followed by stirring at 25° C. for 1 hour. The organic phase was analyzed by gas chromatography, which confirmed the disappearance of n-butyldicyclohexylphosphine. After the completion of the reaction, the liquid was separated and the aqueous phase was washed with 8.0 ml of heptane. The aqueous phase was assumed to contain n-butyldicyclohexylphosphine hydrochloride dissolved therein.

A 300-ml four-necked flask was equipped with a stirrer, a thermometer and a reflux condenser. 15.1 g (44 mmol) of sodium tetraphenylborate and 60 ml of water were weighed in the flask, followed by stirring to dissolve sodium tetraphenylborate. While the stirring was continuously carried out, the aqueous solution of n-butyldicyclohexylphosphine hydrochloride previously obtained was added to the solution, and the mixture was stirred at 25° C. for 3 hours. After the completion of the reaction, the precipitated product was filtered off. The so obtained crystal was suspended in 100 ml of toluene at 50° C., and the suspension was cooled to 25° C. and filtered. The product filtered off was washed with 100 ml of toluene. The crystal was then suspended in 100 ml of methanol at 50° C., and the suspension was cooled to 25° C. and filtered. The product filtered off was washed with 100 ml of methanol. The crystal obtained was dried to give 17.2 g of objective n-butyldicyclohexylphosphonium tetraphenylborate as white crystal. The yield (mol %) was 75% based on dicyclohexylphosphinas chloride.

The crystal was analyzed by the methods indicated below and was identified to be n-butyldicyclohexylphosphonium tetraphenylborate. The analytical values and properties were as follows.

(1) Melting point: 175-180° C. (decomposition temperature)

(2) IR spectrum (KBr) 2359 cm$^{-1}$ (3) $^1$H-NMR spectrum (δ in DMSO-d6) 0.93 ppm (t, 3H, J=7.34 Hz, $\underline{H}_3$C—(CH$_2$)$_3$—P) 1.17-1.89 ppm (m, 24H, cyclohexyl secondary, H$_3$C—(C$\underline{H}_2$)$_3$—P) 2.28-2.56 ppm (m, 4H, cyclohexyl tertiary, H$_3$C—(C$\underline{H}_2$)$_3$—P) 5.34-7.18 ppm (brd, 1H, $\underline{H}$—P) 6.79 ppm (t, 4H, J=7.15 Hz, $\underline{Ph}$-B) 6.92 ppm (t, 8H, J=7.15 Hz, $\underline{Ph}$-B) 7.19 ppm (brs, 8H, $\underline{Ph}$-B)

(4) $^{13}$C-NMR spectrum (δ in DMSO-d6) 13.1 ppm (s, $\underline{C}$H$_3$—CH$_2$—CH$_2$—CH$_2$—P) 14.3 ppm (d, J=43.2 Hz, CH$_3$—CH$_2$—CH$_2$—$\underline{c}$H$_2$—P) 23.0 ppm (d, J=14.3 Hz, CH$_3$—CH$_2$—$\underline{C}$H$_2$—CH$_2$—P) 24.6 ppm (d, J=1.2 Hz, cyclohexyl secondary) 25.9 ppm (d, J=12.5 Hz, cyclohexyl secondary) 26.2 ppm (d, J=5.0 Hz, CH$_3$—$\underline{C}$H$_2$—CH$_2$—CH$_2$—P) 27.9 ppm (d, J=3.4 Hz, cyclohexyl secondary) 28.8 ppm (d, J=37.0 Hz, cyclohexyl tertiary) 121.4 ppm (s, $\underline{Ph}$-B) 125.2 ppm (dd, J=3.1 Hz, 5.6 Hz, $\underline{Ph}$-B) 135.6 ppm (d, J=1.2 Hz, $\underline{Ph}$-B) 163.3 ppm (dd, J=49.1 Hz, 98.8 Hz, $\underline{Ph}$ quaternary-B)

Example B-48

Synthesis of triphenylamine from bromobenzene and diphenylamine

Synthesis in which n-butyldicyclohexylphosphonium tetraphenylborate was handled in air A 100-ml four-necked flask was equipped with a stirrer, a thermometer and a reflux condenser. 7.536 g (48 mmol) of bromobenzene, 6.769 g (40 mmol) of diphenylamine, 4.613 g (48 mmol) of sodium-tert-butoxide, 0.090 g (0.40 mmol) of palladium (II) acetate and 5 ml of xylene were weighed in the flask, followed by stirring. Further, 0.690 g (1.20 mmol) of n-butyldicyclohexylphosphonium tetraphenylborate obtained in Example B-47 was weighed in air and added into the flask. The flask was purged with argon, followed by stirring at 125° C. for 4 hours. After the completion of the reaction, 45 ml of xylene and 50 ml of saturated sodium chloride solution were added, followed by separation. The organic phase was purified by column chromatography to afford 8.345 g of triphenylamine (yield: 85 mol % based on diphenylamine). The melting point was 125-126° C.

Example B-49

Synthesis of triphenylamine from bromobenzene and diphenylamine

Synthesis in which di-tert-butylphenylphosphonium tetraphenylborate was handled in air A 100-ml four-necked flask was equipped with a stirrer, a thermometer and a reflux condenser. 7.536 g (48 mmol) of bromobenzene, 6.769 g (40 mmol) of diphenylamine, 4.613 g (48 mmol) of sodium-tert-butoxide, 0.009 g (0.04 mmol) of palladium (II) acetate and 5 ml of xylene were weighed in the flask, followed by stirring. Further, 0.065 g (0.12 mmol) of di-tert-butylphenylphosphonium tetraphenylborate obtained in Example B-9 was weighed in air and added into the flask. The flask was purged with argon, followed by stirring at 125° C. for 4 hours. After the completion of the reaction, 45 ml of xylene and 50 ml of saturated sodium chloride solution were added, followed by separation. The organic phase was purified by column chromatography to afford 9.028 g of triphenylamine (yield: 92 mol % based on diphenylamine). The melting point was 125-126° C.

Example B-50

Synthesis of triphenylamine from bromobenzene and biphenylamine

Synthesis in which 2-biphenylyl-di-tert-butylphosphonium tetraphenylborate was handled in air A 100-ml four-necked flask was equipped with a stirrer, a thermometer and a reflux condenser. 7.536 g (48 mmol) of bromobenzene, 6.769 g (40 mmol) of diphenylamine, 4.613 g (48 mmol) of sodium-tert-butoxide, 0.009 g (0.04 mmol) of palladium (II) acetate and 5 ml of xylene were weighed in the flask, followed by stirring. Further, 0.074 g (0.12 mmol) of 2-biphenylyl-di-tert-butylphosphonium tetraphenylborate obtained in Example B-10 was weighed in air and added into the flask. The flask was purged with argon, followed by stirring at 125° C. for 4 hours. After the completion of the reaction, 45 ml of xylene and 50 ml of saturated sodium chloride solution were added, followed by separation. The organic phase was purified by column chromatography to afford 8.537 g of triphenylamine (yield: 87 mol % based on diphenylamine). The melting point was 125-126° C.

Example B-51

Synthesis of triphenylamine from bromobenzene and diphenylamine

Synthesis in which di-tert-butyl-1-naphthylphosphonium tetraphenylborate was handled in air A 100-ml four-necked flask was equipped with a stirrer, a thermometer and a reflux condenser. 7.536 g (48 mmol) of bromobenzene, 6.769 g (40 mmol) of diphenylamine, 4.613 g (48 mmol) of sodium-tert-butoxide, 0.009 g (0.04 mmol) of palladium (II) acetate and 5 ml of xylene were weighed in the flask, followed by stirring. Further, 0.071 g (0.12 mmol) of di-tert-butyl-1-naphthylphosphonium tetraphenylborate obtained in Example B-11 was weighed in air and added into the flask. The flask was purged with argon, followed by stirring at 125° C. for 4 hours. After the completion of the reaction, 45 ml of xylene and 50 ml of saturated sodium chloride solution were added, followed by separation. The organic phase was purified by column chromatography to afford 8.341 g of triphenylamine (yield: 85 mol % based on diphenylamine). The melting point was 125-126° C.

Comparative Example 1

Synthesis of 1-phenylheptane from n-heptyl bromide and phenylboronic acid

Synthesis in which di-tert-butylmethylphosphine was handled in argon

The procedures in Example B-18 were repeated except that 0.240 g (0.5 mmol) of di-tert-butylmethylphosphonium tetraphenylborate of Example B-18 was replaced with 0.080 g (0.5 mmol) of di-tert-butylmethylphosphine, and except that the procedures were carried out in a glove box in which an argon atmosphere was strictly maintained. Consequently, 0.749 g of 1-phenylheptane was obtained (yield: 85 mol % based on n-heptyl bromide). The identification of the product was made by mass spectroscopy.

Mass spectrum [EI mode] M/Z 176 ($M^+$)

Comparative Example 2

Synthesis of 1-phenylheptane from n-heptyl bromide and phenylboronic acid

Synthesis in which di-tert-butylmethylphosphine was handled in air

The procedures in Example B-18 were repeated except that 0.240 g (0.5 mmol) of di-tert-butylmethylphosphonium tetraphenylborate of Example B-18 was replaced with 0.080 g (0.5 mmol) of di-tert-butylmethylphosphine. Di-tert-butylmethylphosphine generated white smoke while being handled in air. Little 1-phenylheptane formed.

Comparative Example 3

Synthesis of 2-ortho-tolylpyridine from 2-chloropyridine and ortho-tolylboronic acid Synthesis in which tri-tert-butylphosphine was handled in argon The procedures in Example A-S or B-21 were repeated except that 0.026 g (0.05 mmol) of tri-tert-butylphosphonium tetraphenylborate of Example A-5 or 0.029 g (0.05 mmol) of tri-tert-butylphosphonium tetra-para-tolylborate of Example B-21 was replaced with 0.010 g (0.05 mmol) of tri-tert-butylphosphine, and except that the procedures were carried out in a glove box in which an argon atmosphere was strictly maintained. Consequently, 0.694 g of 2-ortho-tolylpyridine was obtained (yield: 82 mol % based on 2-chloropyridine). The identification of the product was made by mass spectroscopy.

Mass spectrum [EI mode] M/Z 169 ($M^+$)

Comparative Example 4

Synthesis of 2-ortho-tolylpyridine from 2-chloropyridine and ortho-tolylboronic acid Synthesis in which tri-tert-butylphosphine was handled in air The procedures in Example A-S or B-21 were repeated except that 0.026 g (0.05 mmol) of tri-tert-butylphosphonium tetraphenylborate of Example A-5 or 0.029 g (0.05 mmol) of tri-tert-butylphosphonium tetra-para-tolylborate of Example B-21 was replaced with 0.010 g (0.05 mmol) of tri-tert-butylphosphine. Tri-tert-butylphosphine generated white smoke while being handled in air. Little 2-ortho-tolylpyridine formed.

Comparative Example 5

Synthesis of 1-phenylheptane from n-heptyl bromide and phenylmagnesium chloride

Synthesis in which di-tert-butylmethylphosphine was handled in argon

The procedures in Example B-22 were repeated except that 0.096 g (0.2 mmol) of di-tert-butylmethylphosphonium tetraphenylborate of Example B-22 was replaced with 0.032 g (0.2 mmol) of di-tert-butylmethylphosphine, and except that the procedures were carried out in a glove box in which an argon atmosphere was strictly maintained. Consequently, 2.992 g of 1-phenylheptane was obtained (yield: 85 mol % based on n-heptyl bromide). The identification of the product was made on the basis of a mass spectrum, which was in agreement with that of Example B-22.

Comparative Example 6

Synthesis of 1-phenylheptane from n-heptyl bromide and phenylmagnesium chloride

Synthesis in which di-tert-butylmethylphosphine was handled in air

The procedures in Example B-22 were repeated except that 0.096 g (0.2 mmol) of di-tert-butylmethylphosphonium tetraphenylborate of Example B-22 was replaced with 0.032 g (0.2 mmol) of di-tert-butylmethylphosphine. Di-tert-butylmethylphosphine generated white smoke while being handled in air. Little 1-phenylheptane formed.

Comparative Example 7

Synthesis of 4-methylbiphenyl from 4-bromotoluene and phenylmagnesium chloride

Synthesis in which tri-tert-butylphosphine was handled in argon

The procedures in Example A-6 or B-23 were repeated except that 0.084 g (0.16 mmol) of tri-tert-butylphosphonium tetraphenylborate of Example A-6 or 0.093 g (0.16 mmol) of tri-tert-butylphosphonium tetra-para-tolylborate of Example B-23 was replaced with 0.032 g (0.16 mmol) of tri-tert-butylphosphine, and except that the procedures were carried out in a glove box in which an argon atmosphere was strictly maintained. Consequently, 1.184 g of 4-methylbiphenyl was obtained (yield: 88 mol % based on 4-bromotoluene). The identification of the product was made on the basis of a mass spectrum, which was in agreement with that of Example A-6 or B-23.

Comparative Example 8

Synthesis of 4-methylbiphenyl from 4-bromotoluene and phenylmagnesium chloride

Synthesis in which tri-tert-butylphosphine was handled in air

The procedures in Example A-6 or B-23 were repeated except that 0.084 g (0.16 mmol) of tri-tert-butylphosphonium tetraphenylborate of Example A-6 or 0.093 g (0.16 mmol) of tri-tert-butylphosphonium tetra-para-tolylborate of Example B-23 was replaced with 0.032 g (0.16 mmol) of tri-tert-butylphosphine. Tri-tert-butylphosphine generated white smoke while being handled in air. Little 4-methylbiphenyl formed.

Comparative Example 9

Synthesis of 4-vinylbiphenyl from bromobenzene and 4-vinylphenylmagnesium chloride Synthesis in which tri-tert-butylphosphine was handled in argon The procedures in Example A-7 or B-24 were repeated except that 0.314 g (0.6 mmol) of tri-tert-butylphosphonium tetraphenylborate of Example A-7 or 0.347 g (0.6 mmol) of tri-tert-butylphosphonium tetra-para-tolylborate of Example B-24 was replaced with 0.121 g (0.6 mmol) of tri-tert-butylphosphine, and except that the procedures were carried out in a glove box in which an argon atmosphere was strictly maintained. Consequently, 4.434 g of 4-vinylbiphenyl was obtained (yield: 82 mol % based on bromobenzene). The identification of the product was made on the basis of a mass spectrum, which was in agreement with that of Example A-7 or B-24.

Comparative Example 10

Synthesis of 4-vinylbiphenyl from bromobenzene and 4-vinylphenylmagnesium chloride Synthesis in which tri-tert-butylphosphine was handled in air The procedures in Example A-7 or B-24 were repeated except that 0.314 g (0.6 mmol) of tri-tert-butylphosphonium tetraphenylborate of Example A-7 or 0.347 g (0.6 mmol) of tri-tert-butylphosphonium tetra-para-tolylborate of Example B-24 was replaced with 0.121 g (0.6 mmol) of tri-tert-butylphosphine. Tri-tert-butylphosphine generated white smoke while being handled in air. Little 4-vinylbiphenyl formed.

Comparative Example 11

Synthesis of 1-phenylheptane from n-heptyl chloride and phenylmagnesium chloride Synthesis in which tricyclohexylphosphine was handled in argon The procedures in Example A-8 or B-25 were repeated except that 0.072 g (0.12 mmol) of tricyclohexylphosphonium tetraphenylborate of Example A-8 or 0.079 g (0.12 mmol) of tricyclohexylphosphonium tetra-para-tolylborate of Example B-25 was replaced with 0.034 g (0.12 mmol) of tricyclohexylphosphine, and except that the procedures were carried out in a glove box in which an argon atmosphere was strictly maintained. Consequently, 0.434 g of 1-phenylheptane was obtained (yield: 82 mol % based on n-heptyl chloride). The identification of the product was made on the basis of a mass spectrum, which was in agreement with that of Example A-8 or B-25.

Comparative Example 12

Synthesis of 1-phenylheptane from n-heptyl chloride and phenylmagnesium chloride

Synthesis in which tricyclohexylphosphine was handled in air

The procedures in Example A-8 or B-25 were repeated except that 0.072 g (0.12 mmol) of tricyclohexylphosphonium tetraphenylborate of Example A-8 or 0.079 g (0.12 mmol) of tricyclohexylphosphonium tetra-para-tolylborate of Example B-25 was replaced with 0.034 g (0.12 mmol) of tricyclohexylphosphine. Tricyclohexylphosphine generated white smoke while being handled in air. Little 1-phenylheptane formed.

Comparative Example 13

Synthesis of 4-cyanobiphenyl from 4-chlorobenzonitrile and phenylzinc chloride

Synthesis in which tri-tert-butylphosphine was handled in argon

The procedures in Example A-9 or B-26 were repeated except that 0.105 g (0.2 mmol) of tri-tert-butylphosphonium tetraphenylborate of Example A-9 or 0.116 g (0.2 mmol) of tri-tert-butylphosphonium tetra-para-tolylborate of Example B-26 was replaced with 0.040 g (0.2 mmol) of tri-tert-butylphosphine, and except that the procedures were carried out in a glove box in which an argon atmosphere was strictly maintained. Consequently, 0.672 g of 4-cyanobiphenyl was obtained (yield: 75 mol % based on 4-chlorobenzonitrile). The identification of the product was made on the basis of a mass spectrum, which was in agreement with that of Example A-9 or B-26.

Comparative Example 14

Synthesis of 4-cyanobiphenyl from 4-chlorobenzonitrile and phenylzinc chloride

Synthesis in which tri-tert-butylphosphine was handled in air

The procedures in Example A-9 or B-26 were repeated except that 0.105 g (0.2 mmol) of tri-tert-butylphosphonium tetraphenylborate of Example A-9 or 0.116 g (0.2 mmol) of tri-tert-butylphosphonium tetra-para-tolylborate of Example B-26 was replaced with 0.040 g (0.2 mmol) of tri-tert-butylphosphine. Tri-tert-butylphosphine generated white smoke while being handled in air. Little 4-cyanobiphenyl formed.

Comparative Example 15

Synthesis of 1-phenylheptane from chlorobenzene and n-heptylzinc chloride

Synthesis in which tri-tert-butylphosphine was handled in argon

The procedures in Example A-10 or B-27 were repeated except that 0.105 g (0.2 mmol) of tri-tert-butylphosphonium tetraphenylborate of Example A-10 or 0.116 g (0.2 mmol) of tri-tert-butylphosphonium tetra-para-tolylborate of Example B-27 was replaced with 0.040 g (0.2 mmol) of tri-tert-butylphosphine, and except that the procedures were carried out in a glove box in which an argon atmosphere was strictly maintained. Consequently, 0.688 g of 1-phenylheptane was obtained (yield: 78 mol % based on chlorobenzene). The identification of the product was made on the basis of a mass spectrum, which was in agreement with that of Example A-10 or B-27.

Comparative Example 16

Synthesis of 1-phenylheptane from chlorobenzene and n-heptylzinc chloride

Synthesis in which tri-tert-butylphosphine was handled in air

The procedures in Example A-10 or B-27 were repeated except that 0.105 g (0.2 mmol) of tri-tert-butylphosphonium tetraphenylborate of Example A-10 or 0.116 g (0.2 mmol) of tri-tert-butylphosphonium tetra-para-tolylborate of Example B-27 was replaced with 0.040 g (0.2 mmol) of tri-tert-butylphosphine. Tri-tert-butylphosphine generated white smoke while being handled in air. Little 1-phenylheptane formed.

Comparative Example 17

Synthesis of 1-phenylheptane from n-heptyl bromine and trimethoxyphenylsilane

Synthesis in which di-tert-butylmethylphosphine was handled in argon

The procedures in Example B-28 were repeated except that 0.096 g (0.2 mmol) of di-tert-butylmethylphosphonium tetraphenylborate of Example B-28 was replaced with 0.032 g (0.2 mmol) of di-tert-butylmethylphosphine, and except that the procedures were carried out in a glove box in which an argon atmosphere was strictly maintained. Consequently, 0.300 g of 1-phenylheptane was obtained (yield: 85 mol % based on n-heptyl bromide). The identification of the product was made on the basis of a mass spectrum, which was in agreement with that of Example B-28.

Comparative Example 18

Synthesis of 1-phenylheptane from n-heptyl bromine and trimethoxyphenylsilane

Synthesis in which di-tert-butylmethylphosphine was handled in air

The procedures in Example B-28 were repeated except that 0.096 g (0.2 mmol) of di-tert-butylmethylphosphonium tetraphenylborate of Example B-28 was replaced with 0.032 g (0.2 mmol) of di-tert-butylmethylphosphine. Di-tert-butylmethylphosphine generated white smoke while being handled in air. Little 1-phenylheptane formed.

Comparative Example 19

Synthesis of 2-methylbiphenyl from 2-chlorotoluene and tri-n-butylphenyltin

Synthesis in which tri-tert-butylphosphine was handled in argon

The procedures in Example A-11 or B-29 were repeated except that 0.418 g (0.8 mmol) of tri-tert-butylphosphonium tetraphenylborate of Example A-11 or 0.463 g (0.8 mmol) of tri-tert-butylphosphonium tetra-para-tolylborate of Example B-29 was replaced with 0.162 g (0.8 mmol) of tri-tert-butylphosphine, and except that the procedures were carried out in a glove box in which an argon atmosphere was strictly maintained. Consequently, 0.513 g of 2-methylbiphenyl was obtained (yield: 76 mol % based on 2-chlorotoluene). The identification of the product was made on the basis of a mass spectrum, which was in agreement with that of Example A-11 or B-29.

Comparative Example 20

Synthesis of 2-methylbiphenyl from 2-chlorotoluene and tri-n-butylphenyltin

Synthesis in which tri-tert-butylphosphine was handled in air

The procedures in Example A-11 or B-29 were repeated except that 0.418 g (0.8 mmol) of tri-tert-butylphosphonium tetraphenylborate of Example A-11 or 0.463 g (0.8 mmol) of tri-tert-butylphosphonium tetra-para-tolylborate of Example B-29 was replaced with 0.162 g (0.8 mmol) of tri-tert-butylphosphine. Tri-tert-butylphosphine generated white smoke while being handled in air. Little 2-methylbiphenyl formed.

Comparative Example 21

Synthesis of 2-methylbiphenyl from 2-bromotoluene and tri-n-butylphenyltin

Synthesis in which tri-tert-butylphosphine was handled in argon

The procedures in Example A-12 or B-30 were repeated except that 0.418 g (0.8 mmol) of tri-tert-butylphosphonium tetraphenylborate of Example A-12 or 0.463 g (0.8 mmol) of tri-tert-butylphosphonium tetra-para-tolylborate of Example B-30 was replaced with 0.162 g (0.8 mmol) of tri-tert-butylphosphine, and except that the procedures were carried out in a glove box in which an argon atmosphere was strictly maintained. Consequently, 0.472 g of 2-methylbiphenyl was obtained (yield: 70 mol % based on 2-bromotoluene). The identification of the product was made on the basis of a mass spectrum, which was in agreement with that of Example A-12 or B-30.

Comparative Example 22

Synthesis of 2-methylbiphenyl from 2-bromotoluene and tri-n-butylphenyltin

Synthesis in which tri-tert-butylphosphine was handled in air

The procedures in Example A-12 or B-30 were repeated except that 0.418 g (0.8 mmol) of tri-tert-butylphosphonium tetraphenylborate of Example A-12 or 0.463 g (0.8 mmol) of tri-tert-butylphosphonium tetra-para-tolylborate of Example B-30 was replaced with 0.162 g (0.8 mmol) of tri-tert-butylphosphine. Tri-tert-butylphosphine generated white smoke while being handled in air. Little 2-methylbiphenyl formed.

Comparative Example 23

Synthesis of (E)-3-(4-dimethylaminophenyl)-2-methylacrylic acid methyl ester from 4-dimethylaminobromobenzene and methyl methacrylate Synthesis in which tri-tert-butylphosphine was handled in argon The procedures in Example A-13 or B-31 were repeated except that 0.026 g (0.05 mmol) of tri-tert-butylphosphonium tetraphenylborate of Example A-13 or 0.029 g (0.05 mmol) of tri-tert-butylphosphonium tetra-para-tolylborate of Example B-31 was replaced with 0.010 g (0.05 mmol) of tri-tert-butylphosphine, and except that the procedures were carried out in a glove box in which an argon atmosphere was strictly maintained. Consequently, 0.944 g of (E)-3-(4-dimethylaminophenyl)-2-methylacrylic acid methyl ester was obtained (yield: 86 mol % based on 4-dimethylaminobromobenzene). The identification of the product was made by $^1$H-NMR and $^{13}$C-NMR, and the results were in agreement with those of Example A-13 or B-31.

Comparative Example 24

Synthesis of (E)-3-(4-dimethylaminophenyl)-2-methylacrylic acid methyl ester from 4-dimethylaminobromobenzene and methyl methacrylate Synthesis in which tri-tert-butylphosphine was handled in air The procedures in Example A-13 or B-31 were repeated except that 0.026 g (0.05 mmol) of tri-tert-butylphosphonium tetraphenylborate of Example A-13 or 0.029 g (0.05 mmol) of tri-tert-butylphosphonium tetra-para-tolylborate of Example B-31 was replaced with 0.010 g (0.05 mmol) of tri-tert-butylphosphine. Tri-tert-butylphosphine generated white smoke while being handled in air. Little (E)-3-(4-dimethylaminophenyl)-2-methylacrylic acid methyl ester formed.

Comparative Example 25

Synthesis of (trans)-4-acetylstilbene from 4'-chloroacetophenone and styrene

Synthesis in which tri-tert-butylphosphine was handled in argon

The procedures in Example A-14 or B-32 were repeated except that 0.078 g (0.15 mmol) of tri-tert-butylphosphonium tetraphenylborate of Example A-14 or 0.087 g (0.15 mmol) of tri-tert-butylphosphonium tetra-para-tolylborate of Example B-32 was replaced with 0.030 g (0.15 mmol) of tri-tert-butylphosphine, and except that the procedures were carried out in a glove box in which an argon atmosphere was strictly maintained. Consequently, 0.828 g of (trans)-4-acetylstilbene was obtained (yield: 75 mol % based on 4'-chloroacetophenone). The identification of the product was made by mass spectroscopy, $^1$H-NMR and $^{13}$C-NMR, and the results were in agreement with those of Example A-14 or B-32.

Comparative Example 26

Synthesis of (trans)-4-acetylstilbene from 4'-chloroacetophenone and styrene

Synthesis in which tri-tert-butylphosphine was handled in air

The procedures in Example A-14 or B-32 were repeated except that 0.078 g (0.15 mmol) of tri-tert-butylphosphonium tetraphenylborate of Example A-14 or 0.087 g (0.15 mmol) of tri-tert-butylphosphonium tetra-para-tolylborate of Example B-32 was replaced with 0.030 g (0.15 =mol) of tri-tert-butylphosphine. Tri-tert-butylphosphine generated white smoke while being handled in air. Little (trans)-4-acetylstilbene formed.

Comparative Example 27

Synthesis of (E)-3-(2,6-dimethylphenyl)-2-methylacrylic acid methyl ester from 2-chloro-meta-xylene and methyl methacrylate Synthesis in which tri-tert-butylphosphine was handled in argon The procedures in Example A-15 or B-33 were repeated except that 0.078 g (0.15 mmol) of tri-tert-butylphosphonium tetraphenylborate of Example A-15 or 0.087 g (0.15 mmol) of tri-tert-butylphosphonium tetra-para-tolylborate of Example B-33 was replaced with 0.030 g (0.15 mmol) of tri-tert-butylphosphine, and except that the procedures were carried out in a glove box in which an argon atmosphere was strictly maintained. Consequently, 0.776 g of (E)-3-(2,6-dimethylphenyl)-2-methylacrylic acid methyl ester was obtained (yield: 76 mol % based on 2-chloro-meta-xylene) The identification of the product was made by H-NMR and $^{13}$C-NMR, and the results were in agreement with those of Example A-15 or B-33.

Comparative Example 28

Synthesis of (E)-3-(2,6-dimethylphenyl)-2-methylacrylic acid methyl ester from 2-chloro-meta-xylene and methyl methacrylate Synthesis in which tri-tert-butylphosphine was handled in air The procedures in Example A-15 or B-33 were repeated except that 0.078 g (0.15 mmol) of tri-tert-butylphosphonium tetraphenylborate of Example A-15 or 0.087 g (0.15 mmol) of tri-tert-butylphosphonium tetra-para-tolylborate of Example B-33 was replaced with 0.030 g (0.15 mmol) of tri-tert-butylphosphine. Tri-tert-butylphosphine generated white smoke while being handled in air. Little (E)-3-(2,6-dimethylphenyl)-2-methylacrylic acid methyl ester formed.

Comparative Example 29

Synthesis of diphenylacetylene from bromobenzene and phenylacetylene

Synthesis in which tri-tert-butylphosphine was handled in argon

The procedures in Example A-16 or B-34 were repeated except that 0.157 g (0.3 mmol) of tri-tert-butylphosphonium tetraphenylborate of Example A-16 or 0.174 g (0.3 mmol) of tri-tert-butylphosphonium tetra-para-tolylborate of Example B-34 was replaced with 0.061 g (0.3 mmol) of tri-tert-butylphosphine, and except that the procedures were carried out in a glove box in which an argon atmosphere was strictly maintained. Consequently, 0.869 g of diphenylacetylene was obtained (yield: 98 mol % based on bromobenzene). The identification of the product was made on the basis of a mass spectrum, which was in agreement with that of Example A-16 or B-34.

Comparative Example 30

Synthesis of diphenylacetylene from bromobenzene and phenylacetylene

Synthesis in which tri-tert-butylphosphine was handled in air

The procedures in Example A-16 or B-34 were repeated except that 0.157 g (0.3 mmol) of tri-tert-butylphosphonium tetraphenylborate of Example A-16 or 0.174 g (0.3 mmol) of tri-tert-butylphosphonium tetra-para-tolylborate of Example B-34 was replaced with 0.061 g (0.3 mmol) of tri-tert-butylphosphine. Tri-tert-butylphosphine generated white smoke while being handled in air. Little diphenylacetylene formed.

Comparative Example 31

Synthesis of diphenylacetylene from bromobenzene and phenylacetylene

Synthesis in which tri-tert-butylphosphine was handled in argon

The procedures in Example A-17 or B-35 were repeated except that 0.157 g (0.3 mmol) of tri-tert-butylphosphonium tetraphenylborate of Example A-17 or 0.174 g (0.3 mmol) of tri-tert-butylphosphonium tetra-para-tolylborate of Example B-35 was replaced with 0.061 g (0.3 mmol) of tri-tert-butylphosphine, and except that the procedures were carried out in a glove box in which an argon atmosphere was strictly maintained. Consequently, 0.833 g of diphenylacetylene was obtained (yield: 94 mol % based on bromobenzene). The identification of the product was made on the basis of a mass spectrum, which was in agreement with that of Example A-17 or B-35.

Comparative Example 32

Synthesis of diphenylacetylene from bromobenzene and phenylacetylene

Synthesis in which tri-tert-butylphosphine was handled in air

The procedures in Example A-17 or B-35 were repeated except that 0.157 g (0.3 mmol) of tri-tert-butylphosphonium tetraphenylborate of Example A-17 or 0.174 g (0.3 mmol) of tri-tert-butylphosphonium tetra-para-tolylborate of Example B-35 was replaced with 0.061 g (0.3 mmol) of tri-tert-butylphosphine. Tri-tert-butylphosphine generated white smoke while being handled in air. Little diphenylacetylene formed.

Comparative Example 33

Synthesis of 4-[(trimethylsilyl)ethynyl]benzaldehyde from 4-bromobenzaldehyde and trimethylsilylacetylene Synthesis in which tri-tert-butylphosphine was handled in argon The procedures in Example A-18 or B-36 were repeated except that 0.157 g (0.3 mmol) of tri-tert-butylphosphonium tetraphenylborate of Example A-18 or 0.174 g (0.3 mmol) of tri-tert-butylphosphonium tetra-para-tolylborate of Example B-36 was replaced with 0.061 g (0.3 mmol) of tri-tert-butylphosphine, and except that the procedures were carried out in a glove box in which an argon atmosphere was strictly maintained. Consequently, 0.894 g of 4-[(trimethylsilyl)ethynyl]benzaldehyde was obtained (yield: 88 mol % based on 4-bromobenzaldehyde). The identification of the product was made by $^1$H-NMR and $^{13}$C-NMR, and the results were in agreement with those of Example A-18 or B-36.

Comparative Example 34

Synthesis of 4-[(trimethylsilyl)ethynyl]benzaldehyde from 4-bromobenzaldehyde and trimethylsilylacetylene Synthesis in which tri-tert-butylphosphine was handled in air The procedures in Example A-18 or B-36 were repeated except that 0.157 g (0.3 mmol) of tri-tert-butylphosphonium tetraphenylborate of Example A-18 or 0.174 g (0.3 mmol) of tri-tert-butylphosphonium tetra-para-tolylborate of Example B-36 was replaced with 0.061 g (0.3 mmol) of tri-tert-butylphosphine. Tri-tert-butylphosphine generated white smoke while being handled in air. Little 4-[(trimethylsilyl)ethynyl]benzaldehyde formed.

Comparative Example 35

Synthesis of 4-(N,N-dimethylaminophenyl)-2-methyl-3-butyne-2-ol from 4-bromo-N,N-dimethylaniline and 2-methyl-3-butyne-2-ol Synthesis in which tri-tert-butylphosphine was handled in argon The procedures in Example A-19 or B-37 were repeated except that 0.157 g (0.3 mmol) of tri-tert-butylphosphonium tetraphenylborate of Example A-19 or 0.174 g (0.3 mmol) of tri-tert-butylphosphonium tetra-para-tolylborate of Example B-37 was replaced with 0.061 g (0.3 mmol) of tri-tert-butylphosphine, and except that the procedures were carried out in a glove box in which an argon atmosphere was strictly maintained. Consequently, 0.874 g of 4-(N,N-dimethylaminophenyl)-2-methyl-3-butyne-2-ol was obtained (yield: 86 mol % based on 4-bromo-N,N-dimethylaniline). The identification of the product was made by mass spectroscopy, $^1$H-NMR and $^{13}$C-NMR, and the results were in agreement with those of Example A-19 or B-37.

Comparative Example 36

Synthesis of 4-(N,N-dimethylaminophenyl)-2-methyl-3-butyne-2-ol from 4-bromo-N,N-dimethylaniline and 2-methyl-3-butyne-2-ol Synthesis in which tri-tert-butylphosphine was handled in air The procedures in Example A-19 or B-37 were repeated except that 0.157 g (0.3 mmol) of tri-tert-butylphosphonium tetraphenylborate of Example A-19 or 0.174 g (0.3 mmol) of tri-tert-butylphosphonium tetra-para-tolylborate of Example B-37 was replaced with 0.061 g (0.3 mmol) of tri-tert-butylphosphine. Tri-tert-butylphosphine generated white smoke while being handled in air. Little 4-(N,N-dimethylaminophenyl)-2-methyl-3-butyne-2-ol formed.

Comparative Example 37

Synthesis of (4-fluorophenyl)-2-methyl-3-butyne-2-ol from 1-bromo-4-fluorobenzene and 2-methyl-3-butyne-2-ol Synthesis in which tri-tert-butylphosphine was handled in argon The procedures in Example A-20 or B-38 were repeated except that 0.157 g (0.3 mmol) of tri-tert-butylphosphonium tetraphenylborate of Example A-20 or 0.174 g (0.3 mmol) of tri-tert-butylphosphonium tetra-para-tolylborate of Example B-38 was replaced with 0.061 g (0.3 mmol) of tri-tert-butylphosphine, and except that the procedures were carried out in a glove box in which an argon atmosphere was strictly maintained. Consequently, 0.860 g of (4-fluorophenyl)-2-methyl-3-butyne-2-ol was obtained (yield: 97 mol % based on 1-bromo-4-fluorobenzene). The identification of the product was made by $^1$H-NMR and $^{13}$C-NMR, and the results were in agreement with those of Example A-20 or B-38.

Comparative Example 38

Synthesis of (4-fluorophenyl)-2-methyl-3-butyne-2-ol from 1-bromo-4-fluorobenzene and 2-methyl-3-butyne-2-ol Synthesis in which tri-tert-butylphosphine was handled in air The procedures in Example A-20 or B-38 were repeated except that 0.157 g (0.3 mmol) of tri-tert-butylphosphonium tetraphenylborate of Example A-20 or 0.174 g (0.3 mmol) of tri-tert-butylphosphonium tetra-para-tolylborate of Example B-38 was replaced with 0.061 g (0.3 mmol) of tri-tert-butylphosphine. Tri-tert-butylphosphine generated white smoke while being handled in air. Little (4-fluorophenyl)-2-methyl-3-butyne-2-ol formed.

Comparative Example 39

Synthesis of 1,2-diphenyl-1-propanone from chlorobenzene and propiophenone

Synthesis in which tri-tert-butylphosphine was handled in argon

The procedures in Example A-21 or B-39 were repeated except that 0.052 g (0.1 mmol) of tri-tert-butylphosphonium tetraphenylborate of Example A-21 or 0.058 g (0.1 mmol) of tri-tert-butylphosphonium tetra-para-tolylborate of Example B-39 was replaced with 0.020 g (0.1 mmol) of tri-tert-butylphosphine, and except that the procedures were carried out in a glove box in which an argon atmosphere was strictly maintained. Consequently, 0.789 g of 1,2-diphenyl-1-propanone was obtained (yield: 75 mol % based on chlorobenzene). The identification of the product was made by mass spectroscopy, $^1$H-NMR and $^{13}$C-NMR, and the results were in agreement with those of Example A-21 or B-39.

Comparative Example 40

Synthesis of 1,2-diphenyl-1-propanone from chlorobenzene and propiophenone

Synthesis in which tri-tert-butylphosphine was handled in air

The procedures in Example A-21 or B-39 were repeated except that 0.052 g (0.1 mmol) of tri-tert-butylphosphonium tetraphenylborate of Example A-21 or 0.058 g (0.1 mmol) of tri-tert-butylphosphonium tetra-para-tolylborate of Example B-39 was replaced with 0.020 g (0.1 mmol) of tri-tert-butylphosphine. Tri-tert-butylphosphine generated white smoke while being handled in air. Little 1,2-diphenyl-1-propanone formed.

Comparative Example 41

Synthesis of 1,2-diphenyl-1-propanone from bromobenzene and propiophenone

Synthesis in which tri-tert-butylphosphine was handled in argon

The procedures in Example A-22 or B-40 were repeated except that 0.026 g (0.05 mmol) of tri-tert-butylphosphonium tetraphenylborate of Example A-22 or 0.029 g (0.05 mmol) of tri-tert-butylphosphonium tetra-para-tolylborate of Example B-40 was replaced with 0.010 g (0.05 mmol) of tri-tert-butylphosphine, and except that the procedures were carried out in a glove box in which an argon atmosphere was strictly maintained. Consequently, 1.998 g of 1,2-diphenyl-1-propanone was obtained (yield: 95 mol % based on bromobenzene). The identification of the product was made by mass spectroscopy, $^1$H-NMR and $^{13}$C-NMR, and the results were in agreement with those of Example A-22 or B-40.

Comparative Example 42

Synthesis of 1,2-diphenyl-1-propanone from bromobenzene and propiophenone

Synthesis in which tri-tert-butylphosphine was handled in air

The procedures in Example A-22 or B-40 were repeated except that 0.026 g (0.05 mmol) of tri-tert-butylphosphonium tetraphenylborate of Example A-22 or 0.029 g (0.05 mmol) of tri-tert-butylphosphonium tetra-para-tolylborate of Example B-40 was replaced with 0.010 g (0.05 mmol) of tri-tert-butylphosphine. Tri-tert-butylphosphine generated white smoke while being handled in air. Little 1,2-diphenyl-1-propanone formed.

Comparative Example 43

Synthesis of di-tert-butylphenyl malonate from chlorobenzene and di-tert-butyl malonate Synthesis in which tri-tert-butylphosphine was handled in argon The procedures in Example A-23 or B-41 were repeated except that 0.031 g (0.06 mmol) of tri-tert-butylphosphonium tetraphenylborate of Example A-23 or 0.035 g (0.06 mmol) of tri-tert-butylphosphonium tetra-para-tolylborate of Example B-41 was replaced with 0.012 g (0.06 mmol) of tri-tert-butylphosphine, and except that the procedures were carried out in a glove box in which an argon atmosphere was strictly maintained. Consequently, 0.746 g of di-tert-butylphenyl malonate was obtained (yield: 85 mol % based on chlorobenzene). The identification of the product was made by $^1$H-NMR and $^{13}$C-NMR, and the results were in agreement with those of Example A-23 or B-41.

Comparative Example 44

Synthesis of di-tert-butylphenyl malonate from chlorobenzene and di-tert-butyl malonate Synthesis in which tri-tert-butylphosphine was handled in air The procedures in Example A-23 or B-41 were repeated except that 0.031 g (0.06 mmol) of tri-tert-butylphosphonium tetraphenylborate of Example A-23 or 0.035 g (0.06 mmol) of tri-tert-butylphosphonium tetra-para-tolylborate of Example B-41 was replaced with 0.012 g (0.06 mmol) of tri-tert-butylphosphine. Tri-tert-butylphosphine generated white smoke while being handled in air. Little di-tert-butylphenyl malonate formed.

Comparative Example 45

Synthesis of ethyl-2-phenylcyanoacetate from chlorobenzene and ethyl cyanoacetate Synthesis in which tri-tert-butylphosphine was handled in argon The procedures in Example A-24 or B-42 were repeated except that 0.105 g (0.2 mmol) of tri-tert-butylphosphonium tetraphenylborate of Example A-24 or 0.116 g (0.2 mmol) of tri-tert-butylphosphonium tetra-para-tolylborate of Example B-42 was replaced with 0.040 g (0.2 mmol) of tri-tert-butylphosphine, and except that the procedures were carried out in a glove box in which an argon atmosphere was strictly maintained. Consequently, 0.354 g of ethyl-2-phenylcyanoacetate was obtained (yield: 37 mol % based on chlorobenzene). The identification of the product was made by mass spectroscopy, $^1$H-NMR and $^{13}$C-NMR, and the results were in agreement with those of Example A-24 or B-42.

Comparative Example 46

Synthesis of ethyl-2-phenylcyanoacetate from chlorobenzene and ethyl cyanoacetate Synthesis in which tri-tert-butylphosphine was handled in air The procedures in Example A-24 or B-42 were repeated except that 0.105 g (0.2 mmol) of tri-tert-butylphosphonium tetraphenylborate of Example A-24 or 0.116 g (0.2 mmol) of tri-tert-butylphosphonium tetra-para-tolylborate of Example B-42 was replaced with 0.040 g (0.2 mmol) of tri-tert-butylphosphine. Tri-tert-butylphosphine generated white smoke while being handled in air. Little ethyl-2-phenylcyanoacetate formed.

Comparative Example 47

Synthesis of triphenylamine from chlorobenzene and diphenylamine

Synthesis in which tri-tert-butylphosphine was handled in argon

The procedures in Example A-25 or B-43 were repeated except that 0.021 g (0.04 mmol) of tri-tert-butylphosphonium tetraphenylborate of Example A-25 or 0.023 g (0.04 mmol) of tri-tert-butylphosphonium tetra-para-tolylborate of Example B-43 was replaced with 0.008 g (0.04 mmol) of tri-tert-butylphosphine, and except that the procedures were carried out in a glove box in which an argon atmosphere was strictly maintained. Consequently, 8.164 g of triphenylamine was obtained (yield: 83 mol % based on diphenylamine). The melting point was 125-126° C.

Comparative Example 48

Synthesis of triphenylamine from chlorobenzene and diphenylamine

Synthesis in which tri-tert-butylphosphine was handled in air

The procedures in Example A-25 or B-43 were repeated except that 0.021 g (0.04 mmol) of tri-tert-butylphosphonium tetraphenylborate of Example A-25 or 0.023 g (0.04 mmol) of tri-tert-butylphosphonium tetra-para-tolylborate of Example B-43 was replaced with 0.008 g (0.04 mmol) of tri-tert-butylphosphine. Tri-tert-butylphosphine generated white smoke while being handled in air. Little triphenylamine formed.

Comparative Example 49

Synthesis of tert-butyl-2-methylphenyl ether from 2-chlorotoluene and sodium-tert-butoxide Synthesis in which tri-tert-butylphosphine was handled in argon The procedures in Example A-26 or B-44 were repeated except that 0.784 g (1.5 mmol) of tri-tert-butylphosphonium tetraphenylborate of Example A-26 or 0.868 g (1.5 mmol) of tri-tert-butylphosphonium tetra-para-tolylborate of Example B-44 was replaced with 0.303 g (1.5 mmol) of tri-tert-butylphosphine, and except that the procedures were carried out in a glove box in which an argon atmosphere was strictly maintained. Consequently, 7.712 g of tert-butyl-2-methylphenyl ether was obtained (yield: 94 mol % based on 2-chlorotoluene). The boiling point was 75° C./9 Torr.

Comparative Example 50

Synthesis of tert-butyl-2-methylphenyl ether from 2-chlorotoluene and sodium-tert-butoxide Synthesis in which tri-tert-butylphosphine was handled in air The procedures in Example A-26 or B-44 were repeated except that 0.784 g (1.5 mmol) of tri-tert-butylphosphonium tetraphenylborate of Example A-26 or 0.868 g (1.5 mmol) of tri-tert-butylphosphonium tetra-para-tolylborate of Example B-44 was replaced with 0.303 g (1.5 mmol) of tri-tert-butylphosphine. Tri-tert-butylphosphine generated white smoke while being handled in air. Little tert-butyl-2-methylphenyl ether formed.

Comparative Example 51

Synthesis of 2-methoxy-4,2'-dimethylphenyl ether from 2-chlorotoluene and 2-methoxy-4-methylphenol Synthesis in which tri-tert-butylphosphine was handled in argon The procedures in Example A-27 or B-45 were repeated except that 1.045 g (2 mmol) of tri-tert-butylphosphonium tetraphenylborate of Example A-27 or 1.157 g (2 mmol) of tri-tert-butylphosphonium tetra-para-tolylborate of Example B-45 was replaced with 0.405 g (2 mmol) of tri-tert-butylphosphine, and except that the procedures were carried out in a glove box in which an argon atmosphere was strictly maintained. Consequently, 6.958 g of 2-methoxy-4,2'-dimethylphenyl ether was obtained (yield: 76 mol % based on 2-chlorotoluene). The identification of the product was made by mass spectroscopy, $^1$H-NMR and $^{13}$C-NMR, and the results were in agreement with those of Example A-27 or Comparative Example 52

Synthesis of 2-methoxy-4,2'-dimethylphenyl ether from 2-chlorotoluene and 2-methoxy-4-methylphenol Synthesis in which tri-tert-butylphosphine was handled in air The procedures in Example A-27 or B-45 were repeated except that 1.045 g (2 mmol) of tri-tert-butylphosphonium tetraphenylborate of Example A-27 or 1.157 g (2 mmol) of tri-tert-butylphosphonium tetra-para-tolylborate of Example B-45 was replaced with 0.405 g (2 mmol) of tri-tert-butylphosphine. Tri-tert-butylphosphine generated white smoke while being handled in air. Little 2-methoxy-4,2'-dimethylphenyl ether formed.

Comparative Example 53

Synthesis of triphenylamine from bromobenzene and diphenylamine

Synthesis in which n-butyldicyclohexylphosphine was handled in argon

The procedures in Example B-48 were repeated except that 0.690 g (1.20 mmol) of n-butyldicyclohexylphosphonium tetraphenylborate of Example B-48 was replaced with 0.305 g (1.20 mmol) of n-butyldicyclohexylphosphine, and except that the procedures were carried out in a glove box in which an argon atmosphere was strictly maintained. Consequently, 8.343 g of triphenylamine was obtained (yield: 85 mol % based on diphenylamine). The melting point was 125-126° C.

Comparative Example 54

Synthesis of triphenylamine from bromobenzene and diphenylamine

Synthesis in which n-butyldicyclohexylphosphine was handled in air

The procedures in Example B-48 were repeated except that 0.690 g (1.20 mmol) of n-butyldicyclohexylphosphonium tetraphenylborate of Example B-48 was replaced with 0.305 g (1.20 mmol) of n-butyldicyclohexylphosphine. Consequently, 2.943 g of triphenylamine was obtained (yield: 30 mol % based on diphenylamine). The melting point was 125-126° C. Handling n-butyldicyclohexylphosphine in air resulted in the lowered yield of triphenylamine.

Comparative Example 55

Synthesis of triphenylamine from bromobenzene and diphenylamine

Synthesis in which di-tert-butylphenylphosphine was handled in argon

The procedures in Example B-49 were repeated except that 0.065 g (0.12 mmol) of di-tert-butylphenylphosphonium tetraphenylborate of Example B-49 was replaced with 0.027 g (0.12 mmol) of di-tert-butylphenylphosphine, and except that the procedures were carried out in a glove box in which an argon atmosphere was strictly maintained. Consequently, 9.020 g of triphenylamine was obtained (yield: 92 mol % based on diphenylamine). The melting point was 125-126° C.

Comparative Example 56

Synthesis of triphenylamine from bromobenzene and diphenylamine

Synthesis in which di-tert-butylphenylphosphine was handled in air

The procedures in Example B-49 were repeated except that 0.065 g (0.12 mmol) of di-tert-butylphenylphosphonium tetraphenylborate of Example B-49 was replaced with 0.027 g (0.12 mmol) of di-tert-butylphenylphosphine. Consequently, 6.869 g of triphenylamine was obtained (yield: 70 mol % based on diphenylamine). The melting point was 125-126° C. Handling di-tert-butylphenylphosphine in air resulted in the lowered yield of triphenylamine.

Comparative Example 57

Synthesis of triphenylamine from bromobenzene and diphenylamine

Synthesis in which 2-biphenylyl-di-tert-butylphosphine was handled in argon

The procedures in Example B-50 were repeated except that 0.074 g (0.12 mmol) of 2-biphenylyl-di-tert-butylphosphonium tetraphenylborate of Example B-SO was replaced with 0.036 g (0.12 mmol) of 2-biphenylyl-di-tert-butylphosphine, and except that the procedures were carried out in a glove box in which an argon atmosphere was strictly maintained. Consequently, 8.535 g of triphenylamine was obtained (yield: 87 mol % based on diphenylamine). The melting point was 125-126° C.

Comparative Example 58

Synthesis of triphenylamine from bromobenzene and diphenylamine

Synthesis in which 2-biphenylyl-di-tert-butylphosphine was handled in air

The procedures in Example B-50 were repeated except that 0.074 g (0.12 mmol) of 2-biphenylyl-di-tert-butylphosphonium tetraphenylborate of Example B-50 was replaced with 0.036 g (0.12 mmol) of 2-biphenylyl-di-tert-butylphosphine. Consequently, 6.378 g of triphenylamine was obtained (yield:

65 mol % based on diphenylamine). The melting point was 125-126° C. Handling 2-biphenylyl-di-tert-butylphosphine in air resulted in the lowered yield of triphenylamine.

Comparative Example 59

Synthesis of triphenylamine from bromobenzene and diphenylamine

Synthesis in which di-tert-butyl-1-naphthylphosphine was handled in argon

The procedures in Example B-51 were repeated except that 0.071 g (0.12 mmol) of di-tert-butyl-1-naphthylphosphonium tetraphenylborate of Example B-51 was replaced with 0.033 g (0.12 mmol) of di-tert-butyl-1-naphthylphosphine, and except that the procedures were carried out in a glove box in which an argon atmosphere was strictly maintained. Consequently, 8.340 g of triphenylamine was obtained (yield: 85 mol % based on diphenylamine). The melting point was 125-126° C.

Comparative Example 60

Synthesis of triphenylamine from bromobenzene and diphenylamine

Synthesis in which di-tert-butyl-1-naphthylphosphine was handled in air

The procedures in Example B-51 were repeated except that 0.071 g (0.12 mmol) of di-tert-butyl-1-naphthylphosphonium tetraphenylborate of Example B-51 was replaced with 0.033 g (0.12 mmol) of di-tert-butyl-1-naphthylphosphine. Consequently, 6.380 g of triphenylamine was obtained (yield: 65 mol % based on diphenylamine). The melting point was 125-126° C. Handling di-tert-butyl-1-naphthylphosphine in air resulted in the lowered yield of triphenylamine.

<Consideration of Examples A Relating to Trialkylphosphonium Tetraphenylborates>

The results of Examples A-1 to A-4 confirmed that the trialkylphosphonium tetraphenylborates were produced more safely, by simpler reaction operations and in higher yields than by the conventional processes.

The results of Comparative Examples 3, 4, 7 to 16, and 19 to 52 confirmed that the trialkylphosphines could be used in combination with transition metals, salts thereof, oxides thereof or complexes thereof when the trialkylphosphines were handled in an inert gas, and that the trialkylphosphines were immediately oxidized in air and could not be used in combination with transition metals, salts thereof, oxides thereof or complexes thereof in air. The results of Examples A-5 to A-27 confirmed that the trialkylphosphonium tetraphenylborates could be used in combination with transition metals, salts thereof, oxides thereof or complexes thereof when the trialkylphosphonium tetraphenylborates were handled in air.

<Consideration of Examples B Relating to Novel Phosphonium Borate Compounds>

The results of Examples B-1 to B-17 and Examples B-46 to B-47 confirmed that the novel phosphonium borate compounds were produced more safely, by simpler reaction operations and in higher yields.

The results of Comparative Examples 1 to 60 confirmed that the alkylphosphines could be used in combination with transition metals, salts thereof, oxides thereof or complexes thereof when the alkylphosphines were handled in an inert gas, and that the alkylphosphines were immediately oxidized in air and could not be used in combination with transition metals, salts thereof, oxides thereof or complexes thereof in air. The results of Examples B-18 to B-45 and Examples B-48 to B-51 confirmed that the alkylphosphonium borate compounds could be used in combination with transition metals, salts thereof, oxides thereof or complexes thereof when the alkylphosphonium borate compounds were handled in air.

The invention claimed is:

1. A process for producing a phosphonium borate compound, which comprises the following steps 1 and 2:

(step 1) reacting a phosphine with HCl to produce a phosphine hydrochloride, the phosphine being represented by Formula (II):

$$(R^1)(R^2)(R^3)P \qquad (II)$$

wherein $R^1$ is a primary alkyl group of 1 to 20 carbon atoms, a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine hydrochloride being represented by Formula (III):

$$(R^1)(R^2)(R^3)PH \cdot Cl \qquad (III)$$

wherein $R^1$, $R^2$ and $R^3$ are as defined in Formula (II); and (step 2) reacting the phosphine hydrochloride with a tetraarylborate compound represented by Formula (IV):

$$M \cdot BAr_4 \qquad (IV)$$

wherein M is lithium, sodium, potassium, magnesium halide or calcium halide, and Ar is an aryl group of 6 to 20 carbon atoms;

the phosphonium borate compound being represented by Formula (I):

$$(R^1)(R^2)(R^3)PH \cdot BAr_4 \qquad (I)$$

wherein $R^1$, $R^2$ and $R^3$ are as defined in Formula (II), and Ar is as defined in Formula (IV);

wherein step 1 is conducted in the absence of the tetraaryl borate compound used in step 2 and wherein the solution of the phosphine hydrochloride obtained in Step 1 and provided for step 2 is not subjected to concentration.

2. A process for producing a trialkylphosphonium tetraphenylborate according to claim 1, which comprises the following steps 1 and 2:

(step 1) reacting a trialkylphosphine with HCl to produce a trialkylphosphine hydrochloride, the trialkylphosphine being represented by Formula (II):

$$(R^1)(R^2)(R^3)P \qquad (II)$$

wherein $R^1$, $R^2$ and $R^3$ are ethyl, n-butyl, tert-butyl or cyclohexyl groups, and are the same;

the trialkylphosphine hydrochloride being represented by Formula (III):

$$(R^1)(R^2)(R^3)PH \cdot Cl \qquad (III)$$

wherein $R^1$, $R^2$ and $R^3$ are as defined in Formula (II); and (step 2) reacting the trialkylphosphine hydrochloride with a tetraphenylborate compound represented by Formula (IV):

$$M \cdot BAr_4 \qquad (IV)$$

wherein M is lithium, sodium, potassium, magnesium halide or calcium halide, and Ar is phenyl group;

the trialkylphosphonium tetraphenylborate being represented by Formula (I):

$$(R^1)(R^2)(R^3)PH \cdot BAr_4 \qquad (I)$$

wherein $R^1$, $R^2$ and $R^3$ are as defined in Formula (II), and Ar is as defined in Formula (IV);

wherein step 1 is conducted in the absence of the tetraaryl borate compound used in step 2 and wherein the solution of the phosphine hydrochloride obtained in step 1 and provided for step 2 is not subjected to concentration.

3. A process for producing a novel phosphonium borate compound according to claim 1, which comprises the following steps 1 and 2:

(step 1) reacting a phosphine with HCl to produce a phosphine hydrochloride, the phosphine being represented by Formula (II):

$$(R^1)(R^2)(R^3)P \qquad (II)$$

wherein $R^1$ is a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine hydrochloride being represented by Formula (III):

$$(R^1)(R^2)(R^3)PH \cdot Cl \qquad (III)$$

wherein $R^1$, $R^2$ and $R^3$ are as defined in Formula (II); and (step 2) reacting the phosphine hydrochloride with a tetraarylborate compound represented by Formula (IV):

$$M \cdot BAr_4 \qquad (IV)$$

wherein M is lithium, sodium, potassium, magnesium halide or calcium halide, and Ar is an aryl group of 6 to 20 carbon atoms;

the phosphonium borate compound being represented by Formula (I):

$$(R^1)(R^2)(R^3)PH \cdot BAr_4 \qquad (I)$$

wherein $R^1$, $R^2$ and $R^3$ are as defined in Formula (II), Ar is as defined in Formula (IV), $R^1$, $R^2$ and $R^3$ cannot be tert-butyl groups simultaneously and Ar cannot be phenyl group at the same time, and $R^1$, $R^2$ and $R^3$ cannot be cyclohexyl groups simultaneously and Ar cannot be phenyl group at the same time;

wherein step 1 is conducted in the absence of the tetraaryl borate compound used in step 2 and wherein the solution of the phosphine hydrochloride obtained in step 1 and provided for step 2 is not subjected to concentration.

4. A process for producing a phosphonium borate compound, which comprises the following steps 1 and 2:

(step 1) reacting a phosphine with $H_2SO_4$ to produce a phosphine sulfate, the phosphine being represented by Formula (II):

$$(R^1)(R^2)(R^3)P \qquad (II)$$

wherein $R^1$ is a primary alkyl group of 1 to 20 carbon atoms, a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine sulfate being represented by Formula (V):

$$[(R^1)(R^2)(R^3)PH]_{(2-n)} \cdot H_n SO_4 \qquad (V)$$

wherein $R^1$, $R^2$ and $R^3$ are as defined in Formula (II), and n is an integer of 0 or 1; and (step 2) reacting the phosphine sulfate with a tetraarylborate compound represented by Formula (IV):

$$M \cdot BAr_4 \qquad (IV)$$

wherein M is lithium, sodium, potassium, magnesium halide or calcium halide, and Ar is an aryl group of 6 to 20 carbon atoms;

the phosphonium borate compound being represented by Formula (I):

$$(R^1)(R^2)(R^3)PH \cdot BAr_4 \qquad (I)$$

wherein $R^1$, $R^2$ and $R^3$ are as defined in Formula (II), and Ar is as defined in Formula (IV);

wherein step 1 is conducted in the absence of the tetraaryl borate compound used in step 2 and wherein the solution of the phosphine sulfate obtained in step 1 and provided for step 2 is not subjected to concentration.

5. A process for producing a trialkylphosphonium tetraphenylborate according to claim 4, which comprises the following steps 1 and 2:

(step 1) reacting a trialkylphosphine with $H_2SO_4$ to produce a trialkylphosphine sulfate, the trialkylphosphine being represented by Formula (II):

$$(R^1)(R^2)(R^3)P \qquad (II)$$

wherein $R^1$, $R^2$ and $R^3$ are ethyl, n-butyl, tert-butyl or cyclohexyl groups, and are the same;

the trialkylphosphine sulfate being represented by Formula (V):

$$[(R^1)(R^2)(R^3)PH]_{(2-n)} \cdot H_n SO_4 \qquad (V)$$

wherein $R^1$, $R^2$ and $R^3$ are as defined in Formula (II), and n is an integer of 0 or 1; and (step 2) reacting the trialkylphosphine sulfate with a tetraphenylborate compound represented by Formula (IV):

$$M \cdot BAr_4 \qquad (IV)$$

wherein M is lithium, sodium, potassium, magnesium halide or calcium halide, and Ar is phenyl group;

the trialkylphosphonium tetraphenylborate being represented by Formula (I):

$$(R^1)(R^2)(R^3)PH \cdot BAr_4 \qquad (I)$$

wherein $R^1$, $R^2$ and $R^3$ are as defined in Formula (II), and Ar is as defined in Formula (IV);

wherein step 1 is conducted in the absence of the tetraaryl borate compound used in step 2 and wherein the solution of the phosphine sulfate obtained in step 1 and provided for step 2 is not subjected to concentration.

6. A process for producing a novel phosphonium borate compound according to claim 4, which comprises the following steps 1 and 2:

(step 1) reacting a phosphine with $H_2SO_4$ to produce a phosphine sulfate, the phosphine being represented by Formula (II):

$$(R^1)(R^2)(R^3)P \qquad (II)$$

wherein $R^1$ is a secondary alkyl group of 3 to 20 carbon atoms, a tertiary alkyl group of 4 to 20 carbon atoms, or a cycloalkyl group of 3 to 20 carbon atoms;

$R^2$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aralkyl group of 7 to 20 carbon atoms, or an allyl group of 3 to 20 carbon atoms;

$R^3$ is a hydrogen atom, a primary alkyl group of 1 to 20 carbon atoms, a secondary alkyl group of 3 to 20 carbon atoms, a tertiary alkyl group of 4 to 20 carbon atoms, a cycloalkyl group of 3 to 20 carbon atoms, an aryl group of 6 to 30 carbon atoms, an aralkyl group of 7 to 20 carbon atoms, an alkenyl group of 2 to 20 carbon atoms, an alkynyl group of 2 to 20 carbon atoms, or an allyl group of 3 to 20 carbon atoms; and $R^1$, $R^2$ and $R^3$ may be the same or different from one another;

the phosphine sulfate being represented by Formula (V):

$$[(R^1)(R^2)(R^3)PH]_{(2-n)} \cdot H_n SO_4 \qquad (V)$$

wherein $R^1$, $R^2$ and $R^3$ are as defined in Formula (II), and n is an integer of 0 or 1; and (step 2) reacting the phosphine sulfate with a tetraarylborate compound represented by Formula (IV):

$$M \cdot BAr_4 \qquad (IV)$$

wherein M is lithium, sodium, potassium, magnesium halide or calcium halide, and Ar is an aryl group of 6 to 20 carbon atoms;

the phosphonium borate compound being represented by Formula (I):

$$(R^1)(R^2)(R^3)PH \cdot BAr_4 \qquad (I)$$

wherein $R^1$, $R^2$ and $R^3$ are as defined in Formula (II), Ar is as defined in Formula (IV), $R^1$, $R^2$ and $R^3$ cannot be tert-butyl groups simultaneously and Ar cannot be phenyl group at the same time, and $R^1$, $R^2$ and $R^3$ cannot be cyclohexyl groups simultaneously and Ar cannot be phenyl group at the same time;

wherein step 1 is conducted in the absence of the tetraaryl borate compound used in step 2 and wherein the solution of the phosphine sulfate obtained in step 1 and provided for step 2 is not subjected to concentration.

* * * * *